US012760371B2

(12) United States Patent
Whetstine et al.

(10) Patent No.: US 12,760,371 B2
(45) Date of Patent: Oct. 13, 2026

(54) COMPOSITIONS AND METHODS FOR REGULATING EGFR AMPLIFICATION IN CANCER CELLS FOR IMPROVING EFFICACY OF EGFR-TARGETED ANTI-CANCER AGENTS

(71) Applicants: Institute for Cancer Research, Philadelphia, PA (US); The General Hospital Corporation, Boston, MA (US)

(72) Inventors: Johnathan R. Whetstine, Winchester, MA (US); Thomas L Clarke, Boston, MA (US)

(73) Assignees: Institute for Cancer Research, Philadelphia, PA (US); The General Hospital Corporation, Boston, MA (US)

( * ) Notice: Subject to any disclaimer, the term of this patent is extended or adjusted under 35 U.S.C. 154(b) by 1131 days.

(21) Appl. No.: 17/745,483

(22) Filed: May 16, 2022

(65) Prior Publication Data

US 2022/0411879 A1 Dec. 29, 2022

Related U.S. Application Data

(63) Continuation-in-part of application No. PCT/US2020/060808, filed on Nov. 16, 2020.

(60) Provisional application No. 62/935,763, filed on Nov. 15, 2019.

(51) Int. Cl.

| | |
|---|---|
| ***A61P 35/00*** | (2006.01) |
| ***A61K 31/4706*** | (2006.01) |
| ***A61K 31/506*** | (2006.01) |
| ***A61K 31/517*** | (2006.01) |
| ***A61K 31/5377*** | (2006.01) |
| ***A61K 39/395*** | (2006.01) |
| ***C12Q 1/6886*** | (2018.01) |

(52) U.S. Cl.

CPC ........ *C12Q 1/6886* (2013.01); *A61K 31/4706* (2013.01); *A61K 31/506* (2013.01); *A61K 31/517* (2013.01); *A61K 31/5377* (2013.01); *A61K 39/3955* (2013.01); *A61P 35/00* (2018.01); *C12Q 2600/106* (2013.01); *C12Q 2600/156* (2013.01)

(58) Field of Classification Search

None

See application file for complete search history.

(56) References Cited

FOREIGN PATENT DOCUMENTS

| | | |
|---|---|---|
| WO | 2014/144850 A1 | 9/2014 |
| WO | 2018/183370 A2 | 10/2018 |

OTHER PUBLICATIONS

Moroni, M. et al. Gene copy number for epidermal growth factor receptor (EGFR) and clinical response to antiEGFR treatment in colorectal cancer: a cohort study. Lancet Oncol. May 2005;6(5):279-86 (Year: 2005).*

Kurmasheva, R. et al. Initial Testing (Stage 1) of Tazemetostat (EPZ-6438), a Novel EZH2 Inhibitor, by the Pediatric Preclinical Testing Program. Pediatr Blood Cancer. Mar. 2017;64(3):10.1002/pbc.26218 (Year: 2017).*

Mishra, S. et al. Cross-talk Between Lysine Modifying Enzymes Controls Site-specific DNA Amplifications. Cell. Aug. 9, 2018;174(4):803-817.e16 (Year: 2018).*

Black, J. et al. Hypoxia drives transient site-specific copy gain and drug-resistant gene expression .Genes Dev. May 15, 2015;29(10):1018-1031 (Year: 2015).*

Black, J. et al. Genes Dev. May 15, 2015;29(10):1018-1031 (Year: 2015).*

Moroni, M. et al. Lancet Oncol. May 2005;6(5):279-86 (Year: 2005).*

Kurmasheva, R. et al. Pediatr Blood Cancer. Mar. 2017;64(3): 10.1002/pbc.26218 (Year: 2017).*

Hanahan D, Weinberg RA. Hallmarks of cancer: the next generation. Cell 2011;144(5):646-74 doi 10.1016/j.cell.2011.02.013.

Mishra S, Whetstine JR. Different Facets of Copy Number Changes: Permanent, Transient, and Adaptive. Mol Cell Biol 2016 doi 10.1128/MCB.00652-15.

Diskin SJ, Hou C, Glessner JT, Attiyeh EF, Laudenslager M, Bosse K, et al. Copy number variation at 1q21.1 associated with neuroblastoma. Nature 2009;459(7249):987-91 doi 10.1038/nature08035.

Fonseca R, Van Wier SA, Chng WJ, Ketterling R, Lacy MQ, Dispenzieri A, et al. Prognostic value of chromosome 1q21 gain by fluorescent in situ hybridization and increase CKS1B expression in myeloma. Leukemia 2006;20(11):2034-40 doi 10.1038/sj.leu.2404403.

Inoue J, Otsuki T, Hirasawa A, Imoto I, Matsuo Y, Shimizu S, et al. Overexpression of PDZK1 within the 1q12-q22 amplicon is likely to be associated with drug-resistance phenotype in multiple myeloma. The American journal of pathology 2004;165(1):71-81 doi 10.1016/S0002-9440(10)63276-2.

Beroukhim R, Mermel CH, Porter D, Wei G, Raychaudhuri S, Donovan J, et al. The landscape of somatic copy-number alteration across human cancers. Nature 2010;463(7283):899-905 doi 10.1038/nature08822.

Mishra S, Van Rechem C, Pal S, Clarke TL, Chakraborty D, Mahan SD, et al. Cross-talk between Lysine-Modifying Enzymes Controls Site-Specific DNA Amplifications. Cell 2018;174(4):803-17 e16 doi 10.1016/j.cell.2018.06.018.

(Continued)

*Primary Examiner* — Clinton A Brooks

*Assistant Examiner* — Nicola Maria Bauer

(74) *Attorney, Agent, or Firm* — & Howson, LLP

(57) ABSTRACT

Compositions and methods for regulating EGFR amplification in cancer are disclosed.

13 Claims, 41 Drawing Sheets

Specification includes a Sequence Listing.

(56) References Cited

OTHER PUBLICATIONS

Turner KM, Deshpande V, Beyter D, Koga T, Rusert J, Lee C, et al. Extrachromosomal oncogene amplification drives tumour evolution and genetic heterogeneity. Nature 2017;543(7643):122-5 doi 10.1038/nature21356.
Nathanson DA, Gini B, Mottahedeh J, Visnyei K, Koga T, Gomez G, et al. Targeted therapy resistance mediated by dynamic regulation of extrachromosomal mutant EGFR DNA. Science 2014;343(6166):72-6 doi 10.1126/science.1241328.
Black JC, Atabakhsh E, Kim J, Biette KM, Van Rechem C, Ladd B, et al. Hypoxia drives transient site-specific copy gain and drug-resistant gene expression. Genes & development 2015;29(10):1018-31 doi 10.1101/gad.259796.115.
Black JC, Manning AL, Van Rechem C, Kim J, Ladd B, Cho J, et al. KDM4A lysine demethylase induces site-specific copy gain and rereplication of regions amplified in tumors. Cell 2013;154(3):541-55 doi 10.1016/j.cell.2013.06.051.
Black JC, Zhang H, Kim J, Getz G, Whetstine JR. Regulation of Transient Site-specific Copy Gain by microRNA. The Journal of biological chemistry 2016 doi 10.1074/jbc.M115.711648.
Black JC, Whetstine JR. Too little O2 Too much gain. Cell cycle 2015;14(18):2869-70 doi 10.1080/15384101.2015.1076659.
Junttila MR, de Sauvage FJ. Influence of tumour micro-environment heterogeneity on therapeutic response. Nature 2013;501(7467):346-54 doi 10.1038/nature12626.
Hirsch FR, Varella-Garcia M, Bunn PA, Jr., Di Maria MV, Veve R, Bremmes RM, et al. Epidermal growth factor receptor in non-small-cell lung carcinomas: correlation between gene copy number and protein expression and impact on prognosis. J Clin Oncol 2003;21(20):3798-807 doi 10.1200/JCO.2003.11.069.
Sullivan I, Planchard D. Next-Generation EGFR Tyrosine Kinase Inhibitors for Treating EGFR-Mutant Lung Cancer beyond First Line. Front Med (Lausanne) 2016;3:76 doi 10.3389/fmed.2016.00076.
Hirsch FR, Varella-Garcia M, McCoy J, West H, Xavier AC, Gumerlock P, et al. Increased epidermal growth factor receptor gene copy number detected by fluorescence in situ hybridization associates with increased sensitivity to gefitinib in patients with bronchioloalveolar carcinoma subtypes: a Southwest Oncology Group Study. J Clin Oncol 2005;23(28):6838-45 doi 10.1200/JCO.2005.01.2823.
Maron SB, Alpert L, Kwak HA, Lomnicki S, Chase L, Xu D, et al. Targeted Therapies for Targeted Populations: Anti-EGFR Treatment for EGFR-Amplified Gastroesophageal Adenocarcinoma. Cancer Discov 2018;8(6):696-713 doi 10.1158/2159-8290.CD-17-1260.
Huang J, Fan Q, Lu P, Ying J, Ma C, Liu W, et al. Icotinib in Patients with Pretreated Advanced Esophageal Squamous Cell Carcinoma with EGFR Overexpression or EGFR Gene Amplification: A Single-Arm, Multicenter Phase 2 Study. J Thorac Oncol 2016;11(6):910-7 doi 10.1016/j.jtho.2016.02.020.
Luber B, Deplazes J, Keller G, Walch A, Rauser S, Eichmann M, et al. Biomarker analysis of cetuximab plus oxaliplatin/leucovorin/5-fluorouracil in first-line metastatic gastric and oesophago-gastric junction cancer: results from a phase II trial of the Arbeitsgemeinschaft Internistische Onkologie (AIO). BMC Cancer 2011;11:509 doi 10.1186/1471-2407-11-509.
Petty RD, Dahle-Smith A, Stevenson DAJ, Osborne A, Massie D, Clark C, et al. Gefitinib and EGFR Gene Copy Number Aberrations in Esophageal Cancer. J Clin Oncol 2017;35(20):2279-87 doi 10.1200/JCO.2016.70.3934.
Herbst RS, Redman MW, Kim ES, Semrad TJ, Bazhenova L, Masters G, et al. Cetuximab plus carboplatin and paclitaxel with or without bevacizumab versus carboplatin and paclitaxel with or without bevacizumab in advanced NSCLC (SWOG S0819): a randomised, phase 3 study. Lancet Oncol 2018;19(1):101-14 doi 10.1016/S1470-2045(17) 30694-0.
Lewis PW, Muller MM, Koletsky MS, Cordero F, Lin S, Banaszynski LA, et al. Inhibition of PRC2 activity by a gain-of-function H3 mutation found in pediatric glioblastoma. Science 2013;340(6134):857-61 doi 10.1126/science.1232245.
Darrow EM, Huntley MH, Dudchenko O, Stamenova EK, Durand NC, Sun Z, et al. Deletion of DXZ4 on the human inactive X chromosome alters higher-order genome architecture. Proc Natl Acad Sci U S A 2016;113(31):E4504-12 doi 10.1073/pnas.1609643113.
Kundu S, Ji F, Sunwoo H, Jain G, Lee JT, Sadreyev RI, et al. Polycomb Repressive Complex 1 Generates Discrete Compacted Domains that Change during Differentiation. Mol Cell 2017;65(3):432-46 e5 doi 10.1016/j.molcel.2017.01.009.
Consortium EP. An integrated encyclopedia of DNA elements in the human genome. Nature 2012;489(7414):57-74 doi 10.1038/nature11247.
Rao SS, Huntley MH, Durand NC, Stamenova EK, Bochkov ID, Robinson JT, et al. A 3D map of the human genome at kilobase resolution reveals principles of chromatin looping. Cell 2014;159(7):1665-80 doi 10.1016/j.cell.2014.11.021.
Stafford JM, Lee CH, Voigt P, Descostes N, Saldana-Meyer R, Yu JR, et al. Multiple modes of PRC2 inhibition elicit global chromatin alterations in H3K27M pediatric glioma. Sci Adv 2018;4(10):eaau5935 doi 10.1126/sciadv.aau5935.
Black JC, Van Rechem C, Whetstine JR. Histone lysine methylation dynamics: establishment, regulation, and biological impact. Mol Cell 2012;48(4):491-507 doi 10.1016/j.molcel.2012.11.006.
Whetstine JR, Nottke A, Lan F, Huarte M, Smolikov S, Chen Z, et al. Reversal of histone lysine trimethylation by the JMJD2 family of histone demethylases. Cell 2006;125(3):467-81 doi 10.1016/j.cell.2006.03.028.
Huang Y, Fang J, Bedford MT, Zhang Y, Xu RM. Recognition of histone H3 lysine-4 methylation by the double tudor domain of JMJD2A. Science 2006;312(5774):748-51 doi 10.1126/science.1125162.
Metzger E, Stepputtis SS, Strietz J, Preca BT, Urban S, Willmann D, et al. KDM4 Inhibition Targets Breast Cancer Stem-like Cells. Cancer Res 2017;77(21):5900-12 doi 10.1158/0008-5472.CAN-17-1754.
Amann J, Kalyankrishna S, Massion PP, Ohm JE, Girard L, Shigematsu H, et al. Aberrant epidermal growth factor receptor signaling and enhanced sensitivity to EGFR inhibitors in lung cancer. Cancer Res 2005;65(1):226-35.
Varella-Garcia M. Stratification of non-small cell lung cancer patients for therapy with epidermal growth factor receptor inhibitors: the EGFR fluorescence in situ hybridization assay. Diagn Pathol 2006;1:19 doi 10.1186/1746-1596-1-19.
Chen YK, Bonaldi T, Cuomo A, Del Rosario JR, Hosfield DJ, Kanouni T, et al. Design of KDM4 Inhibitors with Antiproliferative Effects in Cancer Models. ACS Med Chem Lett 2017;8(8):869-74 doi 10.1021/acsmedchemlett.7b00220.
Egan B, Yuan CC, Craske ML, Labhart P, Guler GD, Arnott D, et al. An Alternative Approach to ChIP-Seq Normalization Enables Detection of Genome-Wide Changes in Histone H3 Lysine 27 Trimethylation upon EZH2 Inhibition. PLoS One 2016;11(11):e0166438 doi 10.1371/journal.pone.0166438.
Yang X, Li F, Konze KD, Meslamani J, Ma A, Brown PJ, et al. Structure-Activity Relationship Studies for Enhancer of Zeste Homologue 2 (EZH2) and Enhancer of Zeste Homologue 1 (EZH1) Inhibitors. J Med Chem 2016;59(16):7617-33 doi 10.1021/acs.jmedchem.6b00855.
Katona BW, Liu Y, Ma A, Jin J, Hua X. EZH2 inhibition enhances the efficacy of an EGFR inhibitor in suppressing colon cancer cells. Cancer Biol Ther 2014;15(12):1677-87 doi 10.4161/15384047.2014.972776.
Shilatifard A. The COMPASS family of histone H3K4 methylases: mechanisms of regulation in development and disease pathogenesis. Annu Rev Biochem 2012;81:65-95 doi 10.1146/annurev-biochem-051710-134100.
Schuettengruber B, Bourbon HM, Di Croce L, Cavalli G. Genome Regulation by Polycomb and Trithorax: 70 Years and Counting. Cell 2017;171(1):34-57 doi 10.1016/j.cell.2017.08.002.

(56) References Cited

OTHER PUBLICATIONS

Rickels R, Hu D, Collings CK, Woodfin AR, Piunti A, Mohan M, et al. An Evolutionary Conserved Epigenetic Mark of Polycomb Response Elements Implemented by Trx/MLL/COMPASS. Mol Cell 2016;63(2):318-28 doi 10.1016/j.molcel.2016.06.018.

Koubi M, Poplineau M, Vernerey J, N'Guyen L, Tiberi G, Garciaz S, et al. Regulation of the positive transcriptional effect of PLZF through a non-canonical EZH2 activity. Nucleic Acids Res 2018;46(7):3339-50 doi 10.1093/nar/gky080.

Johansson C, Velupillai S, Tumber A, Szykowska A, Hookway ES, Nowak RP, et al. Structural analysis of human KDM5B guides histone demethylase inhibitor development. Nat Chem Biol 2016;12(7):539-45 doi 10.1038/nchembio.2087.

Horton JR, Liu X, Gale M, Wu L, Shanks JR, Zhang X, et al. Structural Basis for KDM5A Histone Lysine Demethylase Inhibition by Diverse Compounds. Cell Chem Biol 2016;23(7):769-81 doi 10.1016/j.chembiol.2016.06.006.

Sharma SV, Lee DY, Li B, Quinlan MP, Takahashi F, Maheswaran S, et al. A chromatin-mediated reversible drug-tolerant state in cancer cell subpopulations. Cell 2010;141(1):69-80 doi 10.1016/j.cell.2010.02.027.

William D, Mokri P, Lamp N, Linnebacher M, Classen CF, Erbersdobler A, et al. Amplification of the EGFR gene can be maintained and modulated by variation of EGF concentrations in in vitro models of glioblastoma multiforme. PLoS One 2017;12(9):e0185208 doi 10.1371/journal.pone.0185208.

Moller HD, Mohiyuddin M, Prada-Luengo I, Sailani MR, Halling JF, Plomgaard P, et al. Circular DNA elements of chromosomal origin are common in healthy human somatic tissue. Nat Commun 2018;9(1):1069 doi 10.1038/s41467-018-03369-8.

Smith G, Taylor-Kashton C, Dushnicky L, Symons S, Wright J, Mai S. c-Myc-induced extrachromosomal elements carry active chromatin. Neoplasia 2003;5(2):110-20.

Huang X, Yan J, Zhang M, Wang Y, Chen Y, Fu X, et al. Targeting Epigenetic Crosstalk as a Therapeutic Strategy for EZH2-Aberrant Solid Tumors. Cell 2018;175(1):186-99 e19 doi 10.1016/j.cell.2018.08.058.

Nukaga S, Yasuda H, Tsuchihara K, Hamamoto J, Masuzawa K, Kawada I, et al. Amplification of EGFR Wild-Type Alleles in Non-Small Cell Lung Cancer Cells Confers Acquired Resistance to Mutation-Selective EGFR Tyrosine Kinase Inhibitors. Cancer Res 2017;77(8):2078-89 doi 10.1158/0008-5472.CAN-16-2359.

Dobin A, Davis CA, Schlesinger F, Drenkow J, Zaleski C, Jha S, et al. STAR: ultrafast universal RNA-seq aligner. Bioinformatics 2013;29(1):15-21 doi 10.1093/bioinformatics/bts635.

Anders S, Pyl PT, Huber W. HTSeq—a Python framework to work with high-throughput sequencing data. Bioinformatics 2015;31(2):166-9 doi 10.1093/bioinformatics/btu638.

Robinson MD, McCarthy DJ, Smyth GK. edgeR: a Bioconductor package for differential expression analysis of digital gene expression data. Bioinformatics 2010;26(1):139-40 doi 10.1093/bioinformatics/btp616.

Li H, Durbin R. Fast and accurate long-read alignment with Burrows-Wheeler transform. Bioinformatics 2010;26(5):589-95 doi 10.1093/bioinformatics/btp698.

Ramirez F, Ryan DP, Gruning B, Bhardwaj V, Kilpert F, Richter AS, et al. deepTools2: a next generation web server for deep-sequencing data analysis. Nucleic Acids Res 2016;44(W1):W160-5 doi 10.1093/nar/gkw257.

Consortium EP. The ENCODE (ENCyclopedia Of DNA Elements) Project. Science 2004;306(5696):636-40 doi 10.1126/science.1105136.

Li H, Durbin R. Fast and accurate short read alignment with Burrows-Wheeler transform. Bioinformatics 2009;25(14):1754-60 doi 10.1093/bioinformatics/btp324.

Black et al. Hypoxia drives transient site-specific copy gain and drug-resistant gene expression, Genes & development. May 15, 2015, vol. 29, No. 10, pp. 1018-1031. p. 1026, col. 1, para 2-p. 1026. col 2. para 1; abstract.

Lin H, et al. Small molecule KDM4s inhibitors as anti-cancer agents. J Enzyme Inhib Med Chem. 2018;33(1):777-793. doi:10.1080/14756366.2018.1455676.

Kurmasheva et al. Initial testing (stage 1) of tazemetostat (EPZ]6438), a novel EZH2 inhibitor, by the Pediatric Preclinical Testing Program, Pediatric blood & cancer, Aug. 24, 2016, vol. 64, No. 3, article e26218. pp. 1-9.

Moroni et al. Gene copy number for epidermal growth factor receptor (EGFR) and clinical response to antiEGFR treatment in colorectal cancer: a cohort study. The Lancet Oncology, May 1, 2005, vol. 6, No. 5, pp. 279-286.

Yap TA, et al. A Phase I Study of GSK2816126, an Enhancer of Zeste Homolog 2(EZH2) Inhibitor, in Patients (pts) with Relapsed/Refractory Diffuse Large B-Cell Lymphoma (DLBCL), Other Non-Hodgkin Lymphomas (NHL), Transformed Follicular Lymphoma (tFL), Solid Tumors and Multiple Myeloma (MM). Blood 2016; 128 (22): 4203. doi: https://doi.org/10.1182/blood.V128.22.4203.4203.

Leadem BR, Kagiampakis I, Wilson C, et al. A KDM5 Inhibitor Increases Global H3K4 Trimethylation Occupancy and Enhances the Biological Efficacy of 5-Aza-2'-Deoxycytidine. Cancer Res. 2018;78(5):1127-1139. doi:10.1158/0008-5472.CAN-17-1453.

Yang GJ, Ko CN, Zhong HJ, Leung CH, Ma DL. Structure-Based Discovery of a Selective KDM5A Inhibitor that Exhibits Anti-Cancer Activity via Inducing Cell Cycle Arrest and Senescence in Breast Cancer Cell Lines. Cancers (Basel). 2019;11(1):92. Published Jan. 15, 2019. doi:10.3390/cancers11010092.

Honma D, Kanno O, Watanabe J, et al. Novel orally bioavailable EZH1/2 dual inhibitors with greater antitumor efficacy than an EZH2 selective inhibitor. Cancer Sci. 2017;108(10):2069-2078. doi:10.1111/cas.13326.

Duan, R., Du, W. & Guo, W. EZH2: a novel target for cancer treatment. J Hematol Oncol 13, 104 (2020). https://doi.org/10.1186/s13045-020-00937-8.

Yap TA, Winter JN, Giulino-Roth L, et al. Phase I Study of the Novel Enhancer of Zeste Homolog 2 (EZH2) Inhibitor GSK2816126 in Patients with Advanced Hematologic and Solid Tumors. Clin Cancer Res. 2019;25(24):7331-7339. doi:10.1158/1078-0432.CCR-18-4121.

International Patent Application No. PCT/US2020/060808, International Search Report and Written Opinion mailed on Feb. 19, 2021, 11 pages.

* cited by examiner

SEQUENCE LISTING

```
<160> NUMBER OF SEQ ID NOS: 75

<210> SEQ ID NO 1
<211> LENGTH: 21
<212> TYPE: DNA
<213> ORGANISM: Homo sapiens

<400> SEQUENCE: 1

gaauagguau uggugaauut t                                               21


<210> SEQ ID NO 2
<211> LENGTH: 21
<212> TYPE: DNA
<213> ORGANISM: Homo sapiens

<400> SEQUENCE: 2

ccauaaaugc uacgaauaut t                                               21


<210> SEQ ID NO 3
<211> LENGTH: 21
<212> TYPE: DNA
<213> ORGANISM: Homo sapiens

<400> SEQUENCE: 3

cuauggaaga guuccgaaat t                                               21


<210> SEQ ID NO 4
<211> LENGTH: 21
<212> TYPE: DNA
<213> ORGANISM: Homo sapiens

<400> SEQUENCE: 4

gcgacaaucu uuauccugat t                                               21


<210> SEQ ID NO 5
<211> LENGTH: 21
<212> TYPE: DNA
<213> ORGANISM: Homo sapiens

<400> SEQUENCE: 5

gcucuaacug aacaacuaat t                                               21


<210> SEQ ID NO 6
<211> LENGTH: 21
<212> TYPE: DNA
<213> ORGANISM: Homo sapiens

<400> SEQUENCE: 6

cgcugauuuu cgaguguaat t                                               21
```

<210> SEQ ID NO 7
<211> LENGTH: 21
<212> TYPE: DNA
<213> ORGANISM: Homo sapiens

<400> SEQUENCE: 7
cagcugcagu aucucggaat t 21

<210> SEQ ID NO 8
<211> LENGTH: 21
<212> TYPE: DNA
<213> ORGANISM: Homo sapiens

<400> SEQUENCE: 8
cucucaccgu uuccacaaat t 21

<210> SEQ ID NO 9
<211> LENGTH: 21
<212> TYPE: DNA
<213> ORGANISM: Homo sapiens

<400> SEQUENCE: 9
agaacagcuu cgucauggat t 21

<210> SEQ ID NO 10
<211> LENGTH: 21
<212> TYPE: DNA
<213> ORGANISM: Homo sapiens

<400> SEQUENCE: 10
caaaucgugu gguacagaat t 21

<210> SEQ ID NO 11
<211> LENGTH: 21
<212> TYPE: DNA
<213> ORGANISM: Homo sapiens

<400> SEQUENCE: 11
gaaugaguuu ugucauggat t 21

<210> SEQ ID NO 12
<211> LENGTH: 21
<212> TYPE: DNA
<213> ORGANISM: Homo sapiens

<400> SEQUENCE: 12
guauucgcuu ugcaucuuut t 21

<210> SEQ ID NO 13
<211> LENGTH: 21
<212> TYPE: DNA
<213> ORGANISM: Homo sapiens

<400> SEQUENCE: 13
ggacaaugca ggagauagat t 21

<210> SEQ ID NO 14
<211> LENGTH: 21
<212> TYPE: DNA
<213> ORGANISM: Homo sapiens

<400> SEQUENCE: 14
caaccagaca uauagaucat t 21

<210> SEQ ID NO 15
<211> LENGTH: 21
<212> TYPE: DNA
<213> ORGANISM: Homo sapiens

<400> SEQUENCE: 15
gcugaccauu gggacaguat t 21

<210> SEQ ID NO 16
<211> LENGTH: 21
<212> TYPE: DNA
<213> ORGANISM: Homo sapiens

<400> SEQUENCE: 16
guguaugagu uuagagucat t 21

<210> SEQ ID NO 17
<211> LENGTH: 21
<212> TYPE: DNA
<213> ORGANISM: Homo sapiens

<400> SEQUENCE: 17
ggaccgacau ugguguauat t 21

<210> SEQ ID NO 18
<211> LENGTH: 21
<212> TYPE: DNA
<213> ORGANISM: Homo sapiens

<400> SEQUENCE: 18
gcgaguuugu ugugacauut t 21

<210> SEQ ID NO 19
<211> LENGTH: 21
<212> TYPE: DNA
<213> ORGANISM: Homo sapiens

<400> SEQUENCE: 19
ggcaguaaag gaaaucgaat t 21

<210> SEQ ID NO 20
<211> LENGTH: 21
<212> TYPE: DNA
<213> ORGANISM: Homo sapiens

<400> SEQUENCE: 20
ggaagaucuu ggacuuauut t 21

<210> SEQ ID NO 21
<211> LENGTH: 21
<212> TYPE: DNA
<213> ORGANISM: Homo sapiens

<400> SEQUENCE: 21
cagacgagag ugaaacugat t 21

<210> SEQ ID NO 22
<211> LENGTH: 21
<212> TYPE: DNA
<213> ORGANISM: Homo sapiens

<400> SEQUENCE: 22
ggaguuacuc cauuaacuat t 21

<210> SEQ ID NO 23
<211> LENGTH: 21
<212> TYPE: DNA
<213> ORGANISM: Homo sapiens

<400> SEQUENCE: 23
cagagaagcu agaccugaat t 21

<210> SEQ ID NO 24
<211> LENGTH: 21
<212> TYPE: DNA
<213> ORGANISM: Homo sapiens

<400> SEQUENCE: 24
ggaguguaau aagugccgat t 21

<210> SEQ ID NO 25
<211> LENGTH: 21
<212> TYPE: DNA
<213> ORGANISM: Homo sapiens

<400> SEQUENCE: 25
gguugcuaua uguuccgaat t 21

<210> SEQ ID NO 26
<211> LENGTH: 21
<212> TYPE: DNA
<213> ORGANISM: Homo sapiens

<400> SEQUENCE: 26
caacgacuca aaguauauat t 21

<210> SEQ ID NO 27
<211> LENGTH: 21
<212> TYPE: DNA
<213> ORGANISM: Homo sapiens

<400> SEQUENCE: 27
cgcagugagu uugaacagat t 21

<210> SEQ ID NO 28
<211> LENGTH: 21
<212> TYPE: DNA
<213> ORGANISM: Homo sapiens

<400> SEQUENCE: 28
cguucaaggc ucaaccacat t 21

<210> SEQ ID NO 29
<211> LENGTH: 21
<212> TYPE: DNA
<213> ORGANISM: Homo sapiens

<400> SEQUENCE: 29
cgguggaaau ugucgaagat t 21

<210> SEQ ID NO 30
<211> LENGTH: 18
<212> TYPE: DNA
<213> ORGANISM: Homo sapiens

<400> SEQUENCE: 30
gcctcccacc ctatccaa 18

<210> SEQ ID NO 31
<211> LENGTH: 27
<212> TYPE: DNA
<213> ORGANISM: Homo sapiens

<400> SEQUENCE: 31
tcatccagtg tgtatacatc atctctc 27

<210> SEQ ID NO 32
<211> LENGTH: 18
<212> TYPE: DNA
<213> ORGANISM: Homo sapiens

<400> SEQUENCE: 32
ggcctcaagt gacgagga 18

<210> SEQ ID NO 33
<211> LENGTH: 20
<212> TYPE: DNA
<213> ORGANISM: Homo sapiens

<400> SEQUENCE: 33
cttccactgc agagacagca 20

<210> SEQ ID NO 34
<211> LENGTH: 19
<212> TYPE: DNA
<213> ORGANISM: Homo sapiens

<400> SEQUENCE: 34
agcagcagtg aagctgagg 19

<210> SEQ ID NO 35
<211> LENGTH: 24
<212> TYPE: DNA
<213> ORGANISM: Homo sapiens

<400> SEQUENCE: 35
tgtacttaag cagctgtttc ctga 24

<210> SEQ ID NO 36
<211> LENGTH: 18
<212> TYPE: DNA
<213> ORGANISM: Homo sapiens

<400> SEQUENCE: 36
aatggcagac gtggtcgt 18

<210> SEQ ID NO 37
<211> LENGTH: 19
<212> TYPE: DNA
<213> ORGANISM: Homo sapiens

<400> SEQUENCE: 37
tcttggctgg agtctggag 19

<210> SEQ ID NO 38
<211> LENGTH: 22
<212> TYPE: DNA
<213> ORGANISM: Homo sapiens

<400> SEQUENCE: 38
tcagcactga tacccaaact tc 22

<210> SEQ ID NO 39
<211> LENGTH: 23
<212> TYPE: DNA
<213> ORGANISM: Homo sapiens

<400> SEQUENCE: 39
tcacatctcc agattctgac tga 23

<210> SEQ ID NO 40
<211> LENGTH: 21
<212> TYPE: DNA
<213> ORGANISM: Homo sapiens

<400> SEQUENCE: 40
agcagactgg catctgtaag g 21

<210> SEQ ID NO 41
<211> LENGTH: 24
<212> TYPE: DNA
<213> ORGANISM: Homo sapiens

<400> SEQUENCE: 41
gaagtttatc aacatcacat gcaa 24

<210> SEQ ID NO 42
<211> LENGTH: 21
<212> TYPE: DNA
<213> ORGANISM: Homo sapiens

<400> SEQUENCE: 42
cgaacgcatt gtttatccct a 21

<210> SEQ ID NO 43
<211> LENGTH: 21
<212> TYPE: DNA
<213> ORGANISM: Homo sapiens

<400> SEQUENCE: 43
cgtgtgttac actgcacaag g 21

<210> SEQ ID NO 44
<211> LENGTH: 23
<212> TYPE: DNA
<213> ORGANISM: Homo sapiens

<400> SEQUENCE: 44
ctgcacaagt aaaagcaact gtc 23

<210> SEQ ID NO 45
<211> LENGTH: 26
<212> TYPE: DNA
<213> ORGANISM: Homo sapiens

<400> SEQUENCE: 45
cttttggaga tactgaatag catagc 26

<210> SEQ ID NO 46
<211> LENGTH: 19
<212> TYPE: DNA
<213> ORGANISM: Homo sapiens

<400> SEQUENCE: 46
accctcgaaa tcccatcac 19

<210> SEQ ID NO 47
<211> LENGTH: 18
<212> TYPE: DNA
<213> ORGANISM: Homo sapiens

<400> SEQUENCE: 47
gtgttcgcca ctcgcttc 18

<210> SEQ ID NO 48
<211> LENGTH: 23
<212> TYPE: DNA
<213> ORGANISM: Homo sapiens

<400> SEQUENCE: 48
gacagtgtgc gttatgtttg act 23

<210> SEQ ID NO 49
<211> LENGTH: 26
<212> TYPE: DNA
<213> ORGANISM: Homo sapiens

<400> SEQUENCE: 49
tggccaatat atatagtaaa cgacca 26

<210> SEQ ID NO 50
<211> LENGTH: 20
<212> TYPE: DNA
<213> ORGANISM: Homo sapiens

<400> SEQUENCE: 50
ggaggaagca gcaagcagta 20

<210> SEQ ID NO 51
<211> LENGTH: 19
<212> TYPE: DNA
<213> ORGANISM: Homo sapiens

<400> SEQUENCE: 51
gctcaggttt ggggattgt 19

<210> SEQ ID NO 52
<211> LENGTH: 21
<212> TYPE: DNA
<213> ORGANISM: Homo sapiens

<400> SEQUENCE: 52
ccacgaaaac aaagaggaca g 21

<210> SEQ ID NO 53
<211> LENGTH: 24
<212> TYPE: DNA
<213> ORGANISM: Homo sapiens

<400> SEQUENCE: 53
tgggtgctta cacttacaca agat 24

<210> SEQ ID NO 54
<211> LENGTH: 20
<212> TYPE: DNA

<213> ORGANISM: Homo sapiens

<400> SEQUENCE: 54
atcctggaga cacccatcag 20

<210> SEQ ID NO 55
<211> LENGTH: 19
<212> TYPE: DNA
<213> ORGANISM: Homo sapiens

<400> SEQUENCE: 55
gacaggctca gggtcagtg 19

<210> SEQ ID NO 56
<211> LENGTH: 20
<212> TYPE: DNA
<213> ORGANISM: Homo sapiens

<400> SEQUENCE: 56
gcggtcagag aacagctacc 20

<210> SEQ ID NO 57
<211> LENGTH: 20
<212> TYPE: DNA
<213> ORGANISM: Homo sapiens

<400> SEQUENCE: 57
ggaggctgaa gatgcagaga 20

<210> SEQ ID NO 58
<211> LENGTH: 19
<212> TYPE: DNA
<213> ORGANISM: Homo sapiens

<400> SEQUENCE: 58
caagttcacg gacgcctac 19

<210> SEQ ID NO 59
<211> LENGTH: 18
<212> TYPE: DNA
<213> ORGANISM: Homo sapiens

<400> SEQUENCE: 59
ccgcgggaga attgtgta 18

<210> SEQ ID NO 60
<211> LENGTH: 20
<212> TYPE: DNA
<213> ORGANISM: Homo sapiens

<400> SEQUENCE: 60
tgggaaaggt gacctcagat 20

<210> SEQ ID NO 61
<211> LENGTH: 21
<212> TYPE: DNA
<213> ORGANISM: Homo sapiens

<400> SEQUENCE: 61
gggcagaacc taactcctct g 21

<210> SEQ ID NO 62
<211> LENGTH: 20

<212> TYPE: DNA
<213> ORGANISM: Homo sapiens

<400> SEQUENCE: 62
gccaaagagg tgacgatagc 20

<210> SEQ ID NO 63
<211> LENGTH: 18
<212> TYPE: DNA
<213> ORGANISM: Homo sapiens

<400> SEQUENCE: 63
actgcccgtt gtggtgtc 18

<210> SEQ ID NO 64
<211> LENGTH: 21
<212> TYPE: DNA
<213> ORGANISM: Homo sapiens

<400> SEQUENCE: 64
gtcatggagt acgtgggaga g 21

<210> SEQ ID NO 65
<211> LENGTH: 20
<212> TYPE: DNA
<213> ORGANISM: Homo sapiens

<400> SEQUENCE: 65
cctgacggtc gtagatctgg 20

<210> SEQ ID NO 66
<211> LENGTH: 23
<212> TYPE: DNA
<213> ORGANISM: Homo sapiens

<400> SEQUENCE: 66
tctttcaaaa atgttgtcct gct 23

<210> SEQ ID NO 67
<211> LENGTH: 22
<212> TYPE: DNA
<213> ORGANISM: Homo sapiens

<400> SEQUENCE: 67
aggtgggatt ttaatttgtt gg 22

<210> SEQ ID NO 68
<211> LENGTH: 19
<212> TYPE: DNA
<213> ORGANISM: Homo sapiens

<400> SEQUENCE: 68
gcttcccctt ccctctttc 19

<210> SEQ ID NO 69
<211> LENGTH: 21
<212> TYPE: DNA
<213> ORGANISM: Homo sapiens

<400> SEQUENCE: 69
gggaagacat gcttttgtcc t 21

<210> SEQ ID NO 70

-continued

```
<211> LENGTH: 22
<212> TYPE: DNA
<213> ORGANISM: Homo sapiens

<400> SEQUENCE: 70

tgggaccaaa acatgtagac ag                                    22


<210> SEQ ID NO 71
<211> LENGTH: 21
<212> TYPE: DNA
<213> ORGANISM: Homo sapiens

<400> SEQUENCE: 71

ttccttggag gagtatccac a                                     21


<210> SEQ ID NO 72
<211> LENGTH: 21
<212> TYPE: DNA
<213> ORGANISM: Homo sapiens

<400> SEQUENCE: 72

gatacagctc agaccccaca g                                     21


<210> SEQ ID NO 73
<211> LENGTH: 19
<212> TYPE: DNA
<213> ORGANISM: Homo sapiens

<400> SEQUENCE: 73

ttttgggaac ggactggtt                                        19


<210> SEQ ID NO 74
<211> LENGTH: 17
<212> TYPE: DNA
<213> ORGANISM: Homo sapiens

<400> SEQUENCE: 74

aggccaaccg cgagaag                                          17


<210> SEQ ID NO 75
<211> LENGTH: 23
<212> TYPE: DNA
<213> ORGANISM: Homo sapiens

<400> SEQUENCE: 75

acagcctgga tagcaacgta cat                                   23
```

COMPOSITIONS AND METHODS FOR REGULATING EGFR AMPLIFICATION IN CANCER CELLS FOR IMPROVING EFFICACY OF EGFR-TARGETED ANTI-CANCER AGENTS

CROSS-REFERENCE TO RELATED APPLICATION

This application is a Continuation-in-part of International Application No. PCT/US2020/060808, filed Nov. 16, 2020, which claims priority to U.S. Provisional Application No. 62/935,763, filed on Nov. 15, 2019, the entire disclosure of each being incorporated herein by reference as though set forth in full.

Incorporation by Reference of Material Submitted in Electronic Form Applicant hereby incorporates by reference the Sequence Listing material filed in electronic form herewith. This file is labelled "SEQLIST.txt" dated May 13, 2022 and is 11,518 bytes in size.

FIELD OF THE INVENTION

The present invention relates to various compositions and methods for regulating EGFR amplification in cancer in order to sensitize tumor cells to EGFR-targeted anti-cancer agents.

BACKGROUND OF THE INVENTION

Several publications and patent documents are cited throughout the specification in order to describe the state of the art to which this invention pertains. Each of these citations is incorporated herein by reference as though set forth in full.

Chromosomal instability is a hallmark of cancer cells (1). These abnormalities can include entire chromosome events or they can be localized to site-specific chromosomal regions (2). For example, the chromosome 1l2-25 (1l2-25) region is regularly amplified in tumors (3-9). This amplification event is often associated with drug resistance as a number of genes (e.g., MCL1, CKS1B which confer drug resistance) reside within this chromosomal region (3-9). Amplification of these regions can occur as frequently as the well documented oncogene amplifications MYC and epidermal growth factor receptor (EGFR) in certain tumor types (e.g., 1921.3 at 21% versus MYC at 26% in liver cancer; (10)). However, it is important to note that amplifications are not always permanently integrated (2). A recent study estimated that approximately 50% of tumors contain extrachromosomal DNA (ecDNA) amplifications for the EGFR and MYC genes (11).

The extrachromosomal nature of these copy gains provides the cell an opportunity to either select for or against these amplifications, which will impact cell growth and drug response. For example, extrachromosomal amplification of EGFR results in increased sensitivity to targeted therapies. However, following prolonged treatment with an EGFR inhibitor, the ecDNA copies of EGFR are reduced, leading to therapy resistance (12). In the case of methotrexate therapy, the dihydrofolate reductase (DHFR) gene is amplified and provides resistance (13-16). DHFR amplifications can occur as integrated and/or extrachromosomal events (13-16).

It is clear that extrachromosomal amplifications promote tumor heterogeneity and tumor adaptation, both of which are major contributors to drug resistance (2,11). Elucidating the cellular physiology and molecular mechanisms that promote oncogene-associated extrachromosomal events should have a profound impact on our understanding of tumor heterogeneity and drug resistance.

The molecular mechanisms underlying extrachromosomal amplification events are still poorly understood; however, recent studies have demonstrated a critical role for epigenetic states and chromatin modifying enzymes in controlling site-specific re-replication, and in turn, DNA copy number amplification (10,17-19). For example, overexpression or stabilization of the H3K9/36 tri-demethylase KDM4A, and the direct modulation of chromatin states (H3K9 and K36 methylation) promotes transient site-specific DNA copy gains (TSSGs) within the Chr1q12-21 region (17-20). These DNA copy gains are transiently generated during S phase and are lost in late S or early G2 phase of the cell cycle (18). Indeed, KDM4A interacts with components of the replication machinery, facilitating re-replication at the TSSG sites (18).

EGFR DNA amplification tends to result in poor prognosis for patients with EGFR-amplified cancer (22). EGFR-targeted therapies have been developed in recent years (23) and EGFR amplifications have been shown to associate with varying degrees of patient response across various amplified tumors (24-29). EGFR DNA amplification is prevalent across a number of different cancer types, with up to 54% of patients exhibiting amplification in some tumor types (e.g., glioblastoma multiforme) (10). An important clinical challenge with EGFR amplification is the plasticity of the amplification (12). Therefore, there is a major clinical need to resolve the mechanisms driving EGFR amplification in order to generate effective therapeutic strategies to treat these aggressive cancers.

SUMMARY OF THE INVENTION

In accordance with the present invention, a method for treating a subject having an EGFR inhibitor (EGFRi) resistant tumor is provided. In one aspect, the method entails determining EGFR copy number in cells obtained from said tumor, contacting the cells with an agent that modulates amplification of EGFR to a level which sensitizes said cells to EGFR inhibitors; and administering to the subject an EGFRi, thereby reducing tumor cell proliferation or inducing tumor cell killing which exceeds that observed in tumor cells not treated with the EGFR amplification modulation agent. In certain embodiments, copy number is determined using DNA FISH. In a preferred embodiment, the EGFR copy number is determined to be high and said tumor cells are contacted with at least one inhibitor selected from EZH2 inhibitor, KDM5 inhibitor and KDM5A inhibitor which further increases EGFR amplification and sensitivity of said cells to EGFRi. In certain embodiments, the inhibitor inhibits EZH2. In other embodiments, the inhibitor is tazemetostat. The cells to be treated can be diploid for EGFR copies. The cells can have an EGFR copy number of between 3-7. In other aspects, the tumor cells have a copy number of EGFR of 8 or higher. In other embodiments, the cells exhibit a loss of heterozygosity in the EGFR region and the inhibitor is an EZH2 inhibitor. The tumor cells can also be contacted with at least one histone lysine methyltransferase (KMT), thereby increasing EGFR copy number and rendering the tumor more sensitive to EGFR inhibitors. The KMT can be selected from KMT2A, SETD1A and SETD1B. In other embodiments, the method includes administration of at least one EGFR inhibitor selected from gefitinib, erlotinib, lapatinib, cetuximab, osimertinib, panitumumab, neratinib, vandetanib, necitumumab, and dacomitinib. In preferred embodiments, the at least one EGFR inhibitor is selected from gefinitnib or lapatnib.

In yet another aspect, the modulation of EGFR amplification reduces tumor heterogeneity. An exemplary method for reducing tumor heterogeneity in a subject in need thereof, in order to sensitize the tumor to EGFRi therapy, comprises reducing EGFR amplification levels via administration at least one KDM4 inhibitor and treating said tumor with an EGFR inhibitor. In certain cases, the tumor cells are hypoxic. The method can further comprise determining EGFR amplification levels prior to KDM4 inhibitor administration step. In other aspects of the methods, methylase and demethylase expression levels in the tumor are determined at protein and RNA levels. The inhibitors of the invention are administered in a pharmaceutically acceptable carrier via route selected from the group consisting of systemic, oral, intraperitoneal, intravenous, intracerebral, intratumoral and topical administration. Preferred routes of administration include systemic and oral administration.

BRIEF DESCRIPTION OF THE DRAWINGS

FIG. 1A) Scatter plot comparing EGFR gene expression (Y-axis) to EGFR DNA copy number (X-axis) from the pancancer TCGA data set (7069 patients spanning 21 tumor types). Expression is shown in units of transcripts per million (TPM), converted to log 2 values. Copy number is shown as number of copies. FIG. 1B) Representative DNA FISH images of RPE nuclei from cells transduced with H3.3 Wild Type (H3.3 WT), K4M, K9M, K27M or K36M variants. EGFR (red), DAPI (blue) and merge are shown. FIG. 1C) RPE cells transduced with H3.3 K9M or H3.3 K27M variants exhibit EGFR copy gains. FIG. 1D) RPE cells transduced with H3.3 K9M or H3.3 K27M variants do not exhibit 7p tel copy gains. FIG. 1E) RPE cells transduced with H3.3 K9M or H3.3 K27M variants do not exhibit IKZF1 copy gains. FIG. 1F) Representative DNA FISH images of RPE nuclei from cells transduced with H3.3 K9M or K27M variants with more than 4 DNA copies of EGFR (red) are shown. FIG. 1G) RPE cells transduced with H3.3 K9M or H3.3 K27M variants have a higher percentage of cells with 3 to 4 copies and 5 or more copies of EGFR DNA. FIG. 1H) RPE cells transduced with H3.3 K9M or H3.3 K27M variants have an increase in EGFR transcripts compared to H3.3 wild type-transduced cells, as measured by quantitative polymerase chain reaction (qPCR). FIG. 1I) Input-normalized ChIP-seq tracks of H3K36me3, H3K27me3 an H3K9me3 density in the megabase vicinity of the EGFR gene, aligned with the Hi-C map of chromatin interactions. FIG. 1J-1L) Input-normalized ChIP-seq tracks of H3K36me3, H3K27me3 an H3K9me3 density in the megabase vicinity of the EGFR gene, aligned with the Hi-C map of chromatin interactions in human HMEC (FIG. 1J) and K562 (FIG. 1L) cells as well as mouse B-lymphoblasts (CH12-LX) (FIG. 1L) (34,35). FIG. 1M) H3K27me3 ChIP-seq enrichment tracks from (36) in the vicinity of the EGFR gene in wild type and K27M-expressing 293 T-REx cells. Error bars represents S.E.M. The * represents p=<0.05 by two-tailed Student's t-test. The arrowheads mark DNA FISH foci. The scale bars are 5 μm.

FIG. 2A) Immunoblots for RPE whole cell extracts (WCEs) verifying expression of flag-tagged histone H3.3 constructs. FIG. 2B) Cell cycle analysis of RPE cells expressing histone H3.3 variants 48 hours after virus transduction. FIG. 2C) Representative DNA FISH images of RPE nuclei from cells transduced with H3.3 Wild Type (H3.3 WT), K4M, K9M, K27M or K36M variants. 7p Tel (red) and DAPI (blue) are shown in the merge. FIG. 2D) Representative DNA FISH images of RPE nuclei from cells transduced with H3.3 Wild Type (H3.3 WT), K4M, K9M, K27M or K36M variants. IKZF1 (red) and DAPI (blue) are shown in the merge. Error bars represents S.E.M. The * represents p=<0.05 by two-tailed Student's t-test.

FIG. 3A-D) qRT-PCR validating expression of KDM4 family members normalized to β-Actin. FIG. 3E) Immunoblots for RPE WCE verifying GFP-tagged KDM4 family members expression 24 hours post DNA transfection. β-Actin immunoblot was performed as a loading control. FIG. 3F) Cell cycle analysis of RPE cells expressing different GFP-tagged KDM4 family members from FIG. 3E. FIG. 3G) α-KDM4A immunoblot analysis validating protein expression of GFP-tagged KDM4A wild type or mutant constructs after 24 hours of DNA transfection. β-Actin immunoblot was performed as a loading control. FIG. 3H) Cell cycle analysis of RPE cells expressing GFP-tagged KDM4A wild type or KDM4A mutant constructs from FIG. 3G. FIG. 3I) Neither transient over expression of GFP-tagged KDM4A nor does H3.3 K-M transduction promote 7p Tel copy number gains in RPE cells. FIG. 3J) α-KDM4A immunoblot demonstrating stable overexpression of KDM4A in RPE cells. β-Actin immunoblot was performed as a loading control. FIG. 3K) Cell cycle analysis of control and stable GFP-KDM4A-overexpressing RPE cells. FIG. 3L) Representative bright field microscopy images of scratch assays performed in control or KDM4A over-expressing RPE cells. Cells were treated with 50 ng/ml EGF immediately after the scratch. 0 hr and 24 hr time points are shown. Images taken at 4× magnification on the EVOS microscope. Scale bar represents 500 um. FIG. 3M) qRT-PCR analysis of control or stable KDM4A expressing RPE cells treated with non-targeted siRNA (siCTRL) or EGFR siRNA (siEGFR). Cells were harvested 48 hours post siRNA transfection. Knockdown represents the relative knockdown of cells upon EGF treatment (FIG. 4K). Error bars represents S.E.M. The * represents p=<0.05 by two-tailed Student's t-test.

FIG. 4A) Transient over expression of GFP-tagged KDM4A drives EGFR copy number gain in RPE cells. FIG. 4B) Catalytic activity of KDM4A and the Tudor domains are required for EGFR copy gains. FIG. 4C) Representative DNA FISH image of a stable KDM4A overexpressing RPE nucleus with EGFR DNA copy number gain (red). FIG. 4D) RPE cells with stable KDM4A over-expression have increased EGFR DNA copies. FIG. 4E) Upper panel: Analysis of publicly available ChIP-sequencing data reveals that KDM4A is recruited to the EGFR locus (40). Lower panel: RNA sequencing analysis showed increased EGFR transcripts in RPE cells stably overexpressing KDM4A. FIG. 4F) KDM4A overexpressing RPE cells have increased EGFR transcripts as measured by qPCR. FIG. 4G) KDM4A overexpressing RPE cells have increased sensitivity to the EGFR-family inhibitor, Lapatinib, as measured by trypan blue exclusion assay. FIG. 4H) KDM4A overexpressing RPE cells have a dose-dependent increase in sensitivity to the specific EGFR inhibitor, Gefitinib, as measured by trypan blue exclusion assay. FIG. 4I) KDM4A overexpressing RPE cells migrate faster following 24 hours of 50 ng/ml EGF stimulation as measured by scratch assays. FIG. 4J) KDM4A overexpressing RPE cells proliferate faster in response to a 48 hour treatment with 50 ng/ml EGF. FIG. 4K) siRNA-mediated depletion of EGFR prevents increased EGF-stimulated (50 ng/ml) cell growth in KDM4A overexpressing RPE cells. Error bars represents S.E.M. The * represents p=<0.05 by two-tailed Student's t-test. The arrowheads mark DNA FISH foci. The scale bars are 5 um.

FIG. 5A) Representative DNA FISH images of HCC827 lung cancer cells, treated with either siRNA control or siRNA targeted to KDM4A. EGFR (red), DAPI (blue) and merge are shown. FIG. 5B) siRNA-mediated depletion of KDM4A (red), reduces the size of EGFR amplified gene cluster clouds in HCC827 lung cancer cells. FIG. 5C) Representative DNA FISH images of HCC827 lung cancer cells, treated with either DMSO or a KDM4 family inhibitor. EGFR (red), DAPI (blue) and merge are shown. FIG. 5D) Inhibition of KDM4 family (red) reduces the size of EGFR amplified gene cluster clouds in HCC827 lung cancer cells. FIG. 5E) KDM4 family inhibitor treatment reduces the efficacy of the EGFR inhibitor, Gefitinib, in HCC827 lung cancer cells (right panel).

FIG. 6A) qRT-PCR analysis of HCC827 lung cancer cells treated with siControl or siKDM4A. Cells were harvested 72 hours post siRNA transfection. KDM4A transcript levels are normalized to β-Actin. FIG. 6B) Representative α-KDM4A immunoblot of HCC827 lung cancer cells treated with siControl or siKDM4A. Cells were harvested 72 hours post siRNA transfection. β-Actin immunoblot was performed as a loading control. Error bars represents S.E.M. The * represents p=<0.05 by two-tailed Student's t-test.

FIG. 7A-7E) qRT-PCR analysis of H3K9 KMT transcripts in RPE cells treated with siControl or siRNAs targeting the indicated H3K9 KMT. Cells were harvested 72 hours post siRNA transfection. Transcript levels are normalized to β-Actin. FIG. 7T) Quantitative real time PCR analysis of RPE cells treated with siKDM5A, siEZH2 or siEGFR. Cells were treated with individual siRNAs or siRNAs targeting KDM5A or EZH2 with EGFR. Cells were harvested 48 hours post siRNA transfection and transcript levels reflect the relative siRNA-mediated knockdowns upon EGF treatment (FIGS. 8K and 9T). Error bars represents S.E.M. The * represents p=<0.05 by two-tailed Student's t-test.

FIG. 8A) DNA FISH analysis of EGFR (red), 7c (black) and 8c (grey) following siRNA-mediated depletion of K9 KMT family members. FIG. 8B) Input-normalized ChIP-seq tracks of H3K9mel-3, H3K4mel-3, H3K27me3 (34) and EZH2 (50) density in the megabase vicinity of the EGFR gene, aligned with the Hi-C map of chromatin interactions. FIG. 8C) EZH2 depletion promotes EGFR DNA copy gains that are KDM4A-dependent. FIG. 8D) Representative DNA FISH images of RPE nuclei from cells treated with DMSO, 1 μM EZH2i (EZH2i Gain) or 3 μM EZH2i (EZH2i Amp). EGFR (red) and DAPI (blue) are shown. FIG. 4E) EGFR DNA copy gains occur in a dose-dependent manner in response to EZH2 inhibitor (1, 3 and 5 μM) treatment. FIG. 8F) EGFR copy number gains returned to baseline 24 hours after EZH2 inhibitor (3 μM) drug removal (+ washout). FIG. 8G) RPE cells have increased EGFR transcripts following 24 hours of EZH2i treatment at higher doses (3 and 5 μM), as measured by qPCR. FIG. 8H) Spike-in normalized H3K27me3 ChIP-seq data from previously published dataset (44). PC9 cells were treated for 5 days with EZH2 inhibitor GSK126. FIG. 8I) Transient overexpression of the K27 tri-demethylases, KDM6A and KDM6B, promoted EGFR DNA copy gains in RPE cells. FIG. 8J) RPE cells pre-treated for 24 hours with 3 μM of EZH2i proliferate faster upon stimulation with 50 ng/ml EGF. FIG. 8K) siRNA-mediated depletion of EZH2 caused increased cell proliferation in response to 50 ng/ml EGF, which is completely rescued by co-depletion with EGFR in RPE cells. Error bars represents S.E.M. The * represents p=<0.05 by two-tailed Student's t-test. The arrowheads mark DNA FISH foci. The scale bars are Sum.

FIG. 9A) RPE cells transduced with H3.3 K4M completely inhibit EZH2i-mediated DNA copy gains of EGFR. FIG. 9U) Co-treatment of RPE cells with KDM5i (1 μM) and Gefitinib (2.5 μM) reduced the percentage of cells relative to controls and single agent treatment as measured by trypan blue exclusion assay. Error bars represents S.E.M. The * represents p=<0.05 by two-tailed Student's t-test. The arrowheads mark DNA FISH foci. The scale bars are 5 μm.

FIG. 10A) Immunoblot analysis of whole cell extracts from RPE cells treated with EZH2i that verify expression of flag-tagged histone H3.3 wild type of K4M constructs. β-Actin was used as a loading control. FIG. 10V) qRT-PCR analysis of RPE cells treated with siRNAs targeted to KDM5A or EGFR, alone or in combination prior to EGF treatment (FIG. 9T). Cells were harvested 48 hours post siRNA transfection and transcripts; therefore, the data reflects the relative gene knockdown upon EGF treatment. Error bars represents S.E.M. The * represents p=<0.05 by two-tailed Student's t-test.

FIG. 11A) KDM4A protein levels increase in RPE cells after being cultured in hypoxia (1% O2) for 24 hours. FIG. 11B) RPE cells cultured in hypoxia for 24 hours have increased EGFR copy gains. FIG. 11C) KDM4A protein levels increased with hypoxia (1% $O_2$ for 24 hours) and are depleted with siKDM4A. FIG. 11D) Hypoxia induced EGFR DNA copy gains in a KDM4A-dependent manner. FIG. 11E) Representative EGFR DNA FISH images of RPE nuclei from cells treated with normoxia (24 and 48 hours), hypoxia (24 hours) or hypoxia (24 hours) shifted to normoxia (24 hours). EGFR (red) and DAPI (blue) are shown in the merge. FIG. 11F) Hypoxia induced EGFR DNA copy gains are rescued with a shift to normoxia. FIG. 11G) A 24 hour pre-treatment of RPE cells with KDM4i (1 nM) completely blocks hypoxia-induced EGFR amplification. FIG. 11H) RPE cells transduced with H3.3 K4M do not exhibit EGFR DNA copy gains when cultured in hypoxia for 24 hours. FIG. 11I) RPE cells treated with 50 ng/ml EGF for 24 hours exhibit EGFR amplification that are KDM4A-dependent. FIG. 11J) A 24 hour pre-treatment of RPE cells with KDM4i (1 nM) completely blocks EGF-induced EGFR DNA copy gains. FIG. 11K) 50 ng/ml EGF for 24 hours increased EGFR transcripts in RPE cells, which was partially KDM4-dependent. FIG. 11L) Following 24 hour stimulation with 50 ng/ml EGF, RPE cells transduced with H3.3 K4M do not exhibit increases in EGFR DNA copy number. FIG. 11M siRNA-mediated depletion of KMT2A and SETD1A blocks EGF-induced EGFR DNA copy gains.

FIG. 12A) Cell cycle analysis of RPE cells cultured in normoxia or hypoxia (1% O2) for 24 hours.

12H) qRT-PCR analysis of RPE cells treated with siRNAs targeted to KDM4A. 48 hours post siRNA transfection, cells were treated with 50 ng/ml EGF for 24 hours. FIG. 12O) A model depicting the impact hypoxia/KDM4A and EGF/KMT2 (MLL1/SETD1A,B) have on promoting EGFR copy gains through KDM4A and H3K4 methylation. The suppression of hypoxia and EGF promoted EGFR copy gains are noted with KDM4i and H3.3 K4M transduction. The model is based on the genetic experiments in FIG. 1I. Error bars represents S.E.M. The * represents p=<0.05 by two-tailed Student's t-test.

FIG. 13A) RPE cells cultured in hypoxia (24 hours) and then treated for 24 hours with 50 ng/ml EGF in continued hypoxia promoted higher percentage of cells with EGFR copy gains. FIG. 13B) Representative DNA FISH images of RPE nuclei from cells treated with hypoxia, EGF or a combination of hypoxia and EGF. EGFR (red), DAPI (blue) and merge are shown. FIG. 13C) Graph illustrating the % of cells with >4 and >5 EGFR DNA copies from FIG. 13A. FIG. 13D) RPE cells stably overexpressing KDM4A exhibit additive increases in EGFR DNA copy number when stimulated with 50 ng/ml EGF for 24 hours. FIG. 13E) Graph illustrating the % of cells with >4 and >5 EGFR DNA copies from FIG. 13D. FIG. 13F) Representative DNA FISH images of higher EGFR DNA copies in KDM4A overexpressing cells treated with 50 ng/ml EGF for 24 hours. EGFR (red), DAPI (blue) and merge are shown. Error bars represents S.E.M. The * represents p=<0.05 by two-tailed Student's t-test. The arrowheads mark DNA FISH foci. The scale bars are 5 um.

FIG. 14A) Cell cycle analysis of RPE cells treated with 50 ng/ml EGF for 24 hours, followed by transfer to hypoxic culture conditions (1% $O_2$) for an additional 24 hours. FIG. 14B) Cell cycle analysis of KDM4A stable overexpression RPE cells treated with 50 ng/ml EGF for 48 hours. FIG. 14C) Immunoblot analysis of KDM4A protein levels from two independent experiments following EGF treatment (50 ng/ml) for 24 hours. FIG. 14D) Cell cycle analysis of RPE cells pre-treated with a KDM5i (1 μM) for 24 hours followed by transfer to hypoxic culture conditions (1% O2) for an additional 24 hours. FIG. 14E) DNA FISH analysis of cells in FIG. 14D. FIG. 14F) Graph illustrating the percentage of the total cell population with >4 and >5 EGFR DNA copies from FIG. 14E. FIG. 14G) Cell cycle analysis of RPE cells pre-treated with a EZH2i (3 μM) for 24 hours followed by transfer to hypoxic culture conditions (1% O2) for an additional 24 hours. FIG. 14H) DNA FISH analysis for cells in FIG. 14G. FIG. 14I) Graph illustrating the percentage of the total cell population with >4 and >5 EGFR DNA copies from FIG. 14H. Error bars represents S.E.M. The * represents p=<0.05 by two-tailed Student's t-test.

(FIG. 16A). Tumors with heterogenous EGFR levels (e.g. tumors with copy numbers across the arrow) require treatment to reduce heterogeneity prior to treatment with EGFRi. (FIG. 16B)

DETAILED DESCRIPTION

Figure 1A:
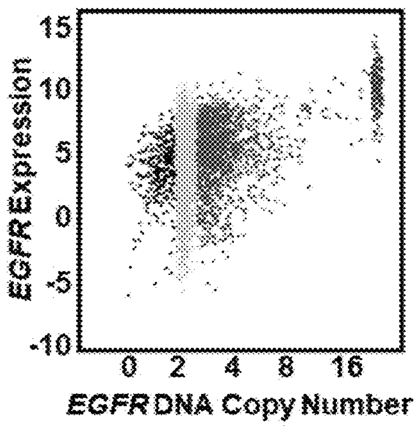
FIG. 1A-1M: H3K9/27 methylation controls EGFR amplification.

Acquired chromosomal DNA copy gains are a feature of many tumors; however, the mechanisms that underpin oncogene amplification are poorly understood. Recent studies have begun to uncover the importance of epigenetic states and histone lysine methyltransferases (KMTs) and demethylases (KDMs) in regulating transient site-specific DNA copy number gains (TSSGs). We have revealed a critical interplay between a myriad of lysine methyltransferases and demethylases in modulating H3K4/9/27 methylation balance in order to control extrachromosomal amplification of the EGFR oncogene. Further, we establish that cellular signals (hypoxia and epidermal growth factor) are able to directly promote EGFR amplification through modulation of the enzymes controlling EGFR copy gains. Moreover, we demonstrate that chemical inhibitors targeting specific KMTs and KDMs are able to promote or block extrachromosomal EGFR amplification, which identifies useful therapeutic strategies for controlling EGFR copy number heterogeneity in cancer, and in turn, drug response.

We demonstrate that chromatin modifying enzymes and their associated epigenetic states control amplification of the EGFR locus. Specifically, we demonstrate that directly interfering with H3K9 and H3K27 methylation promotes EGFR amplification. Furthermore, we establish a critical interplay between H3K4/9/27 lysine methyltransferases and demethylases in either promoting or blocking EGFR amplification. For example, KDM4A overexpression promotes EGFR copy gains in conjunction with three H3K4 methyltransferases: KMT2A/MLL1, SETD1A and SETD1B. In addition, we demonstrate that suppression of specific H3K9 KMTs and the H3K27 KMT EZH2 generates EGFR amplification. Consistent with these genetic experiments, we demonstrate for the first time that chemical inhibitors targeting KMT-KDMs are able to rheostat EGFR copy number, and in turn, growth factor and EGFR inhibitor responses. Lastly, we demonstrate that extrinsic cellular cues, such as hypoxia and Epidermal Growth Factor (EGF), promote EGFR amplification by modulating the KMT-KDM network that controls EGFR copy number. Taken together, this data uncovers both chromatin modifiers and extracellular signals that control EGFR amplification and demonstrate that epigenetic therapies could hold a key to modulating EGFR copy number heterogeneity in cancer, which has significant clinical implications.

I. Definitions

The following definitions are provided to facilitate an understanding of the present invention. Unless defined otherwise, all technical and scientific terms used herein have the same meaning as commonly understood by one of ordinary skill in the art to which this invention belongs. Generally, conventional methods of molecular biology, microbiology, recombinant DNA techniques, cell biology, and virology within the skill of the art are employed in the present invention. Such techniques are explained fully in the literature, see, e.g., Maniatis, Fritsch & Sambrook, Molecular Cloning: A Laboratory Manual (1982); DNA Cloning: A Practical Approach, Volumes I and II (D. N. Glover, ed. 1985); Oligonucleotide Synthesis (M. J. Gait, ed. 1984); Nucleic Acid Hybridization (B. D. Hames & S. J. Higgins, eds. (1984)); Animal Cell Culture (R. I. Freshney, ed. 1986); and RNA Viruses: A Practical Approach, (Alan, J. Cann, Ed., Oxford University Press, 2000).

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the functional and novel characteristics of the sequence.

A "derivative" of a polypeptide, polynucleotide or fragments thereof means a sequence modified by varying the sequence of the construct, e.g. by manipulation of the nucleic acid encoding the protein or by altering the protein itself. "Derivatives" of a gene or nucleotide sequence refers to any isolated nucleic acid molecule that contains significant sequence similarity to the gene or nucleotide sequence or a part thereof. In addition, "derivatives" include such isolated nucleic acids containing modified nucleotides or mimetics of naturally-occurring nucleotides.

The term "functional" as used herein implies that the nucleic or amino acid sequence is functional for the recited assay or purpose.

For purposes of the invention, "Nucleic acid", "nucleotide sequence" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. Alternatively, this term may refer to a DNA that has been sufficiently separated from (e.g., substantially free of) other cellular components with which it would naturally be associated. "Isolated" is not meant to exclude artificial or synthetic mixtures with other compounds or materials, or the presence of impurities that do not interfere with the fundamental activity, and that may be present, for example, due to incomplete purification. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

According to the present invention, an isolated or biologically pure molecule or cell is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

The terms "extrachromosomal DNA" or "ecDNA" refer to any DNA that is found off the chromosomes, either inside or outside the nucleus. Multiple forms of ecDNA exist and can play an important role in diseases such as cancer. ecDNA has been identified in the nuclei of various cancer cells and has been shown to carry many copies of driver oncogenes. ecDNA is considered to be a primary mechanism of gene amplification, resulting in many copies of driver oncogenes and very aggressive cancers.

The terms "miRNA" and "microRNA" refer to about 10-35 nt, preferably about 15-30 nt, and more preferably about 19-26 nt, non-coding RNAs derived from endogenous genes encoded in the genomes of plants and animals. They are processed from longer hairpin-like precursors termed pre-miRNAs that are often hundreds of nucleotides in length. MicroRNAs assemble in complexes termed miRNPs and recognize their targets by antisense complementarity. These highly conserved, endogenously expressed RNAs are believed to regulate the expression of genes by binding to the 3'-untranslated regions (3'-UTR) of specific mRNAs as well as other regions on targeted mRNAs. Without being bound by theory, a possible mechanism of action assumes that if the microRNAs match 100% their target, i.e. the complementarity is complete, the target mRNA is cleaved, and the miRNA acts like a siRNA. However, if the match is incomplete, i.e. the complementarity is partial, then the translation of the target mRNA is blocked. The manner by which a miRNA base-pairs with its mRNA target correlates with its function: if the complementarity between a mRNA and its target is extensive, the RNA target is cleaved; if the complementarity is partial, the stability of the target mRNA in not affected but its translation is repressed.

The term "RNA interference" or "RNAi" refers generally to a process or system in which a RNA molecule changes the expression of a nucleic acid sequence with which RNA molecule shares substantial or total homology. The term "RNAi agent" refers to an RNA sequence that elicits RNAi.

An "siRNA" refers to a molecule involved in the RNA interference process for a sequence-specific post-transcriptional gene silencing or gene knockdown by providing small interfering RNAs (siRNAs) that has homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

A "small nucleic acid inhibitor" refers to any sequence based nucleic acid molecule which, when introduced into a cell expressing the target nucleic acid, is capable of modulating expression of that target. siRNA, antisense, miRNA, shRNA and the like may be utilized in the methods of the invention.

The term "delivery" as used herein refers to the introduction of foreign molecule (i.e., miRNA containing nanoparticle) into cells. The term "administration" as used herein means the introduction of a foreign molecule into a cell. The term is intended to be synonymous with the term "delivery".

As used herein, the phrase "effective amount" of a compound or pharmaceutical composition refers to an amount sufficient to modulate tumor growth or metastasis in an animal, especially a human, including without limitation decreasing tumor growth or size or preventing formation of tumor growth in an animal lacking any tumor formation prior to administration, i.e., prophylactic administration.

Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers, for example to a diluent, adjuvant, excipient, auxiliary agent or vehicle with which an active agent of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

A pharmaceutical composition of the present invention can be administered by any suitable route, for example, by injection, by oral, pulmonary, nasal or other forms of administration. In general, pharmaceutical compositions contemplated to be within the scope of the invention, comprise, inter alia, pharmaceutically acceptable diluents, preservatives, solubilizers, emulsifiers, adjuvants and/or carriers. Such compositions can include diluents of various buffer content (e.g., Tris HCl, acetate, phosphate), pH and ionic strength; additives such as detergents and solubilizing agents (e.g., Tween 80, Polysorbate 80), anti oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington's Pharmaceutical Sciences, 18th Ed. (1990, Mack Publishing Co., Easton, Pa. 18042) pages 1435 1712 which are herein incorporated by reference. A pharmaceutical composition of the present invention can be prepared, for example, in liquid form, or can be in dried powder, such as lyophilized form. Particular methods of administering such compositions are described infra.

In yet another embodiment, a pharmaceutical composition of the present invention can be delivered in a controlled release system, such as using an intravenous infusion, an implantable osmotic pump, a transdermal patch, liposomes, or other modes of administration. In a particular embodiment, a pump may be used [see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)]. In another embodiment, polymeric materials can be used [see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)]. In yet another embodiment, a controlled release system can be placed in proximity of the target tissues of the animal, thus requiring only a fraction of the systemic dose [see, e.g., Goodson, in Medical Applications of Controlled Release, supra, vol. 2, pp. 115 138 (1984)]. In particular, a controlled release device can be introduced into an animal in proximity of the site of inappropriate immune activation or a tumor. Other controlled release systems are discussed in the review by Langer [Science 249:1527 1533 (1990)].

As used herein the term "biomarker" refers to a characteristic that is objectively measured and evaluated as an indicator of normal biologic processes, pathogenic processes, or pharmacologic responses to a therapeutic intervention.

As used herein, the terms "modulate", "modulating" or "modulation" refer to changing the rate at which a particular process occurs, inhibiting or promoting a particular process, reversing a particular process, and/or preventing the initiation of a particular process. Accordingly, if the particular process is tumor growth or metastasis, the term "modulation" includes, without limitation, decreasing the rate at which tumor growth and/or metastasis occurs; inhibiting tumor growth and/or metastasis; reversing tumor growth and/or metastasis (including tumor shrinkage and/or eradication) and/or preventing tumor growth and/or metastasis.

As used herein, the terms "tumor", "tumor growth" or "tumor tissue" can be used interchangeably, and refer to an abnormal growth of tissue resulting from uncontrolled progressive multiplication of cells and serving no physiological function. A solid tumor can be malignant, e.g. tending to metastasize and being life threatening, or benign. Examples of solid tumors that can be treated or prevented according to a method of the present invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, gastric cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, liver metastases, bile duct carcinoma, choriocarcinoma, seminoma, embryonal carcinoma, thyroid carcinoma such as anaplastic thyroid cancer, Wilms' tumor, cervical cancer, testicular tumor, lung carcinoma such as small cell lung carcinoma and non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, glioblastoma, and retinoblastoma.

As used herein, the phrase "chromosomal instability" refers to a higher than normal rate of mis-segregation of chromosomes or parts of chromosomes during mitosis due to defective cell cycle quality control mechanisms, resulting in copy number alterations (CNAs) or aneuploidy.

The phrase "gene amplification" or "copy number amplification" refers to an increase in the number of copies of a gene sequence. There may also be an increase in the RNA and protein made from that gene. Gene amplification is common in cancer cells, and some amplified genes may cause cancer cells to grow or become resistant to anticancer drugs. Gene amplification of oncogens on ecDNA is a frequent event in cancer. Unequal segregation of ecDNA from a parental tumor cell to offspring cells can rapidly increase tumor heterogeneity.

The phrase "tumor heterogeneity" refers to differences between cancer cells in a tumor. For example, a tumor may have multiple populations characterized by different genetic variants. Tumor heterogeneity can provide the tumor with an additional array of responses to microenvironment-induced and therapy-induced stress factors. These differences may explain why some tumor cells remain present in a patient after cancer treatment has finished. Reduced tumor heterogeneity leads to improved success with cancer treatments.

The term "drug response" as used herein, means any biological response in an organism that is the result of exposure to the drug. Drug responses can be favorable, such as when a patient's disease is eradicated by treatment with the drug, or unfavorable, such as when a patient enters a coma upon treatment with a drug.

The phrase "drug resistant tumor" refers to any tumor that retains tumor cells after cancer treatment has finished. A drug resistant tumor may be resistant to a specific treatment, e.g. treatment with an EGFR inhibitor, or may be resistant to multiple forms of treatment. A drug resistant tumor may initially have a favorable response to the drug, however some cells may remain unaffected.

Epigenetic state or Epigenetic phenomena, as used herein, means changes produced in gene expression caused by mechanisms other than changes in the underlying DNA sequence. For example, methylation of cytosines (Cs) or histone modifications can affect expression of a gene. These molecular modifications of the DNA are often called "epigenetic marks." For example, increased or decreased methylation of Cs in a genome are part of normal biology but can also be associated with disease. As used herein, "epigenetic state" refers to a gene or region in a genome that reflects particular epigenetic phenomena. For example, in a particular disease cohort, a gene can be found that causes disease through multiple mechanisms, including, but not limited to, impairment of protein function by a SNV, deletion of the gene via a CNV, little or no expression of the gene due to a change in the epigenetic state of the gene itself and/or regulatory region(s) in the genome controlling expression of the gene.

The phrase "histone lysine methyltransferase" or "KMT" refers to a histone-modifying enzyme that catalyzes the transfer of one, two, or three methyl groups to lysine residues of histone proteins. An inhibitor of KTM is, for example, chaetocin, DANep, BIX-01294, EGCG, sinefungin, adenoine dialdehyde, and novobiocin.

The phrase "histone lysine demethylase" or "KDM" refers to a histone-modifying enzyme that catalyzes the removal of methyl groups from the lysine residues of histone proteins. Methylated histones can either repress or activate transcription depending on the site of methylation. An inhibitor of KDM is, for example, tranylcyprome, phenelzine, a polyamine analogue, N-oxalyglycine (NOG), disulfuram, ebselen, and an N-oxalyl D-tyrosine derivative.

An "inhibitor" (interchangeably termed "antagonist") of a polypeptide of interest is an agent that interferes with activation or function of the polypeptide of interest, e.g., partially or fully blocks, inhibits, or neutralizes a biological activity mediated by a polypeptide of interest. For example, an antagonist of polypeptide X may refers to any molecule that partially or fully blocks, inhibits, or neutralizes a biological activity mediated by polypeptide X. Examples of inhibitors include antibodies; ligand antibodies; small molecule antagonists; antisense and inhibitory RNA (e.g., siRNA) molecules.

The phrase "EGFR inhibitor" refers to any compound natural occurring or synthesized, having the ability of inhibiting EGFR amplification. An EGFR inhibitor is for example, gefitinib, erlotinib, lapatinib, cetuximab, Osimertinib, panitumumab, neratinib, vandetanib, necitumumab, and dacomitinib.

The phrase "KDM4 inhibitor" refers to any compound natural occurring or synthesized, having the ability of inhibiting at least one member of the KDM4 family. Examples of KDM4 inhibitors include (R)-2-hydroxyglutaric acid disodium salt; NSC636819; 2,4-PDCA; QC6352; 2-OG, 2-HG, succinate, SAHA(4), NOG(5), PCA(6), 8-QH, CBN207192, CCT1, JIB-04, CBN209350, and QC6352. Other KDM4 inhibitors are known by those skilled in the art. See, e.g., (67-71).

The phrase "EZH2 inhibitor" refers to any compound natural occurring or synthesized, having the ability of inhibiting at least one member of the EZH2 family or interfere with EZH2 function. Examples of EZH2 inhibitors include tazmetostat, CPI-0209, GSK2816126 (GSK126), tazemelostat, DS-3201, 3-deazaneplanocin A (DZNep), EPZ00S687, Ei1, GSK343, GSK926, EPZ011989, CPI-1205, CPI-169, ZLD1039, PF-06821497, UNC1999, OR-S1/OR-S2, DS-3201b, DS-3201, SAH-EZH2, Astemizole, Wedelolactone, apomorphine hydrochloride, oxyphenbutazone, nifedipine, ergonovine maleate, Osimertinib (AZD9291), MAK683(EED226), A769662, GNA022, ANCR, FBW7, ZRANB1, OR-S1, OR-S2, and OR-S0. Other EZH2 inhibitors are known by those skilled in the art. See, e.g., (76-79).

The phrase "KDM5 inhibitor" refers to any compound natural occurring or synthesized, having the ability of inhibiting at least one member of the KDM5 family. Examples of KDM5 inhibitors include ZINC33576, KDM5-C70, KDM5-C49, KDM5i, CPI-203, CPI-455, CPI-382, CPI-383, CPI-766, YUKA1, CPI-4203, 5-(1-tert-Butyl-1H-pyrazol-4-yl)-6-isopropyl-7-oxo-4,7-dihydropyrazolo[1,5-a]pyrimidine-β-carbonitrile (KDM5 inhibitor compound 48), KDOAM-20, KDOAM-21, and KDOAMA-25. Other KDM5 inhibitors are known by those skilled in the art. See, e.g., (68, 72-75). Also see for example, G9a/EHMT1(GLP): UNC0638, UNC0642; and GLP inhibitors including 4 (MS0124) and 18 (MS012). Also available are EPZ035544, A-366, and BIX01294. For a further description of these agents, see Wang et al. *Acta Pharmacologica Sinica* volume 39, pages 866-874(2018)

II. Materials and Methods

The following materials and methods are provided to facilitate the practice of the present invention.

Cell Culture

Retinal pigment epithelial (RPE) and 293T cells were cultured in DMEM-high glucose (Sigma) media supplemented with 10% heat-inactivated fetal bovine serum (FBS), 100 U/ml penicillin, 100 ug/ml streptomycin, and 2 mM L-glutamine. HCC827 cells (lung adenocarcinoma), HCT-15 (colorectal adenocarcinoma) and HT-29 (colorectal adenocarcinoma) were cultured in RPMI 1640 Glutamax media (Gibco) supplemented with 10% heat-inactivated FBS, 100U/ml penicillin, 100 ug/ml streptomycin, 1% sodium pyruvate and 1% glucose. Hypoxic Conditions Cells were plated in cell culture dishes and allowed to adhere for 16-20 hours in normoxia (5% $CO_2$, 21% $O_2$, 74% $N_2$). For hypoxic treatment, cells were maintained in a HERA Cell 150 incubator (Thermo Scientific) flushed with 5% $CO_2$ and 1% $O_2$ and balanced with $N_2$ for the duration of the experiment. Cells were cultured in hypoxia for between 24 and 48 hours, prior to harvesting and downstream experimental processing. Hypoxic culture conditions were validated by immunoblot detection of carbonic anhydrase IX (CA-IX) expression, a well-established hypoxic biomarker signature (17).

Transfection Procedure

Cells were plated in cell culture dishes and allowed to adhere for 16-20 hours. Cell culture medium was removed and cells rinsed with phosphate buffered saline (PBS) prior to siRNA transfections (5 nM-10 nM/transfection) being performed using Lipofectamine 3000 transfection reagent (Life Technologies) in OPTI-MEM medium (Life Technologies). Transfections were changed to complete cell culture media after 4 hr of transfection, and cells were collected 72 hr post transfection. For co-transfection experiments both siRNA sequences were transfected at the same time. For experiments involving hypoxia or drug treatment, cells were exposed to these conditions at least 48 hours post-siRNA transfection.

Transient overexpression transfections were performed using Lipofectamine 3000 transfection reagent and P3000 reagent (Life Technologies) in OPTI-MEM medium for 4 hrs, followed by changing to complete media. Silencer select negative controls and siRNAs were purchased from Life Technologies. Their sequences and SEQ ID Nos: are shown in Table 1. At least two different siRNAs against every gene were used for each experiment.

Transduction with Histone H3.3 Variants

TABLE 1 siRNA Oligos

| siRNA Name | siRNA Sequence (SEQ ID No.) | Unique Identifier |
|---|---|---|
| EGFR | GAAUAGGUAUUGGUGAAUUtt (1) | s563 |
| EGFR | CCAUAAAUGCUACGAAUAUtt (2) | s564 |
| KDM4A | CUAUGGAAGAGUUCCGAAAtt (3) | s18635 |
| KDM4A | GCGACAAUCUUUAUCCUGAtt (4) | s18637 |
| G9A | GCUCUAACUGAACAACUAAtt (5) | s21469 |
| G9A | CGCUGAUUUUCGAGUGUAAtt (6) | s21470 |
| EHMT1 | CAGCUGCAGUAUCUCGGAAtt (7) | s36390 |
| EHMT1 | CUCUCACCGUUUCCACAAAtt (8) | s36391 |
| Suv39H1 | AGAACAGCUUCGUCAUGGAtt (9) | s13658 |
| Suv39H1 | CAAAUCGUGUGGUACAGAAtt (10) | s13660 |
| Suv39H2 | GAAUGAGUUUUGUCAUGGAtt (11) | s36183 |
| Suv39H2 | GUAUUCGCUUUGCAUCUUUtt (12) | s36184 |
| SETDB1 | GGACAAUGCAGGAGAUAGAtt (13) | s19110 |
| SETDB1 | CAACCAGACAUAUAGAUCAtt (14) | s19111 |
| EZH2 | GCUGACCAUUGGGACAGUAtt (15) | s4916 |
| EZH2 | GUGUAUGAGUUUAGAGUCAtt (16) | s4917 |
| KDM5A | GGACCGACAUUGGUGUAUAtt (17) | s11834 |
| KDM5A | GCGAGUUUGUUGUGACAUUtt (18) | s11836 |
| KDM5B | GGCAGUAAAGGAAAUCGAAtt (19) | s21145 |
| KDM5B | GGAAGAUCUUGGACUUAUUtt (20) | s21146 |
| KDM5C | CAGACGAGAGUGAAACUGAtt (21) | s15748 |
| KDM5C | GGAGUUACUCCAUUAACUAtt (22) | s15749 |
| KDM5C | CAGAGAAGCUAGACCUGAAtt (23) | s15750 |
| KMT2A | GGAGUGUAAUAAGUGCCGAtt (24) | s8817 |
| KMT2A | GGUUGCUAUAUGUUCCGAAtt (25) | s8818 |
| SETD1A | CAACGACUCAAAGUAUAUAtt (26) | s18789 |
| SETD1A | CGCAGUGAGUUUGAACAGAtt (27) | s18790 |
| SETD1B | CGUUCAAGGCUCAACCACAtt (28) | s22960 |
| SETD1B | CGGUGGAAAUUGUCGAAGAtt (29) | s22961 |

Plasmids for H3.3 wild type (WT), K4M, K9M, K27M and K36M mutants were provided by Peter Lewis (University of Wisconsin). Virus was generated by co-transfection of specific plasmids along with the packaging plasmids (AmphoPAK and VSVG) in 293T cells, using Lipofectamine 3000 transfection reagent (Life Technologies). DNA transfection was performed in Opti-MEM medium (Life Technologies) overnight. The virus containing super natant was collected after 24 hrs. RPE cells were infected in the presence of 8 mg/ml polybrene for 12 hrs with the viral supernatant (18). Cells were washed two times with DMEM, prior to being cultured in complete medium for 48 hours, before harvesting. For hypoxia, drug or growth factor treatment and overexpression experiments involving H3.3 K4M, RPE cells were infected as described above and cultured for 24 hours post infection before additional treatment (hypoxia, drug or growth factor treatment, or KDM4A transient-overexpression). Cells were harvested 24 hours later. For all experiments involving Histone H3.3 variants, RPE, HT-29 and HCC827 cells were harvested 48 hours after viral infection for western blot, cell cycle profiles and DNA FISH analysis.

RNA Extraction and Quantitative Real-Time PCR

Cells were washed and collected by trypsinization, followed by washing in PBS two times. Cell pellet was resuspended in Qiazol reagent (QIAGEN) and stored at −80° C. before further processing. Total RNA was extracted using miRNAeasy Mini Kit (QIAGEN) with an on-column DNase digestion according to the manufacturer's instructions. RNA was quantified using NanoDrop 2000 (Thermo Scientific). Single strand cDNA was prepared using Super Script IV first strand synthesis kit (Invitrogen) using random hexamers. Expression levels were analyzed using FastStart Universal SYBR Green Master (ROX) (Roche) according to the manufacturer's instructions on a LightCycler 480 PCR machine (Roche). Samples were normalized to β-actin. Primer sequences are provided in Table 2.

TABLE 2 qPCR Primer Sequences

| Primer Identifier | Primer Sequence | SEQ ID No. |
|---|---|---|
| KDM4A Forward | 5'-GCCTCCCACCCTATCCAA-3' | 30 |
| KDM4A Reverse | 5'-TCATCCAGTGTGTATACATCATCTCTC-3' | 31 |
| KDM4B Forward | 5'-GGCCTCAAGTGACGAGGA-3' | 32 |
| KDM4B Reverse | 5'-CTTCCACTGCAGAGACAGCA-3' | 33 |
| KDM4C Forward | 5'-AGCAGCAGTGAAGCTGAGG-3' | 34 |
| KDM4C Reverse | 5'-TGTACTTAAGCAGCTGTTTCCTGA-3' | 35 |
| KDM4D Forward | 5'-AATGGCAGACGTGGTCGT-3' | 36 |
| KDM4D Reverse | 5'-TCTTGGCTGGAGTCTGGAG-3' | 37 |
| KDM5A Forward | 5'-TCAGCACTGATACCCAAACTTC-3' | 38 |
| KDM5A Reverse | 5'-TCACATCTCCAGATTCTGACTGA-3' | 39 |
| KDM5B Forward | 5'-AGCAGACTGGCATCTGTAAGG-3' | 40 |
| KDM5B Reverse | 5'-GAAGTTTATCAACATCACATGCAA-3' | 41 |
| KDM5C Forward | 5'-CGAACGCATTGTTTATCCCTA-3' | 42 |
| KDM5C Reverse | 5'-CGTGTGTTACACTGCACAAGG-3' | 43 |
| KDM6A Forward | 5'-CTGCACAAGTAAAAGCAACTGTC-3' | 44 |
| KDM6A Reverse | 5'-CTTTTGGAGATACTGAATAGCATAGC-3' | 45 |
| KDM6B Forward | 5'-ACCCTCGAAATCCCATCAC-3' | 46 |
| KDM6B Reverse | 5'-GTGTTCGCCACTCGCTTC-3' | 47 |
| KMT2A Forward | 5'-GACAGTGTGCGTTATGTTTGACT-3' | 48 |
| KMT2A Reverse | 5'-TGGCCAATATATATAGTAAACGACCA-3' | 49 |
| KMT2B Forward | 5'-GGAGGAAGCAGCAAGCAGTA-3' | 50 |
| KMT2B Reverse | 5'-GCTCAGGTTTGGGGATTGT-3' | 51 |
| KMT2C Forward | 5'-CCACGAAAACAAAGAGGACAG-3' | 52 |
| KMT2C Reverse | 5'-TGGGTGCTTACACTTACACAAGAT-3' | 53 |
| KMT2D Forward | 5'-ATCCTGGAGACACCCATCAG-3' | 54 |
| KMT2D Reverse | 5'-GACAGGCTCAGGGTCAGTG-3' | 55 |
| SETDIA Forward | 5'-GCGGTCAGAGAACAGCTACC-3' | 56 |
| SETD1A Reverse | 5'-GGAGGCTGAAGATGCAGAGA-3' | 57 |

TABLE 2-continued

| qPCR Primer Sequences | | |
|---|---|---|
| Primer Identifier | Primer Sequence | SEQ ID No. |
| SETD1B Forward | 5'-CAAGTTCACGGACGCCTAC-3' | 58 |
| SETD1B Reverse | 5'-CCGCGGGAGAATTGTGTA-3' | 59 |
| G9A Forward | 5'-TGGGAAAGGTGACCTCAGAT-3' | 60 |
| G9A Reverse | 5'-GGGCAGAACCTAACTCCTCTG-3' | 61 |
| EHMT1 Forward | 5'-GCCAAAGAGGTGACGATAGC-3' | 62 |
| EHMT1 Reverse | 5'-ACTGCCCGTTGTGGTGTC-3' | 63 |
| Suv39H1 Forward | 5'-GTCATGGAGTACGTGGGAGAG-3' | 64 |
| Suv39H1 Reverse | 5'-CCTGACGGTCGTAGATCTGG-3' | 65 |
| Suv39H2 Forward | 5'-TCTTTCAAAAATGTTGTCCTGCT-3' | 66 |
| Suv39H2 Reverse | 5'-AGGTGGGATTTTAATTTGTTGG-3' | 67 |
| SETDB1 Forward | 5'-GCTTCCCCTTCCCTCTTTC-3' | 68 |
| SETDB1 Reverse | 5'-GGGAAGACATGCTTTTGTCCT-3' | 69 |
| EZH2 Forward | 5'-TGGGACCAAAACATGTAGACAG-3' | 70 |
| EZH2 Reverse | 5'-TTCCTTGGAGGAGTATCCACA-3' | 71 |
| EGFR Forward | 5'-GATACAGCTCAGACCCCACAG-3' | 72 |
| EGFR Reverse | 5'-TTTTGGGAACGGACTGGTT-3' | 73 |
| Actin Forward | 5'-AGGCCAACCGCGAGAAG-3' | 74 |
| Actin Reverse | 5'-ACAGCCTGGATAGCAACGTACAT-3' | 75 |

Immunoblotting

Cells were trypsinized and washed two times with PBS before resuspending in RIPA lysis buffer [50 mM Tris pH 7.4, 150 mM NaCl, 0.25% Sodium Deoxycholate, 1% NP40, 1 mM EDTA, 10% Glycerol] freshly supplemented with protease inhibitor and PhosSTOP phosphatase inhibitor cocktails (Roche). Cells were lysed on ice for 15 min and stored at −80° C. until further processing. Lysates were sonicated for 15 min (30 sec ON and 30 sec OFF cycle) at 70% amplitude in QSonica Q700 sonicator (Qsonica) followed by centrifugation at 12,000 rpm for 15 min. Cell lysate was transferred to a fresh tube and protein estimations were performed with Pierce BCA reagent (Thermo Scientific). Equal amounts of proteins were separated by SDS gel electrophoresis and transferred on nitrocellulose membrane (BioTrace NT, Pall Life Sciences) for at least 3 hr at a constant current. The membranes were blocked for at least 1 hr in 5% BSA-PBST (1×PBS with 0.5% Tween-20) or 5% milk-PBST and probed over night with specific antibodies as follows at the following dilutions: anti-GFP (Neuro mAb) (1:100); anti-β-Actin (1:10,000); anti-KDM4A (Neuro mAb) (1:100); anti-Flag (Sigma Aldrich) (1:500); anti-KDMSA (abcam) (1:500); anti-HALO (Promega) (1:1000); anti-Carbonic Anhydrase IX (Abcam) (1:1000).

Membranes were washed three times in PBST the next day, incubated with goat anti-mouse IgG peroxidase conjugated secondary antibody (170-6516, Biorad) or goat anti-rabbit peroxidase conjugated secondary antibody (A00167, GenScript) at 1:2500 in 5% milk-PBST for at least 1 hr at room temperature, washed 3 times with PBST and incubated in Lumi-Light western blotting substrate (12015200001, Roche) or SuperSignal West Pico PLUS Chemiluminiscent substrate (34577, ThermoScientific) for 2-4 min(s). Membranes were developed with Lumi-Film Chemiluminiscent detection film (11666657001, Roche). The western blot images displayed in the figures have been cropped and autocontrasted.

Cell Cycle Analysis

Samples were washed with PBS, centrifuged at 1400 rpm for 5 min, and permeabilized with 500 mL PBS containing 0.5% Triton X-100 for 30 min. After this incubation, cells were washed with PBS and centrifuged at 1400 rpm for 5 min. Samples were then stained with 1:100 dilutions of 1 mg/mL PI solution and 0.5M EDTA with 100 mg RNase A, overnight at 4° C. Cell cycle distribution was analysed by flow cytometry using the LSRII flow cytometry system (BD Biosciences).

DNA Fluorescent In Situ Hybridization (FISH)

The FISH protocol was performed as described previously in Black et al. (2013). Briefly, cell suspensions were fixed in ice-cold methanol:glacial acetic acid (3:1) solution for a minimum of four hours, before being spun onto 8 Chamber Polystyrene vessel tissue culture treated glass slides (Falcon, Fisher Scientific), using a centrifuge at 900 rpm. The slides were air-dried and incubated in 2×SSC buffer for 2 min, followed by serial ethanol dilution (70%, 85% and 100%) incubations for 2 min each, for a total of 6 min. Air-dried slides were hybridized with probes that were diluted in appropriate buffer overnight at 37° C., following a 4 minute incubation on a heat block at 78° C. The slides were washed the next day for 3 to 4 mins in appropriate wash buffers at 69° C. with 0.4×SSC for Cytocell probes or commercially available Agilent wash buffer 1 followed by washing in 2×SSC with 0.05% Tween-20 (Cytocell probes) or commercially available Agilent wash buffer 2 (Agilent probes). The slides were incubated in 1 mg/mL DAPI solution made in 1% BSA-PBS, followed by a final 1×PBS wash. After the wash, the slides were mounted with ProLong Gold antifade reagent (Invitrogen).

FISH images were acquired using an Olympus IX81 or Olympus IX83 spinning disk microscope at 40× magnification and analyzed using Slidebook 6.0 softwares. A minimum of 25 z-planes with 0.5 um step size was acquired for each field. Copy number gains for EGFR, 7 centromere (7C), 7p telomere (7p22.3), IKZF1 (7p12.2) and 8 centromere (8C) were scored in RPE cells as three or more foci. A minimum of 100 nuclei are scored for each independent experiment.

HCC827 cells have many EGFR amplifications that present as large EGFR amplification clouds (42). Therefore, the length of the EGFR DNA amplification cloud(s) was measured at its longest point, using the measuring tool within the Slidebook software. If multiple amplification clouds were present in a single nucleus, each cloud was measured. Each measurement was plotted and comparisons made between the overall size of the amplification cloud (um) in cells treated with siRNA to KDM4A, an inhibitor to the KDM4 family or transduced with either H3.3 WT or K4M. The analysis represents data from more than 400 nuclei from two-independent experiments with two different siRNAs to KDM4A, or across three independent experiments for the KDM4 inhibitor treatment and H3.3 transduction experiments. Each treatment condition is compared to either a non-targeting siRNA control or a DMSO vehicle control.

Lapatinib Treatment

Control or stable KDM4A overexpression RPE cells were plated in 24 well tissue culture plates at a density of $5\times10^3$. Cells were allowed to adhere for approximately 16 hours before Lapatinib (Abcam) (dissolved in DMSO) was supplemented to media to a final concentration of 1 μM. Cells were cultured in Lapatinib for a total of 48 hours before harvesting. Cells were stained with trypan blue solution (Sigma Aldrich) to assess cell viability and counted using a haemocytometer. Each condition was plated in triplicate wells and each well was counted in duplicate. An average was taken of all triplicates and used as a representative total. Data is displayed in FIG. 4G, in a comparable manner to Nathanson et al (2014) (12).

Gefitinib Treatment

Control or stable KDM4A overexpression RPE cells were plated in 24 well tissue culture plates at a density of $8\times10^3$. Cells were allowed to adhere for approximately 16 hours before Gefitinib (Abcam) (dissolved in DMSO) was supplemented to media to a final concentration of 1, 2.5 or 5 μM. Cells were cultured in Gefitinib for a total of 48 hours before harvesting. Cells were stained with trypan blue solution (Sigma Aldrich) to assess cell viability and counted using a hemocytometer. Each condition was plated in triplicate wells and each well was counted in duplicate. An average was taken of all triplicates and used as a representative total. Data is displayed in FIG. 4H, in a comparable manner to Nathanson et al (2014) (12).

Cell Proliferation Assay

Control, KDM4A overexpression or wild type parental RPE cells were plated at a density of $5\times10^3$ per well in a 6 well tissue culture plate. Each condition was plated in triplicate for each independent experiment. Cells were allowed to adhere for 16 hours before fresh complete media was added containing a final concentration of 50 ng/ml human recombinant EGF (Abcam). For control and KDM4A overexpression RPE cells, cells were harvested after 48 hours of EGF treatment and cell number calculated using a haemocytometer. For combinatorial drug experiments using parental RPE cells, EGF was added for 24 hours, following a 24 hour drug treatment with either KDM5i (1 μM) or EZH2i (3 μM).

For siRNA conditions, parental RPE cells were plated in 10 cm tissue culture plates at a density of $3\times10^5$. Cells were allowed to adhere for approximately 16 hours, prior to siRNA transfection (as previously described). 24 hours post siRNA transfection, cells were re-plated in triplicate into 24 well tissue culture plates at a density of $8\times10^3$. Remaining cells were re-plated and harvested 24 hours later for RNA extraction and qPCR transcript analysis. Cells were allowed to adhere in the 24 well plates for 24 hours before media was supplemented with human recombinant EGF to a final concentration of 50 ng/ml EGF. Cells were cultured in EGF for 24 hours before harvesting and counting using a haemocytometer, as described previously.

Scratch Assay

Control or stable KDM4A overexpression RPE cells were plated in 6 well tissue culture plates at a density of $2\times10^5$. Cells were allowed to adhere to plates for 24 hours. After 24 hours in culture, a p200 pipette tip was used to introduce a scratch wound in the centre of the well from the 12 o'clock to 6 o'clock position. Following the induction of the scratch wound, media was removed from each well and 1 ml of DMEM was used to rinse the wells, removing any cellular debris. After this wash, 3 ml of DMEM supplemented with vehicle or human recombinant EGF (Abcam) to a final concentration of 50 ng/ml, was added to each well. Cells were imaged at 0 hrs, 12 hrs and 24 hrs, using the EVOS imaging platform at 4× magnification. Scratch wound measurements were performed using the EVOS software with a minimum of 5 measurements taken at various locations, per scratch wound. All measurements were averaged. Each condition was performed in triplicate for each independent experiment.

H3.3 WT Vs K4M with EGF Treatment

Human recombinant EGF was added to histone H3.3 WT or K4M expressing RPE cells, 24 hours after viral transduction. Cells were cultured in EGF for 24 hours before harvesting for RNA, protein, cell cycle and DNA FISH analysis.

HCC827 KDM4 Inhibitor Treatment

HCC827 cells were treated at approximately 80% confluency with KDM4 inhibitor at a final concentration of 5 nM for 48 hours before being harvested for RNA, protein and DNA FISH analysis.

For hypoxia, EGF and KDM5i combinatorial experiments, RPE cells were pre-treated with 1 nM of KDM4 inhibitor exactly 24 hours prior to hypoxic exposure or EGF treatment. Immediately before transferring cells to hypoxia, or before drug or growth factor treatment, KDM4 inhibitor was supplemented to cells again at a concentration of 1 nM (double spike). Cells were then cultured in the respective conditions for 24 hours prior to harvesting for RNA, protein, cell cycle and DNA FISH analysis.

KDM5 Inhibitor Treatment

RPE cells were treated with KDM5 inhibitor (C70) at a final concentration of 1 μM for a total treatment time of 48 hours.

For experiments involving combination treatment with KDM4i, cells are pre-treated with KDM4i (1 nM) for 24 hours. After this 24 hour treatment, KDM5 inhibitor is supplemented along with an additional dose of KDM4 inhibitor at doses of 1 μM and 1 nM, respectively. Cells are harvested 48 hours after combination treatment.

For experiments involving combinations of KDM5 inhibitor and hypoxic exposure, RPE cells are treated with 1 μM KDM5 inhibitor for 24 hours. After this 24 hour treatment, cells are transferred to hypoxic conditions (1% $O_2$) for an additional 24 hours prior to harvesting for RNA, protein, cell cycle and DNA FISH analysis.

KDM5i and Gefitinib Combinatorial Treatment

Parental RPE cells are plated in 24 well tissue culture plates, in triplicate at a density of $5\times10^3$. Cells are allowed to adhere for approximately 16 hours before KDM5 inhibitor and Gefitinib alone or in combination are supplemented to each well at a final concentration of 1 μM and 2.5 μM, respectively. Cells are cultured for a total of 72 hours under drug treatment conditions before being harvested, stained with trypan blue and counted using a haemocytometer.

EZH2 Inhibitor Treatment

Parental RPE cells were treated with 1, 3 or 5 μM of EZH2 inhibitor for a total treatment duration of 72 hours before being harvested for RNA, protein, cell cycle and DNA FISH analysis. HT-29 and HCT-15 cells were treated with 3 μM EZH2i for 48 hours before being harvested for RNA, protein, cell cycle and DNA FISH analysis.

EZH2i+EGF Growth Assay

Parental RPE cells were plated in 24 well tissue culture plates, in triplicate at a density of $5\times10^3$. Cells were allowed to adhere for approximately 16 hours before media was supplemented with EZH2 inhibitor (C24) at a final concentration of 3 μM. After an initial 24 hour treatment, human recombinant EGF was supplemented to each well at a final concentration of 50 ng/ml. After 48 hours of EGF treatment, cells were harvested and counted using a haemocytometer.

EZH2i and H3.3 WT vs K4M

Parental RPE cells were virally transduced with either histone H3.3 wild type or K4M constructs, as previously described. 24 hours after viral transduction, EZH2 inhibitor was supplemented to cells at a final concentration of 3 μM. Cells were treated under these conditions for 24 hours, followed by harvesting for RNA, protein, cell cycle and DNA FISH analysis.

EZH2i+Hypoxia

Parental RPE cells were pre-treated with EZH2 inhibitor at a final concentration of 3 μM for 24 hours, prior to being transferred to hypoxic conditions for an additional 24 hours. Cells were then harvested and processed for RNA, protein, cell cycle and DNA FISH analysis.

RNA-Sequencing

Cells were incubated with Hoechst 33342 (ThermoFisher Scientific H3570) at 1/1000 directly into the media for 1 h at 37° C. degrees. Cells were then trypsinized and resuspended in media containing Hoechst at 1/1000. Cells were sorted with a BD FACS Fusion using the laser BV421-A into Qiazol, based on DNA content. Late S phase RNA was purified from cells using the Qiagen miRNeasy kit including a DNAse treatment. Total RNA sequencing libraries were prepped using the TruSeq Stranded Total RNA Sample Preparation with Ribo-Zero kit (Illumina). Libraries were paired-end sequenced (150 cycles each way) using a NextSeq500 (Illumina). STAR (59) aligner was used to map sequencing reads to transcripts in human hg19 reference genome. Read counts for individual transcripts were produced with HTseq-count (60), followed by the estimation of expression values and detection of differentially expressed transcripts using edgeR (61).

ChIP-Sequencing

Cells were incubated with Hoechst 33342 (ThermoFisher Scientific H3570) at 1/1000 directly into the media for 1 h at 37° C. degrees. Cells were then trypsinized and resuspended in media containing Hoechst at 1/1000 before crosslinking with 1% formaldehyde for 13 min at 37° C. degrees and quenching with 0.125M glycine. Cells were washed with 1×PBS and resuspended in media containing Hoechst (1/1000). Cells were sorted with a BD FACS Fusion using the laser BV421-A based on DNA content. For siKDM5A ChIP, cells were harvested as previously described (10,18). Sonication of chromatin was done with the Qsonica Q800R2 system (Qsonica). 0.5-10 ug of chromatin were used based on DNA content (nanodrop concentrations) with the following antibodies: H3K4mel (Abcam ab8895), H3K4me2 (Abcam ab32356), H3K4me3 (Millipore 07-473), H3K9mel (Abcam ab8896-100), H3K9me2 (Abcam ab1220), H3K9me3 (Abcam ab8898). ChIP sequencing libraries were prepped using the TruSeq ChIP Sample Preparation kit (Illumina). Libraries were single-end sequenced (75 cycles) using a NextSeq500 (Illumina).

ChIP-Seq Analysis

ChIP-seq data for the cells with KDM4A overexpression and the corresponding controls were based on merged samples for multiple points of cell cycle. Datasets for MLL knockdown (GSE81795) (49) and EZH2 knockdown samples (50) with their respective controls were retrieved from GEO. Sequencing reads were aligned against the human hg19 reference genome using BWA (62). Alignments were filtered for uniquely mapped reads and duplicates were removed. Input-normalized ratio coverage tracks were generated using Deeptools (63).

The ENCODE ChIP-seq data on histone modification enrichment were downloaded from the ENCODE website (found on the world wide web at encodeproject.org). These data were normalized by the ENCODE pipeline (64). Other public ChIP-seq datasets were downloaded as fastq files from GEO (GSE64243, GSE118954, GSE81795) (65), followed by mapping to the hg19 reference genome using BWA (66) and the generation of input-normalized coverage tracks using Deeptools (63).

EGFR Copy Number and Expression Analysis

Data from The Cancer Genome Atlas (TCGA) was obtained from the Broad Institute's Genomic Data Analysis Center (GDAC) Firehose (found on the world wide web at gdac.broadinstitute.org). A set of 7069 tumors spanning 21 tumor types was analyzed. Expression values for EGFR were extracted from the database, in units of transcripts per million (TPM). Copy number values for EGFR were also extracted from the database. FIG. 1A shows these EGFR expression and copy number values for each tumor analyzed.

Statistical Analysis

All pairwise comparisons were done using two-tailed Student's t-test unless otherwise stated. Significance was determined if the p value was <0.05. All FISH experiments were carried out with at least two independent siRNAs unless otherwise stated and at least 100 nuclei per replicate per experiment were counted for all the FISH studies conducted. All error bars represent the SEM.

The following examples are provided to illustrate certain embodiments of the invention. They are not intended to limit the invention in any way.

III. Example 1

K9 and K27 Methylation Interference Promotes EGFR Amplification

Previous analysis demonstrated that up to 54% of primary tumors across the pancancer TCGA dataset harbour EGFR amplifications of which some were shown to harbour extra-chromosomal amplification (10,11). To further explore EGFR amplification heterogeneity across and within tumors, we assessed the range of EGFR DNA copy gains and the associated EGFR RNA expression levels in each of the tumors in the pancancer TCGA dataset (7069 samples; FIG. 1A). The analyses revealed significant plasticity in EGFR DNA copy number across tumor types, ranging from 2.4-8 copies (red) to more than 8 copies (blue) (FIG. 1A). We also observed tumors with a loss of EGFR (black; FIG. 1A). As the DNA copy number increased there was an increase in EGFR RNA levels (FIG. 1A). Therefore, promoting more EGFR DNA copies tends to associate with increased EGFR transcripts in tumors.

Figure 2A:
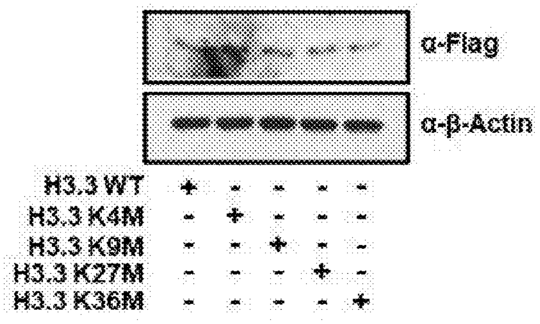
FIG. 2A-2D: H3K9/27 methylation controls EGFR amplification.
Figure 2B:
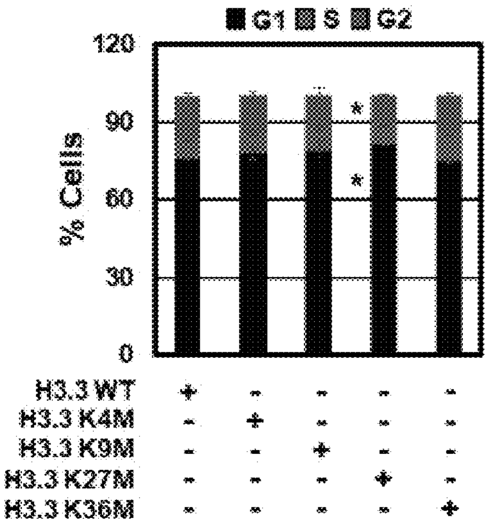

Since there is a range of EGFR DNA copy gains across tumors (FIG. 1A) and others have observed amplification plasticity (12), we assessed whether perturbation of epigenetic states associated with transient site-specific DNA amplifications could promote EGFR DNA copy gains (10,18). Prior studies demonstrated that the introduction of histone 3.3 lysine to methionine (H3.3 K-M) mutants into cells could interfere with the associated methylation at that specific lysine (30). In fact, we demonstrated that transducing cells with different H3.3 KM mutants could interfere with associated methylation, and in turn, promote amplification at specific regions in the genome (18,30). For example, 1q12h was copy gained with the introduction of H3.3K9M and H3.3K36M (18), while 1p32.3 was amplified with only H3.3K36M (10). These data illustrate the localized impact that modifying specific lysine methylation states have on the predilection of regions to undergo amplification versus whole genome instability and amplification (10,18). For these reasons, we tested whether introduction of H3K-M mutants into the immortalized retinal pigmental epithelial (RPE) cells that have a nearly diploid genome (18,31) and no documented mutations in the EGFR gene could allow us to identify residues important in repressing EGFR amplification (FIG. 2A). Since cell cycle arrest (e.g., G1/S; (18)) has been shown to block copy gains driven by epigenetic perturbation, we evaluated cell cycle profiles for each mutant tested (FIG. 2B). Our analyses did not reveal major changes in cell cycle profiles between cells expressing the different H3.3 K-M mutants (FIG. 2B); therefore, the cells were subsequently processed for DNA fluorescence in situ hybridization (DNA FISH) to determine the copy number status of EGFR.

Figure 1B:
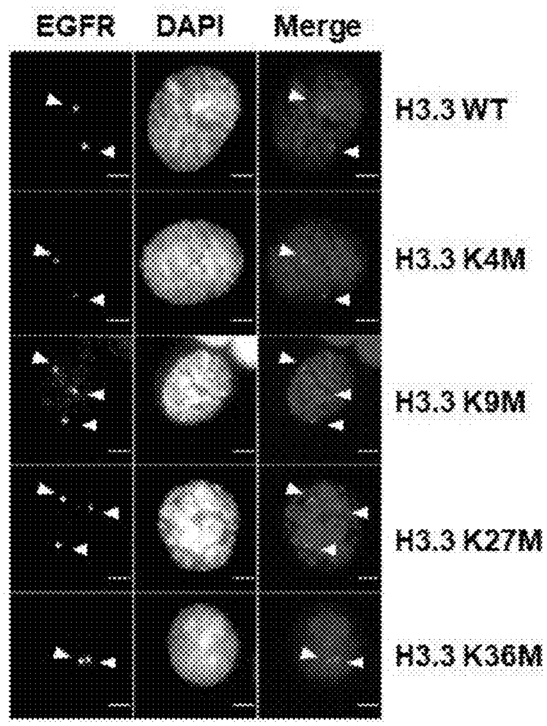
Figure 1C:
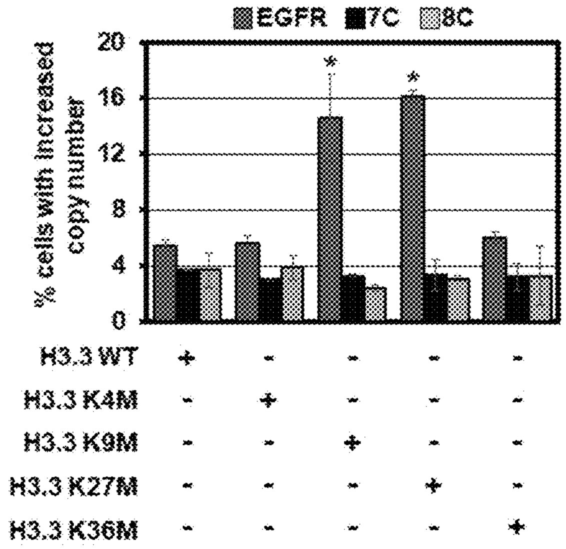
Figure 1D:
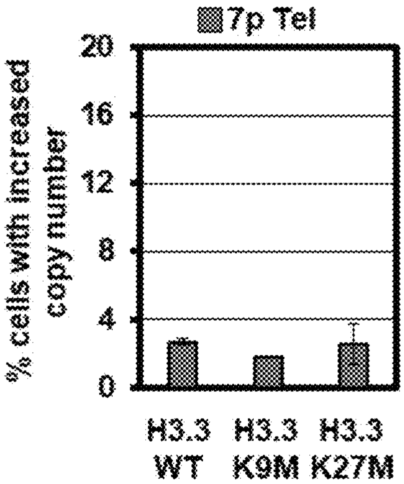
Figure 1E:
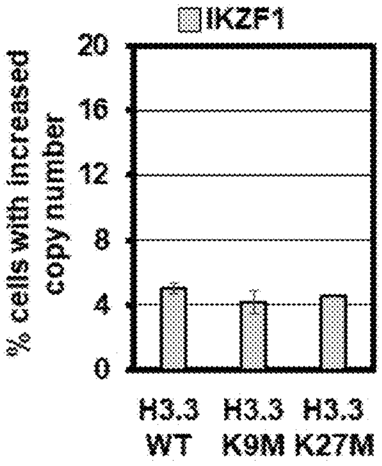
Figure 1F:
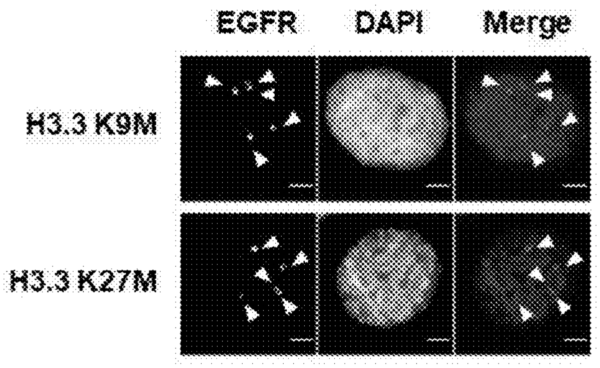
Figure 1G:
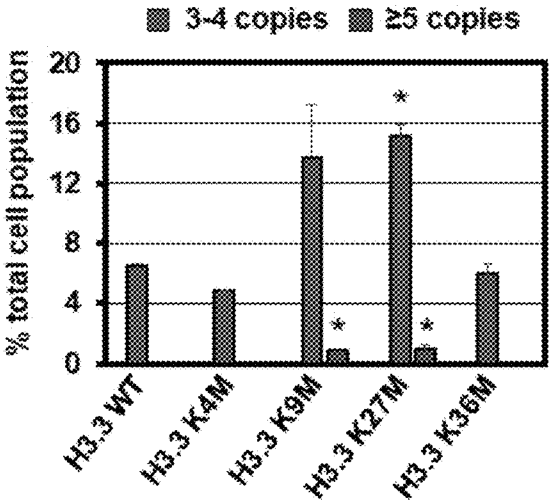
Figure 1H:
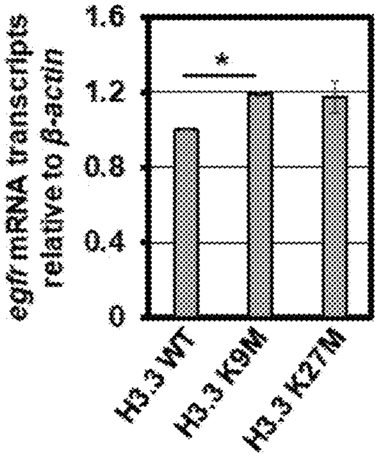
Figure 2C:
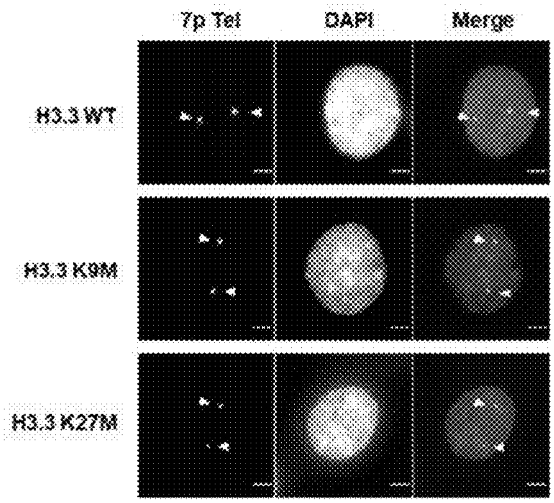
Figure 2D:
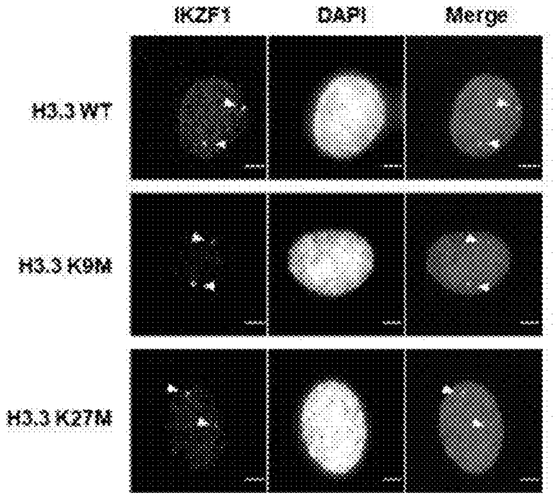

Individually H3.3 K9M and H3.3 K27M resulted in significant increases in EGFR DNA copy number, without changing the copy number of chromosome 7 and 8 centromeres (7C and 8C, respectively; FIG. 1B, 1C), the 7p telomere (7p tel, 7p22.2; FIG. 1D and FIG. 2C) or at a region adjacent to EGFR (IKZF1, 7p12.2; FIG. 1E and FIG. 2D). These data suggest that EGFR is undergoing site-specific copy gain as opposed to a whole chromosome 7 or chromosome 7p arm copy gain events, which is consistent with prior studies illustrating that exposure to K9M could promote site-specific amplifications on chromosome 1 (10,18). To date, no other region undergoing site-specific copy gain has been shown to be controlled by H3K27M (10,18). We also observed that ~1-2% of cells in the K9M and K27M mutants had higher EGFR amplification levels than wild type H3.3 (>5 copies; FIGS. 1F, 1G). Consistent with this increase in EGFR copy number, these cells also had a modest increase in EGFR transcript levels when compared to cells expressing a wild type H3 (FIG. 1H). Of interest, H3.3K4M and H3.3K36M did not promote EGFR copy gains. H3.3K36M has been shown to promote copy gains of other regions (e.g., 1q12h, 1921.2, 1p32.3) (10,18), which further highlights the specificity of epigenetic states in modulating amplification sensitivity in the genome.

Figure 1I:
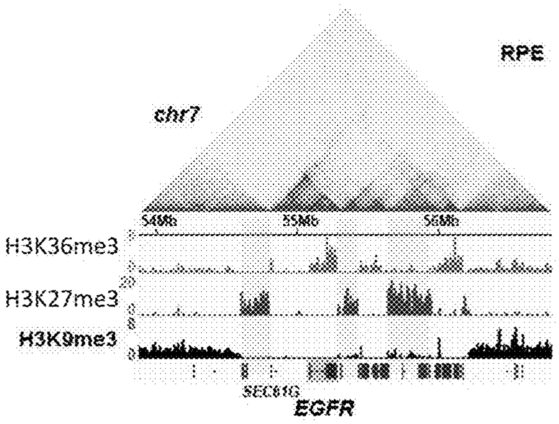
Figure 1J:
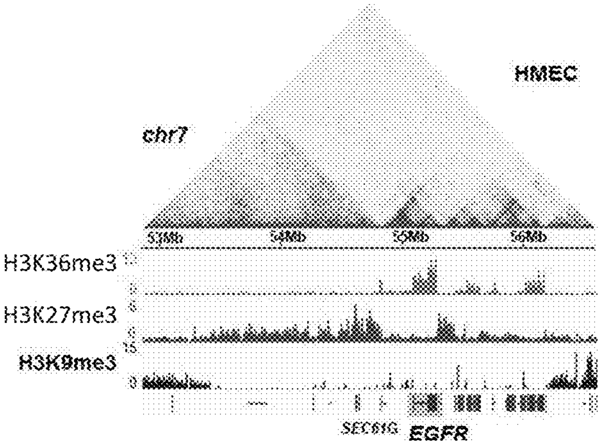

Consistent with these observations, our ChIP-sequencing (ChIP-seq) coupled with publicly available Hi-C data in RPE cells (32) suggest that the genomic vicinity of the EGFR locus has a specific chromosome structure and pattern of chromatin modifications (FIG. 1I). The EGFR gene body corresponds to a subdomain within a larger 500 kilobase (Kbp) 3D interaction domain, that also includes another gene, SEC61G. Both gene bodies are enriched in H3K36me3 (FIG. 1I). This chromatin interaction domain is flanked by two wide ~100 Kbp regions enriched in H3K27me3 (FIG. 1I, marked with blue shadow). The H3K27me3 region immediately adjacent to the 3' end of the EGFR gene forms a chromatin interaction domain reminiscent of the small Polycomb-generated domains described by Kundu et al (33). This subdomain on one boundary of the EGFR-containing domain interacts with the H3K27me3 region on the opposite boundary of the EGFR-containing domain, resulting in the streak of interactions above this domain in the Hi-C map (FIG. 1I). This looping interaction between distant H3K27me3 regions is similar to the Polycomb-mediated looping interactions previously described (33). Thus, EGFR resides within a 3D interaction domain whose boundaries are marked by two wide regions of H3K27me3 enrichment that form a looping interaction with each other (FIG. 1I).

Figure 1K:
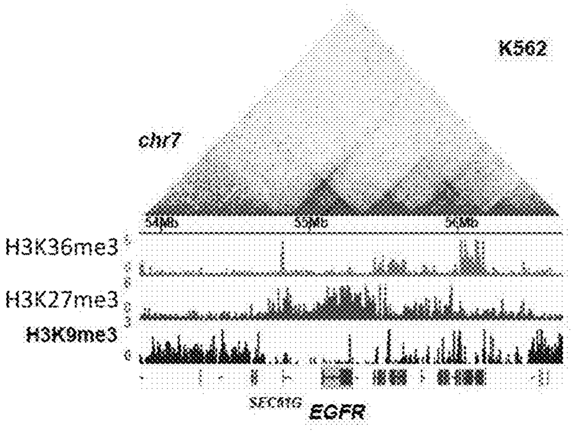
Figure 1L:
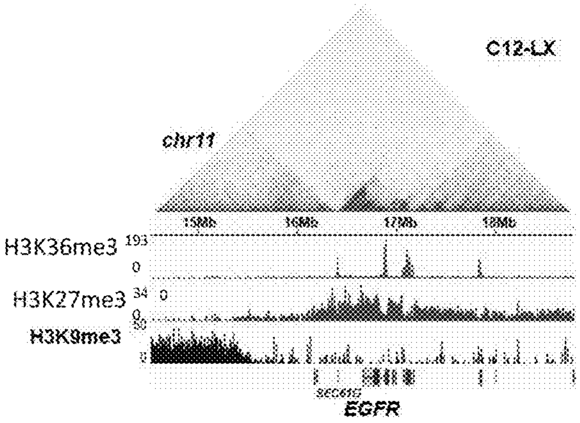
Figure 1M:
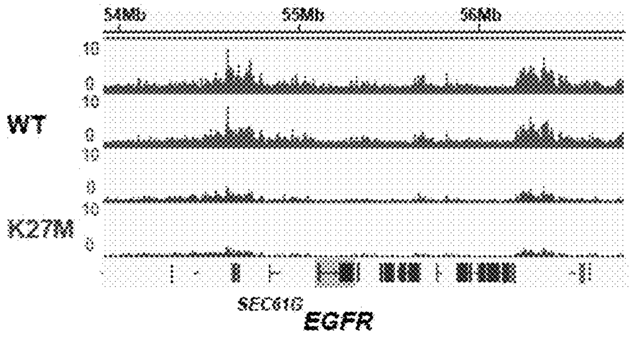

At a larger scale, the EGFR-containing domain, together with the adjacent H3K27me3-enriched boundary regions and two other interaction domains to the 3' of EGFR are part of ~1 megabase (Mb) region that is flanked on both sides by wide areas of H3K9me3 enrichment (FIG. 1I). In order to assess the significance of these associations, we evaluated a panel of cells analysed by ENCODE (34,35). In all cases, they contain similar configurations of H3K9me3 and H3K27me3 at the noted locations in the RPE cells (FIGS. 1I-1L). Cells that did not express EGFR had broader H3K27me3 in between the domains we documented in RPE cells (FIG. 1K, 1L). Furthermore, this pattern was conserved at the modification and organizational level when analyzing a mouse lymphoblast cell line C12-LX (FIG. 1L) (34,35). Lastly, we analysed publicly available H3K27me3 data in cells expressing H3.3K27M (36) and observed a loss of the H3K27me3 domains that flank EGFR (FIG. 1M), which was consistent with a direct effect on the locus, and in turn, amplification observed in FIG. 1B, 1C. Taken together, these epigenomic profiles and our genetic experiments using mutated histones are consistent with the possibility that this topological structure and H3K9/27 methylation are suppressing the propensity of the EGFR locus to undergo amplification and increased expression.

KDM4A Overexpression Promotes EGFR Copy Number Gains

Figure 4A:
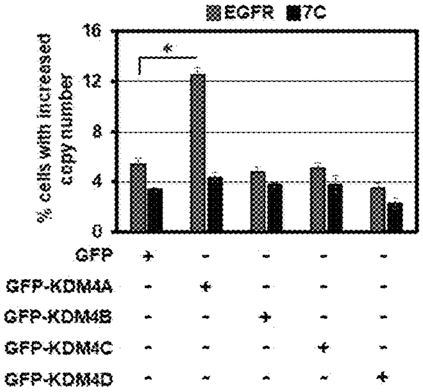
FIG. 4A-4K: KDM4A overexpression promotes EGFR copy gains.

The KDM4 family of histone lysine demethylases catalyze H3K9 and K36 demethylation (37,38). In addition, this enzyme family directly regulates DNA amplifications associated with H3K9 and K36 demethylation (10,18). Therefore, we tested whether overexpression of the KDM4 family of enzymes could phenocopy the increase in EGFR copy number observed upon H3K9 methylation interference. The GFP-tagged KDM4 family members were transiently overexpressed for 24 hours followed by DNA FISH analysis for EGFR DNA copy number (FIG. 3A-3F). Of the overexpressed KDM4 family members, only transient KDM4A overexpression promoted increased EGFR DNA copy number, which highlights the specificity of KDM4A in regulating the EGFR locus (FIG. 4A). Furthermore, catalytically inactive KDM4A (H188A; (38)) and a mutant lacking the Tudor domains that recognize H3K4 methylation (Tudor Del; (39)) were unable to promote EGFR copy gains (FIG. 4B and FIG. 3G-3I). These data were also confirmed with RPE cells that stably overexpressed KDM4A (FIG. 4C, 4D and FIG. 3J, 3K). Chromosome 7 or 8 centromere loci, 7p Tel as well as other previously tested loci were not impacted by KDM4A overexpression (FIG. 4A, 4D and FIG. 3I; (10,18)).

Figure 4B:
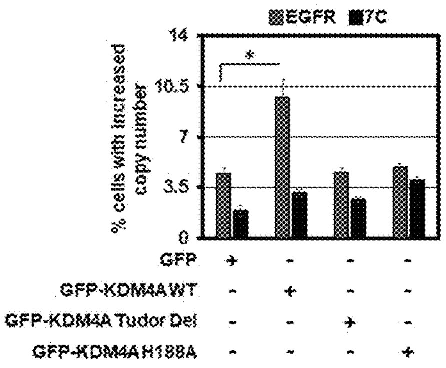
Figure 4C:
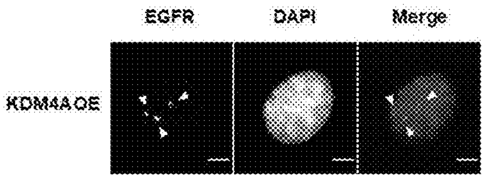
Figure 4D:
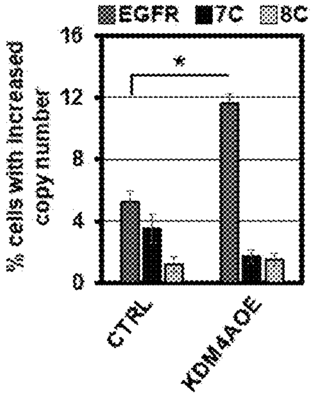
Figure 4E:
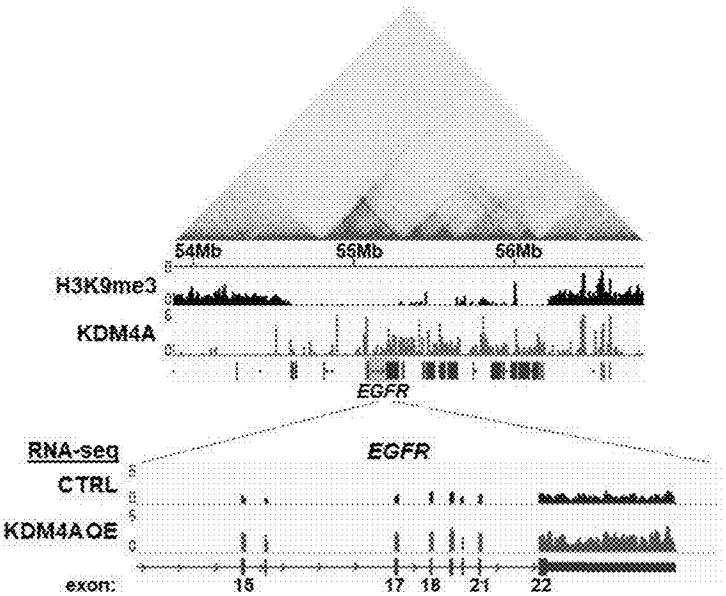
Figure 4F:
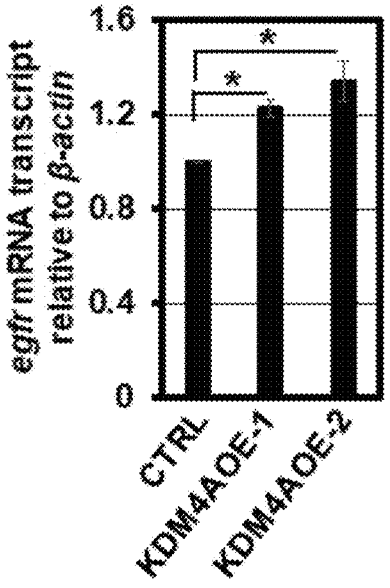

Consistent with these findings, analysis of available KDM4A ChIP-seq data (40) revealed that KDM4A was enriched across the EGFR locus between the H3K9me3 blocks (1.6 Mb; FIG. 4E, upper panel: KDM4A in blue and H3K9me3 in black). These observations were consistent with the previous analyses that noted KDM4A occupied the EGFR promoter region (40), which occurs within this larger binding domain that we have identified. In addition to promoting copy gains, KDM4A overexpression also increased EGFR transcripts as determined by both RNA-sequencing and quantitative RT-PCR (FIG. 4E, 4F). These findings are entirely consistent with a recent report that demonstrated a role for KDM4A in regulating EGFR gene expression (40). Taken together, these data illustrate that KDM4A directly regulates this locus and plays a fundamental role in generating EGFR DNA copy gains and in regulating EGFR expression.

Figure 3A:
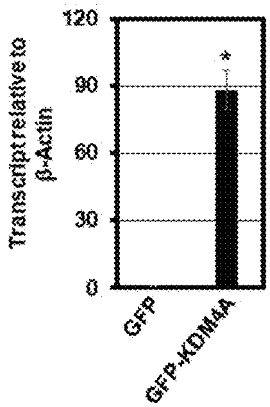
FIG. 3A-3M: KDM4A overexpression promotes EGFR copy gains.
Figure 3B:
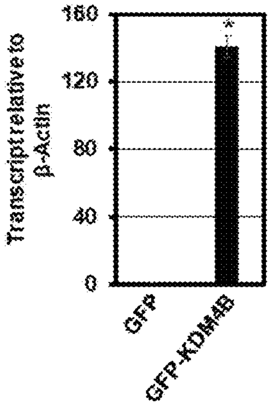
Figure 3C:
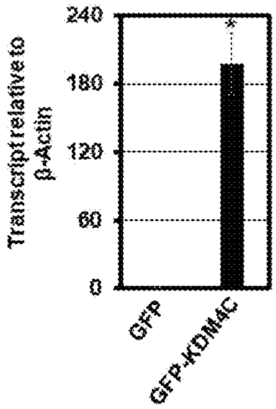
Figure 3D:
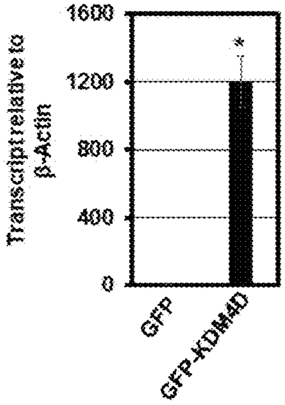
Figure 3E:
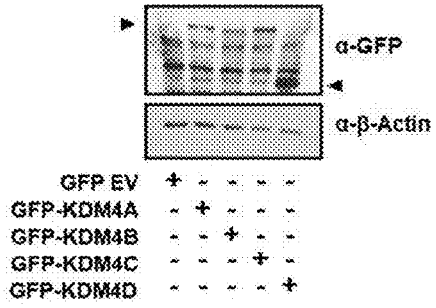
Figure 3F:
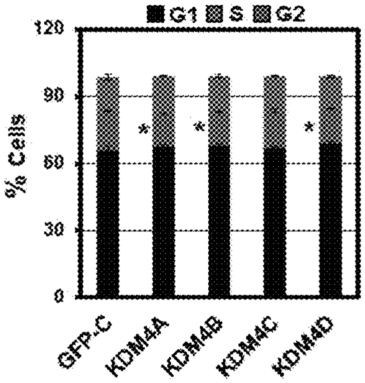
Figure 3G:
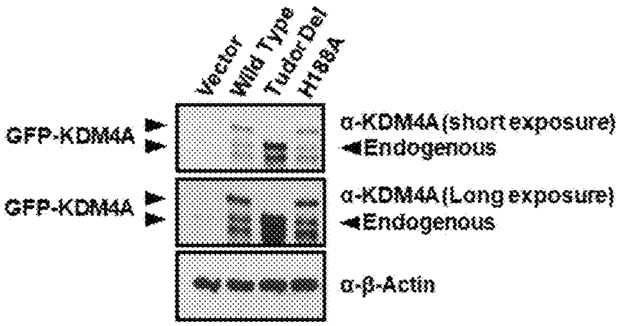
Figure 3H:
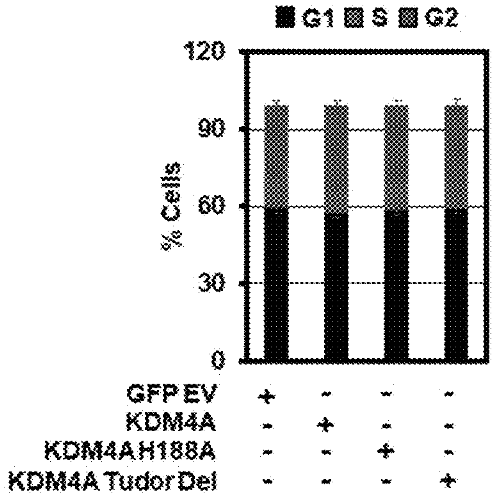
Figure 3I:
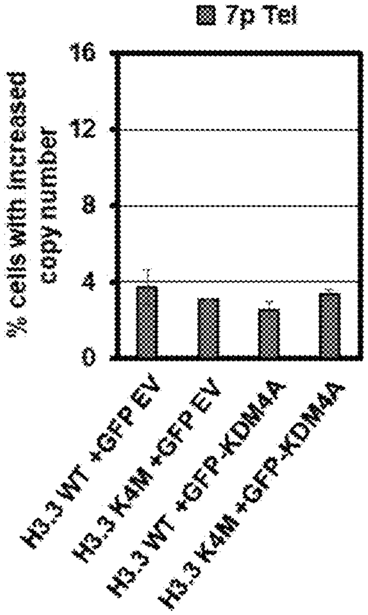
Figure 3J:
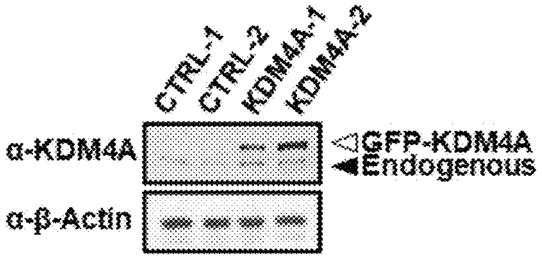
Figure 3K:
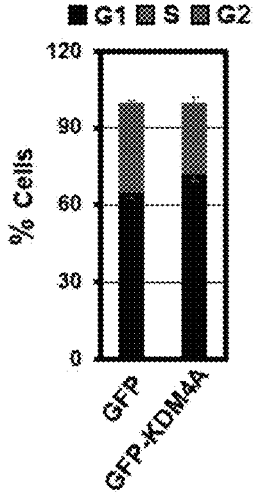
Figure 3L:
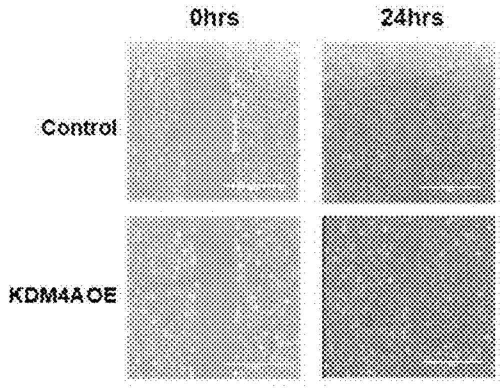
Figure 3M:
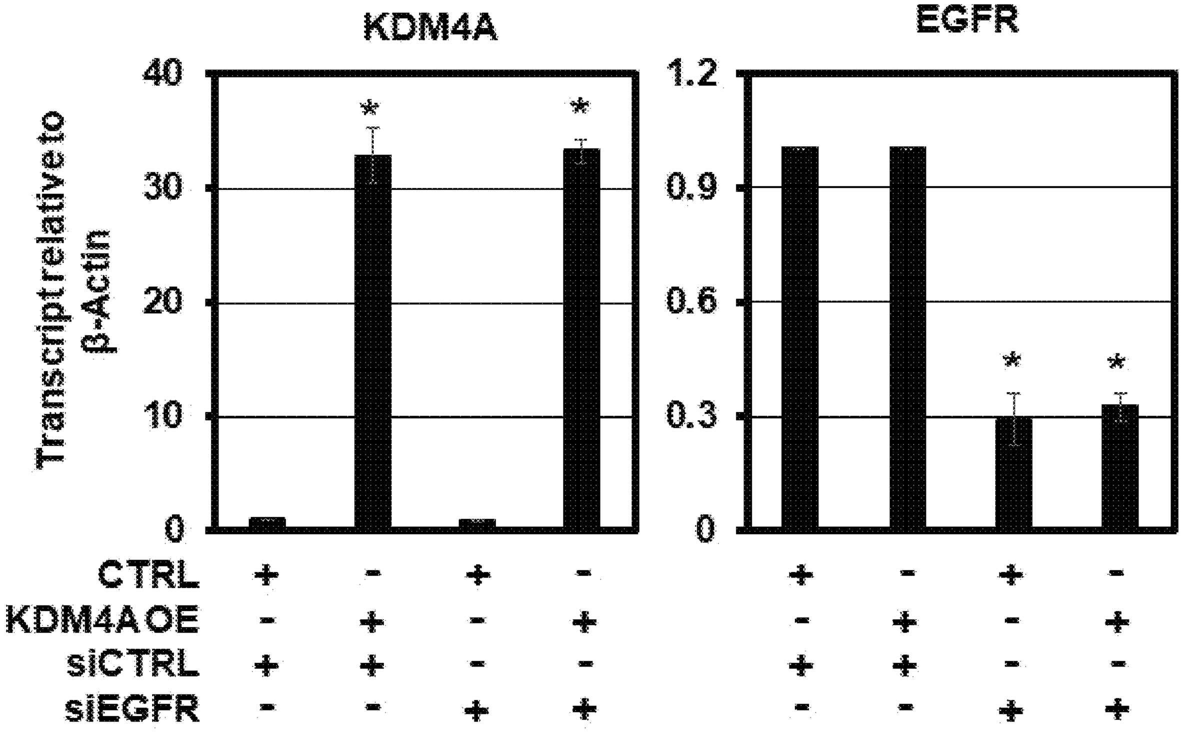
Figure 4G:
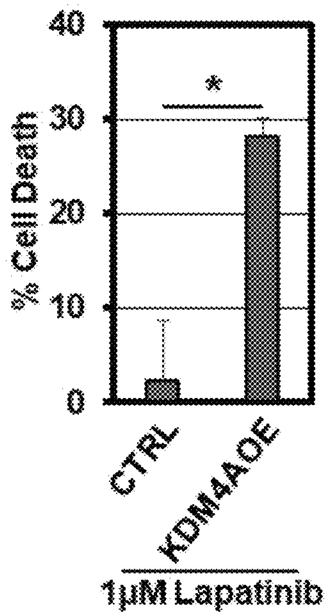
Figure 4H:
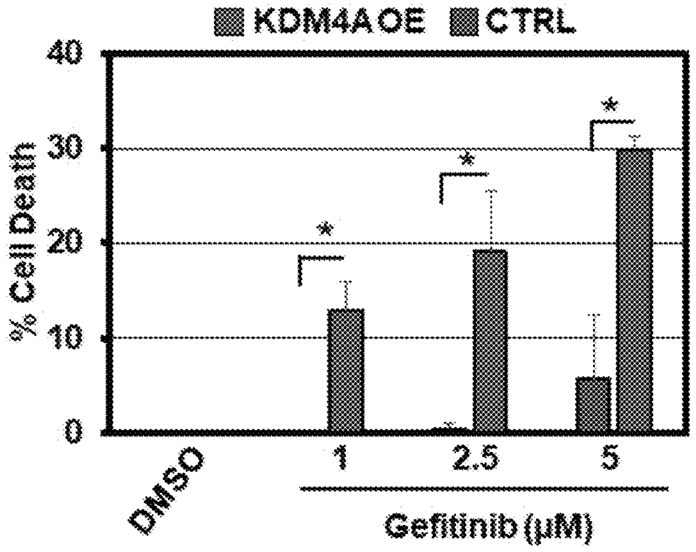
Figure 4I:
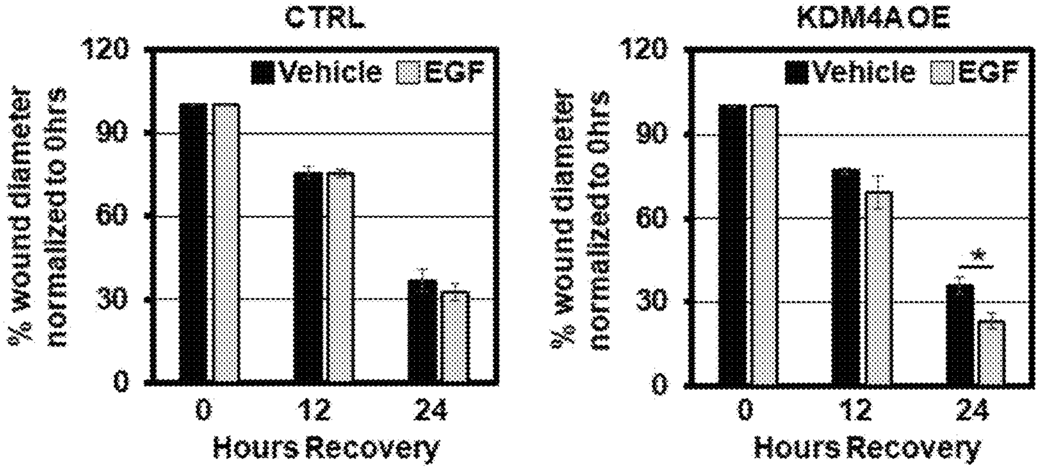
Figure 4J:
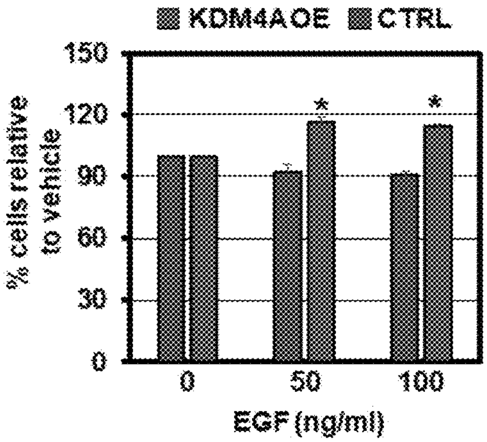
Figure 4K:
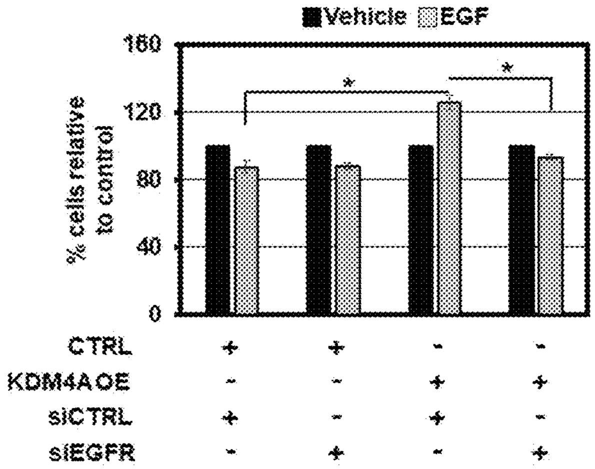

Since KDM4A overexpression promoted EGFR copy gains and increased RNA expression, we assessed the impact that KDM4A overexpression had on EGFR inhibitor sensitivity. We observed increased sensitivity to both Lapatinib and Gefitinib in KDM4A overexpressing cells when compared to control cells (FIG. 4G, 4H). Based on these data, we further reasoned that EGF supplementation would promote cell proliferation and migration in KDM4A overexpressing cells. Consistent with this hypothesis, KDM4A overexpressing cells had a modest but significant increase in cell migration as compared to control cells in scratch assays and increased cell proliferation in response to EGF (FIG. 4I, 4J and FIG. 3L). Furthermore, the increased cell proliferation upon EGF-treatment in KDM4A overexpressing cells was completely suppressed by siRNA-mediated depletion of EGFR (FIG. 4K and FIG. 3M), which emphasized the importance of increased EGFR gene expression in order to observe the increased cell proliferation.

Figure 5A:
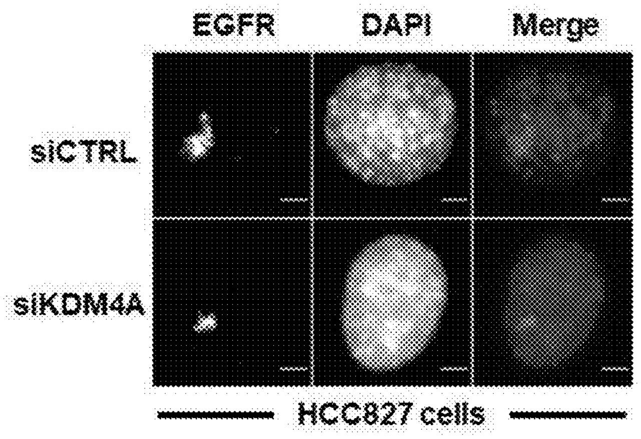
FIG. 5A-5E: KDM4A controls EGFR amplification in HCC827 cells.
Figure 5B:
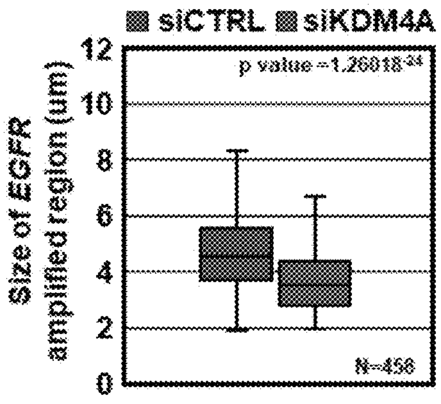
Figure 5C:
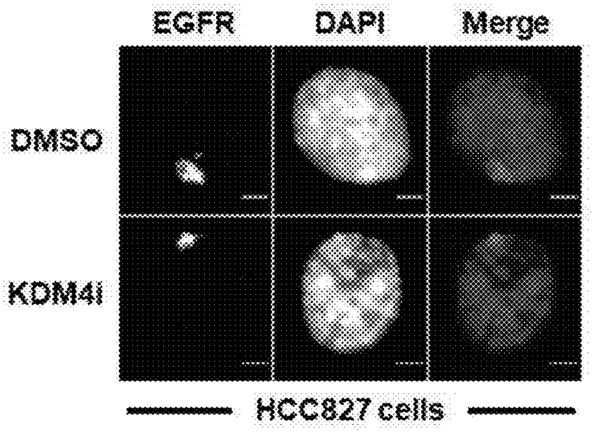
Figure 5D:
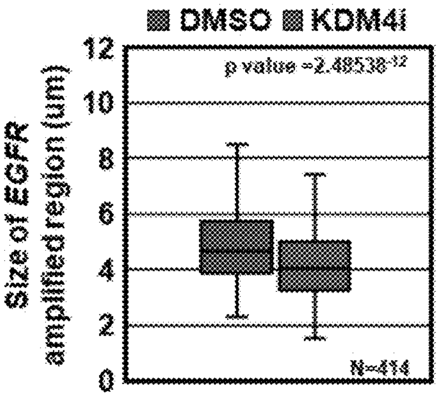
Figure 5E:
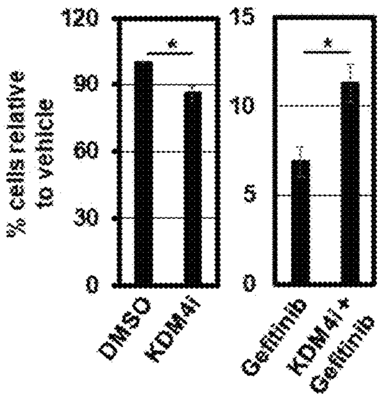
Figure 6A:
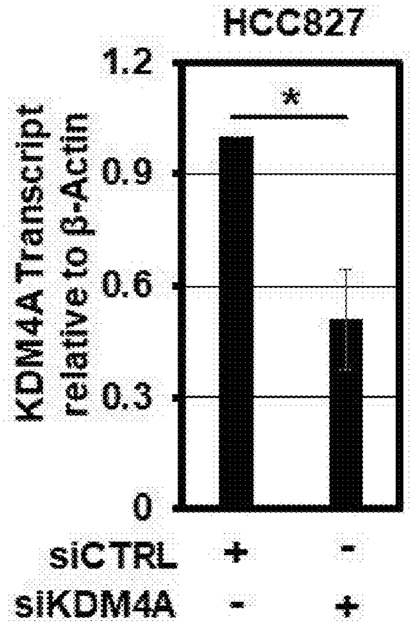
FIG. 6A-6B: KDM4A controls EGFR amplification in HCC827 cells.
Figure 6B:
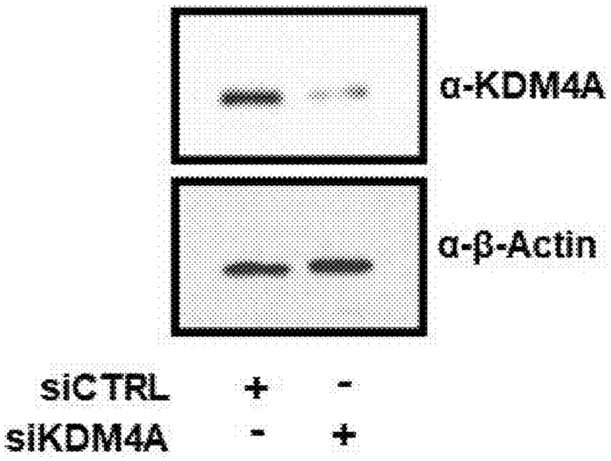

Since EGFR amplifications are observed in lung tumors (10,22) and cancer cell lines (i.e., HCC827; (41,42)), we tested whether KDM4A could be contributing to the observed EGFR amplifications in lung cancer cells. We used both KDM4A siRNA depletion and chemical inhibition (KDM4i (QC6352); (43)) of the KDM4 family to assess the impact of KDM4A on EGFR amplification. Specifically, we used DNA FISH to test whether the classically used EGFR amplified HCC827 lung cancer cells would have reduced amplifications upon KDM4A depletion or inhibition. HCC827 cells, in addition to exhibiting extensive EGFR amplification, have an acquired activating mutation within the EGFR tyrosine kinase domain (Exon 19 deletion) (41). As previously noted, HCC827 cells had very high EGFR DNA amplification levels that form large EGFR gene cluster clouds (FIG. 5A). The amplifications are so abundant that they appear as clouds in the interphase nuclei (42). However, KDM4A depletion significantly reduced the size of EGFR amplified clouds in the HCC827 cells (FIG. 5A, 5B and FIG. 6A, 6B). Furthermore, KDM4 family inhibition significantly reduced the extent of EGFR amplification in these cells as well (FIG. 5C, 5D). Based on these observations and the fact that EGFR DNA amplification has been shown to correlate with better EGFR inhibitor responses in patients (24-29), we hypothesized that KDM4 inhibitor treatment would reduce the sensitivity of HCC827 cells to the EGFR inhibitor, Gefitinib. As anticipated, a reduction in EGFR DNA amplification directly correlated with a reduced response to Gefitinib (FIG. 5E, right panel). Taken together, these data highlight a functional and significant role for KDM4A in modulating EGFR amplifications, expression and response to both EGFR inhibitors and growth factors in both diploid, non-transformed cells and EGFR amplified cancer cells.

H3K9 KMTs Regulate EGFR Copy Number

Figure 8A:
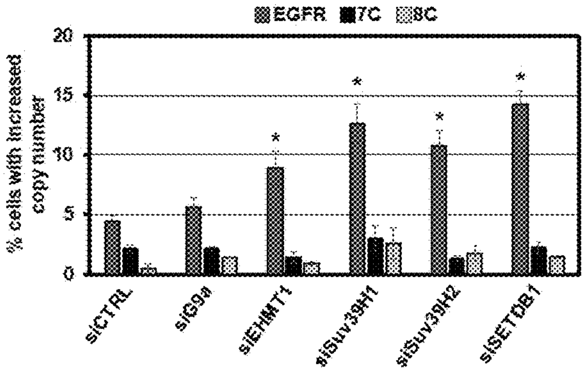
FIG. 8A-8K: H3K9/K27 KMTs regulate EGFR amplification.
Figure 8B:
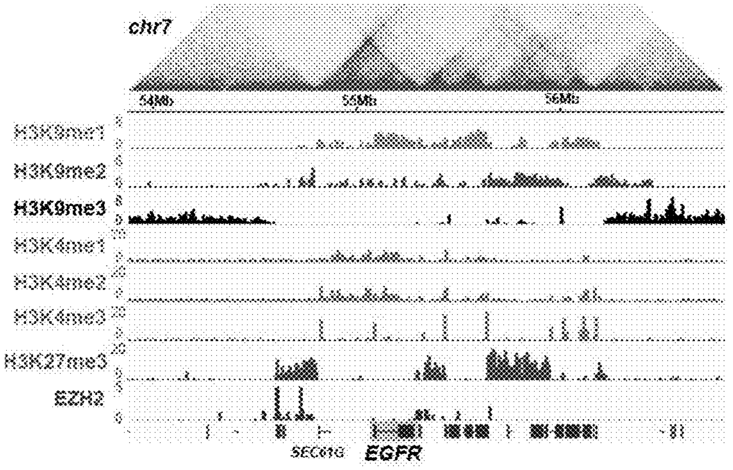

Since K9 methylation interference and catalytically active KDM4A overexpression promoted EGFR amplification, we tested whether each of the H3K9 lysine methyltransferases (K9 KMT) were equally capable of inhibiting EGFR copy gains or whether there was enzyme specificity. Specifically, RPE cells were siRNA depleted with at least two independent siRNAs for each K9 KMT. The knockdowns were confirmed and cell cycle profiles were generated for each siRNA, which ensures no overt arrests occurred, and in turn, interfere with EGFR copy gains (FIG. 7A-7F). Samples were then analyzed by EGFR DNA FISH. With the exception of G9a/KMT1C, depletion of all other K9 KMTs resulted in a significant increase in EGFR DNA copy number (FIG. 8A). These data coupled with the methylation interference and demethylase activity requirement, strongly suggest that maintaining the degree of H3K9mel/2/3 methylation at this locus is critical for preventing amplification. Consistent with this notion, H3K9mel/2/3 ChIP-seq illustrated that the higher ordered organized domains that contained the EGFR locus were enriched for H3K9mel/2 between the H3K9me3 flanking blocks (FIG. 8B). Taken together, these data imply the need to balance H3K9 methylation in order to prevent or promote EGFR copy gains.

EZH2 and KDM6 Enzymes Regulate EGFR Copy Number

In addition to H3K9 methylation interference causing EGFR amplification, we also observed that H3K27 methylation interference increased EGFR copy number (FIG. 1B, 1C). Therefore, we sought to further explore the importance of K27 methylation in modulating EGFR amplification. First, we compared a publicly available EZH2 ChIP-seq dataset (44) to our H3K27me3 profiles. We observed an overlap between EZH2 occupancy and the H3K27me3 domains that flank the EGFR locus (FIG. 8B). These binding profiles and the fact H3K27 methylation interference promoted EGFR amplification (FIG. 1B, 1C) and reduced H3K27me3 flanking the EGFR locus (FIG. 1M) prompted us to then test whether EZH2 siRNA-mediated depletion or chemical inhibition would phenocopy H3K27 methylation interference-induced EGFR copy gains.

Figure 7A:
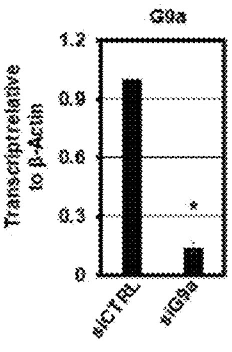
FIG. 7A-7T: H3K9/27 KMTs regulate EGFR amplification.
Figure 7B:
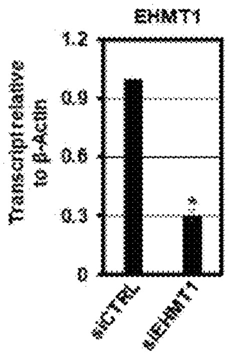
Figure 7C:
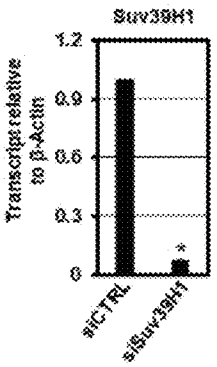
Figure 7D:
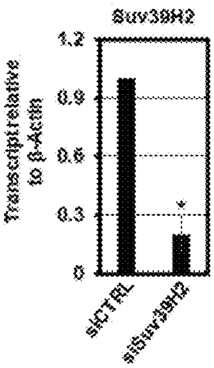
Figure 7E:
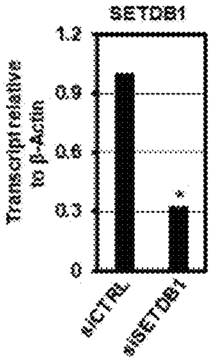
Figure 7F:
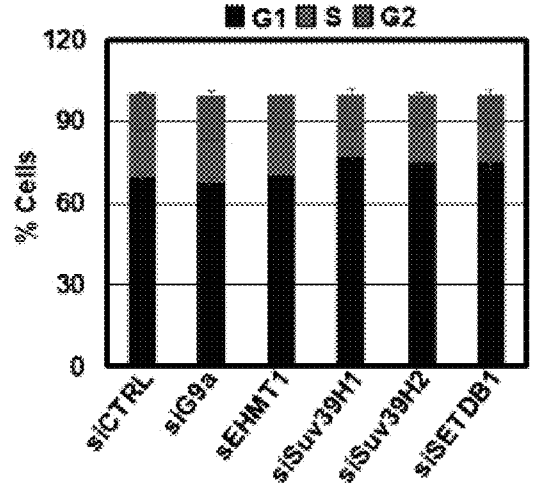
FIG. 7F) Cell cycle analysis of RPE cells treated with siRNAs targeting the H3K9 KMT family. Cells were harvested 72 hours post transfection.
Figure 7G:
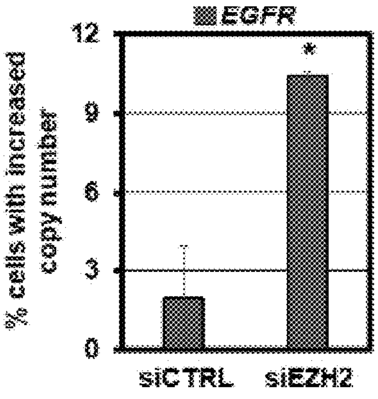
FIG. 7G) siEZH2 treated RPE cells had significant EGFR copy gains.
Figure 7H:
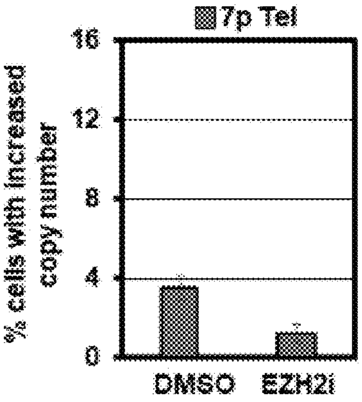
FIG. 7H) siEZH2 treated RPE cells did not have significantly altered 7ptel DNA copy levels.
Figure 7I:
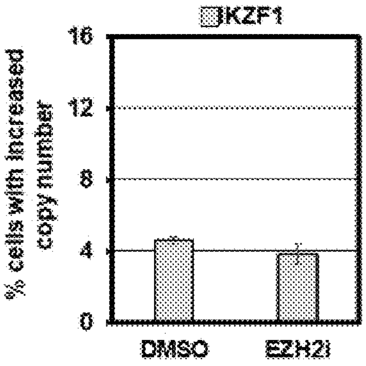
FIG. 7I) siEZH2 treated RPE cells did not have significantly altered IKZF1 DNA copy levels.
Figure 7J:
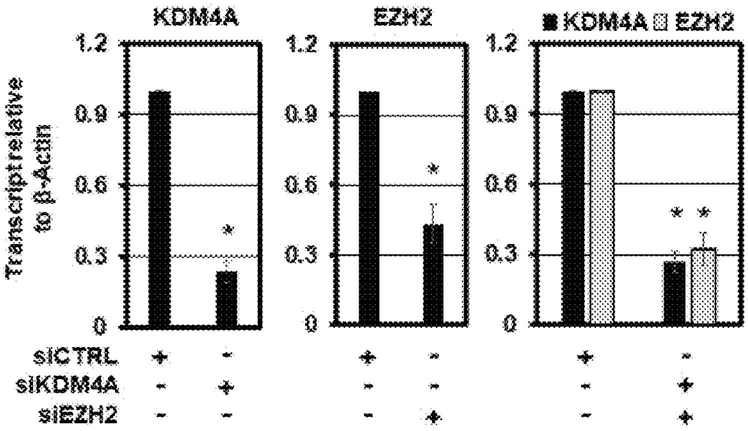
FIG. 7J) qRT-PCR analysis of RPE cells treated with siRNAs targeting KDM4A and EZH2 either alone or in combination. Cells were harvested 72 hours post siRNA transfection.
Figure 7K:
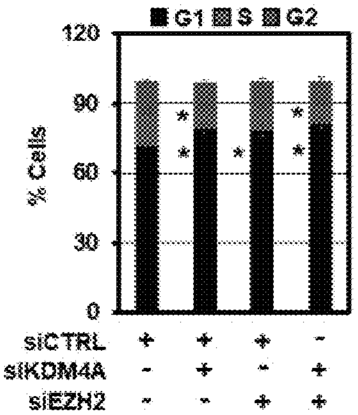
FIG. 7K) Cell cycle analysis of RPE cells treated with siRNAs targeting KDM4A and EZH2 either alone or in combination. Cells were harvested 72 hours post siRNA transfection.
Figure 7L:
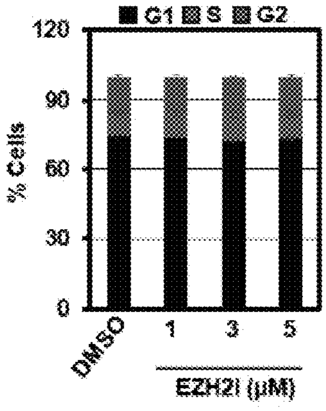
FIG. 7L) Cell cycle analysis of RPE cells treated with 1 μM, 3 μM or 5 μM of EZH2i for 72 hours.
Figure 7M:
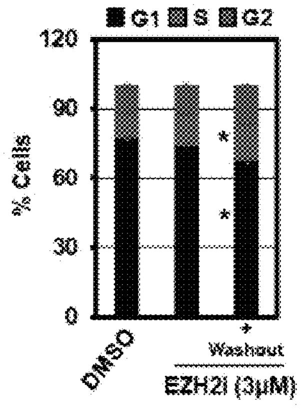
FIG. 7M) Cell cycle analysis of RPE cells treated with continuous 3 μM EZH2i or after washout and replacement with drug-free DMEM.
Figure 7N:
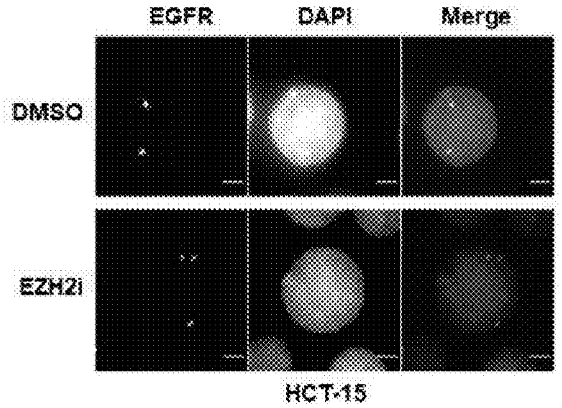
FIG. 7N) Representative DNA FISH images of HCT-15 nuclei from cells treated with EZH2i. EGFR (red) and DAPI (blue) are shown in the merge.
Figure 7O:
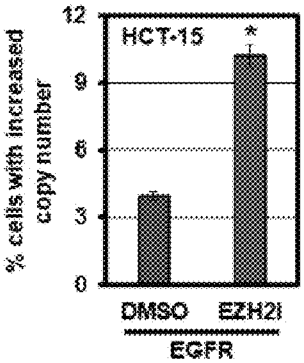
FIG. 7O) EZH2i promoted significant EGFR DNA copy gains in HCT-15 cells.
Figure 7P:
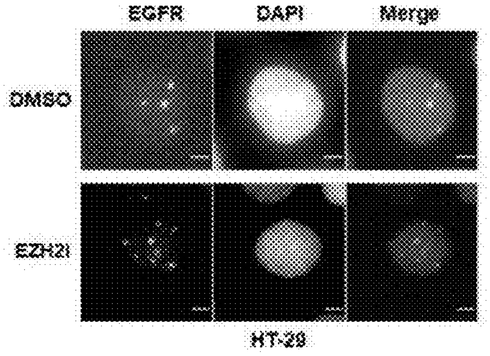
FIG. 7P) Representative DNA FISH images of HT-29 nuclei from cells treated with EZH2i. EGFR (red) and DAPI (blue) are shown in the merge.
Figure 7Q:
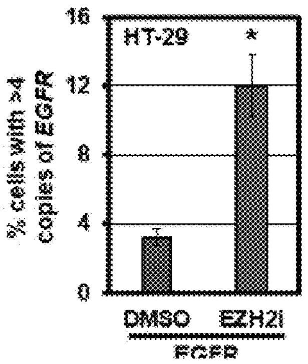
FIG. 7Q) EZH2i promoted significant EGFR DNA copy gains in HT-29 cells.
Figure 7R:
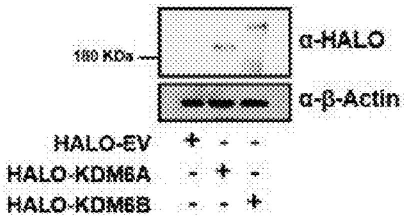
FIG. 7R) Representative α-HALO immunoblot analysis verifying expression of HALO-tagged KDM6A or KDM6B constructs in RPE cells. Cells were harvested 24 hours post DNA transfection.
Figure 7S:
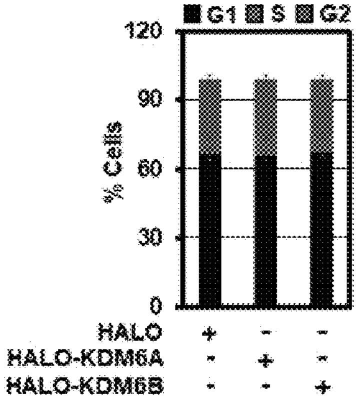
FIG. 7S) Cell cycle analysis of RPE cells expressing HALO-tagged KDM6A or KDM6B constructs. Cells were harvested 24 hours post DNA transfection.
Figure 8C:
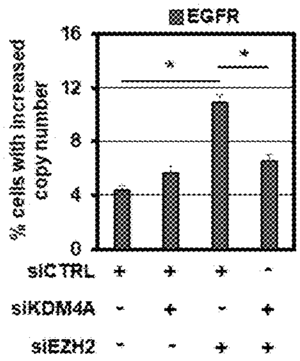
Figure 8D:
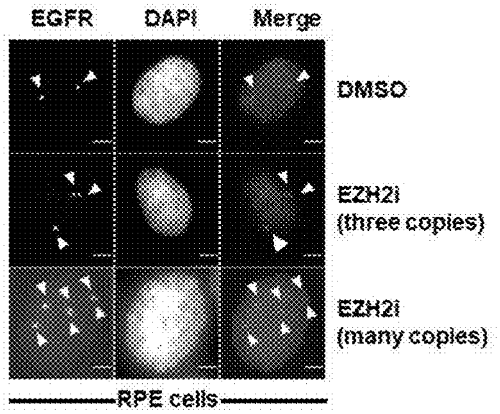
Figure 8E:
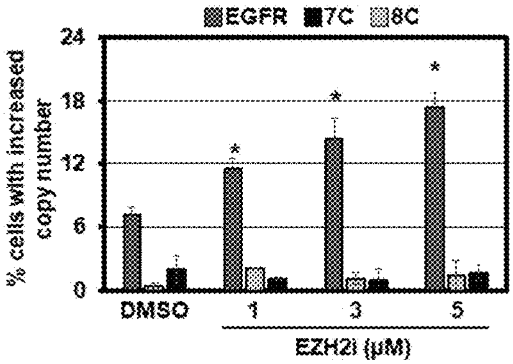
Figure 8F:
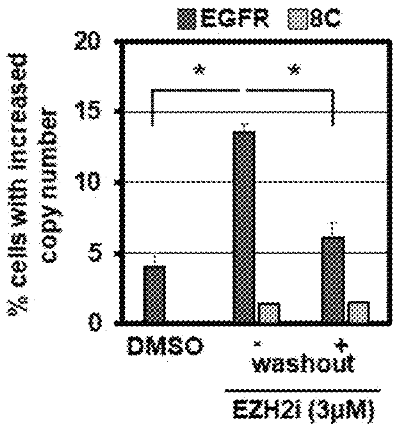
Figure 8G:
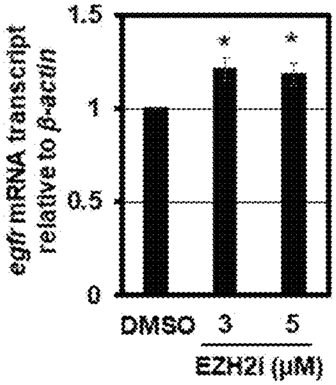
Figure 8H:
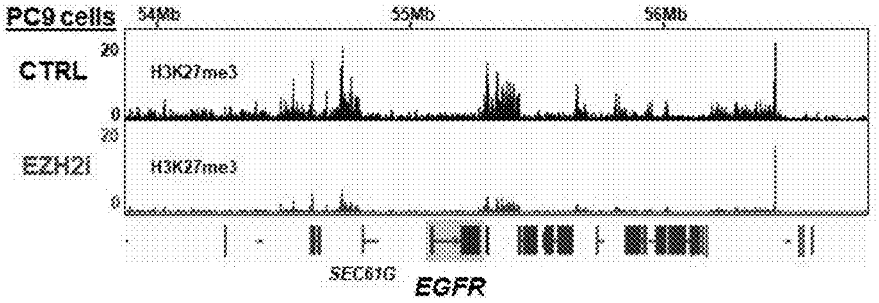
Figure 8I:
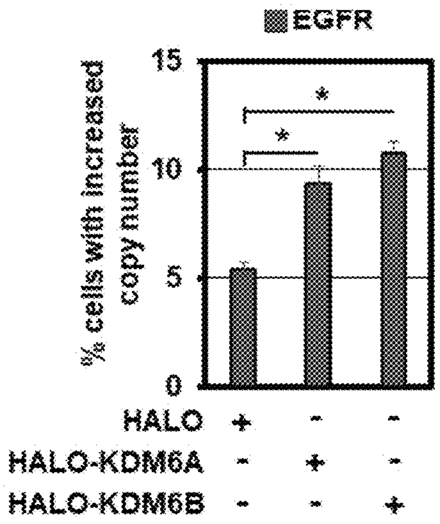

Using two independent siRNAs against EZH2 in RPE cells, we observed a significant increase in EGFR copy number while not changing copy number of other chr7 regions (FIG. 8C and FIG. 7G-7K). We further demonstrated that a specific EZH2 pharmacological inhibitor (EZH2i—C24; (45)) was able to promote EGFR amplification in a dose-dependent manner while not altering copy number of other loci in RPE cells (FIG. 8D, 8E and FIG. 11L,11M). EGFR copy number was also increased in colorectal cancer cell lines that have either low (HCT-15) or high (HT-29) EGFR copy number when treated with the EZH2i (FIG. 7N-7Q). Furthermore, removing EZH2i from RPE cells (referred to as washout) allowed EGFR copy gains to return to baseline, which highlights their transient nature (FIG. 8F and FIG. 7M). At the higher doses of EZH2 inhibition, EZH2i also resulted in a higher number of copies within some of the copy gained nuclei and increased EGFR transcript (FIG. 8G), which phenocopies H3K27M transduced cells (FIG. 1F-1H). Furthermore, ChIP-seq analyses of PC9 cells (lung adenocarcinoma) treated with an EZH2 inhibitor (44) also showed a reduction in the H3K27me3 domains flanking EGFR (FIG. 8H). In order to further explore the importance of H3K27me3 in preventing the EGFR locus from amplifying, we overexpressed each of the H3K27 demethylases—KDM6A and KDM6B—individually and then conducted EGFR FISH (FIGS. 8I and 7R, 7S). In contrast to the specificity observed with KDM4 family members, both KDM6 members promoted EGFR copy gains (FIG. 8I). Taken together, these results demonstrate a critical role for H3K27 methylation and the associated enzymes in preventing the EGFR locus from undergoing amplification and expression.

Figure 7T:
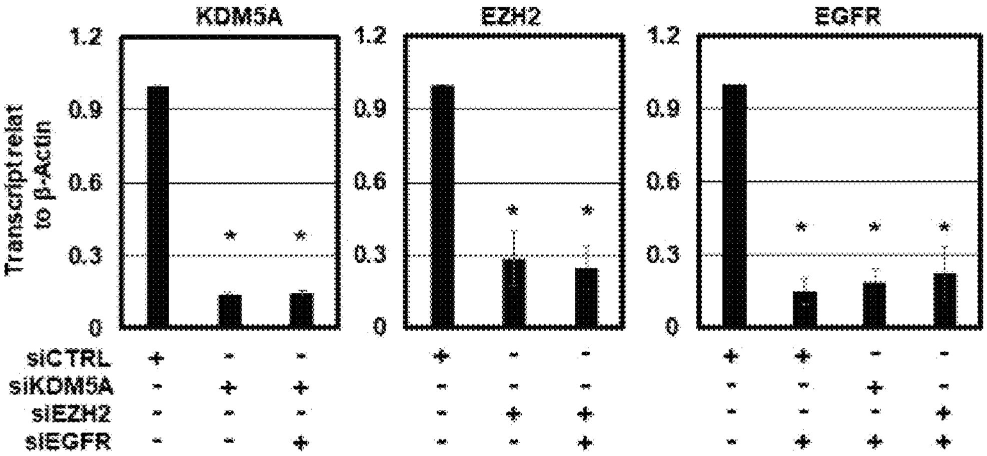
Figure 8J:
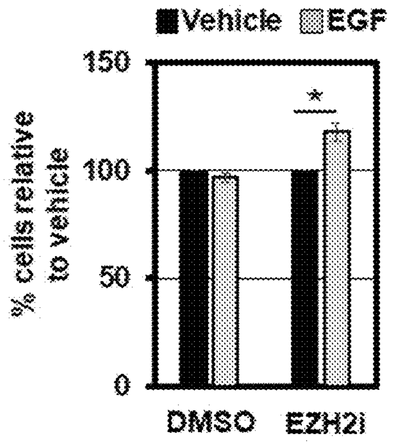
Figure 8K:
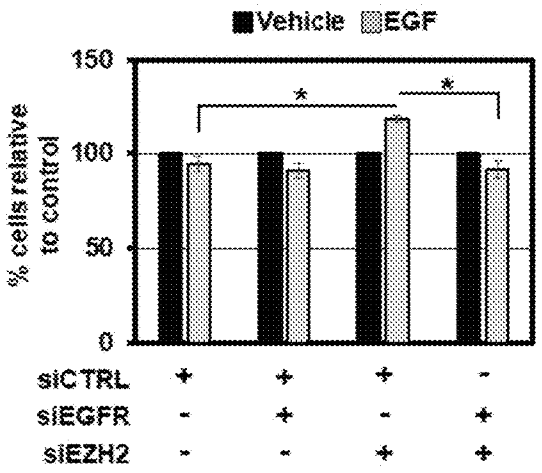

Since EZH2 inhibition promoted EGFR amplification and increased expression levels, we tested whether cells treated with the EZH2i or EZH2 siRNA depletion would respond differently to EGF supplementation. Specifically, cells were pre-treated with EZH2 inhibitor for 24 hours or depleted with two independent EZH2 siRNAs in order to promote increases in EGFR copy number before being supplemented with DMSO or EGF. Both EZH2 inhibitor and EZH2 siRNA treated cells demonstrated a significantly increased proliferation in response to exogenous supplementation with EGF compared to DMSO-treated cells (FIG. 8J, 8K). Moreover, EGFR/EZH2 siRNA co-depletion completely blocked the increased response to EGF (FIG. 8K and FIG. 7T). These data are consistent with a prior report noting that combined inhibition of EZH2 and EGFR were able to increase the sensitivity of colorectal cancer cells when compared to either drug alone (46). Our data suggest that this observation could be in part through EZH2i-induced EGFR DNA amplification. In support of this hypothesis, EZH2i treatment in two different colorectal cancer cell lines (HCT-15 and HT-29) resulted in increases in EGFR DNA copy number in these cells (FIG. 7N-7Q), which paralleled their sensitivity (46). Taken together, these data illustrate a critical role for K27 methylation, EZH2 and KDM6 in modulating EGFR locus amplification, expression, and in turn, cellular response to either EGFRi or growth factors.

H3K4 and H3K27 Methylation Controls EGFR Amplification

Figure 9A:
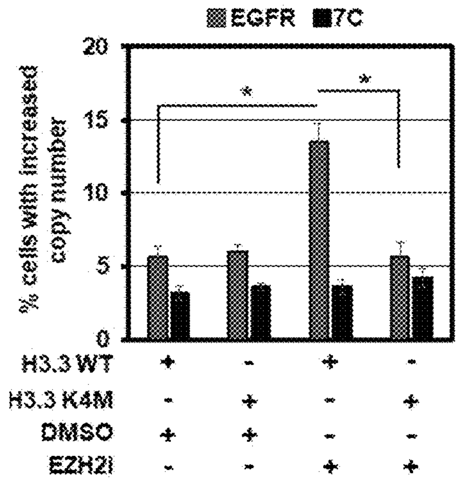
FIG. 9A-9U: H3K4/27 methylation controls EGFR amplification.
Figure 10A:
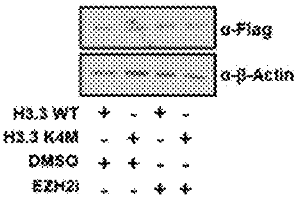
FIG. 10A-10V: H3K4/K27 methylation control EGFR amplification.
Figure 10B:
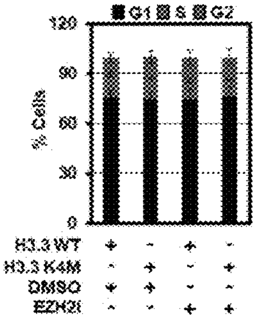
FIG. 10B) Cell cycle analysis of RPE cells in FIG. 10A.

In a recent study, we demonstrated that H3K4 methylation enrichment at specific genomic loci was sufficient to recruit KDM4 family members to chromatin, and in turn, promote copy number gains on chromosome 1 (e.g., 1q12h and 1p32.3; (10)). Upon evaluating H3K4mel/2/3 across the EGFR locus, we observed an inverse relationship between H3K4 methylation states and H3K27me3, which appears to flank the regions containing H3K4 methylation (FIG. 8B). Therefore, we hypothesized that inhibition of EZH2 promoted the KDM4A driven EGFR copy gains through H3K4 methylation. Consistent with this hypothesis, RPE cells transduced with H3.3 K4M did not generate EGFR copy gains upon EZH2 inhibition (FIG. 9A and FIG. 10A, 10B), which highlights the importance of this amino acid in promoting EGFR copy gains downstream of EZH2 depletion or inhibition. Furthermore, KDM4A was required for EZH2 depletion to generate EGFR amplification (FIG. 8C).

Figure 9B:
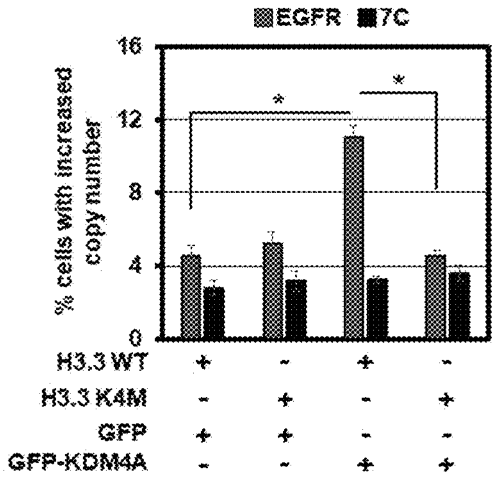
FIG. 9B) RPE cells transduced with H3.3 K4M completely inhibit GFP-KDM4A overexpression mediated DNA copy gains of EGFR.
Figure 9C:
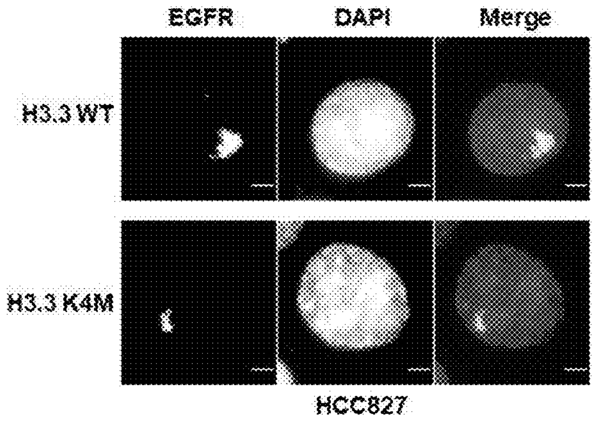
FIG. 9C) Representative DNA FISH images of HCC827 lung cancer cells transduced with H3.3 wild type (WT) or H3.3 K4M. EGFR (red) and DAPI (blue) are shown in merge.
Figure 9D:
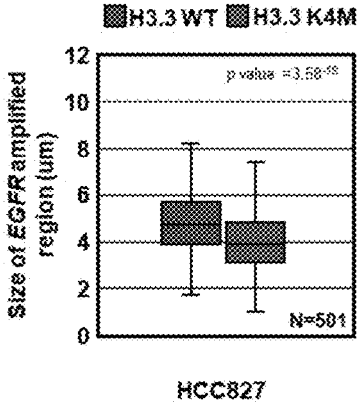
FIG. 9D) H3.3 K4M transduced HCC827 cells (red), reduces the size of EGFR amplified gene cluster clouds when compared to H3.3 WT transduced cells (blue).
Figure 9E:
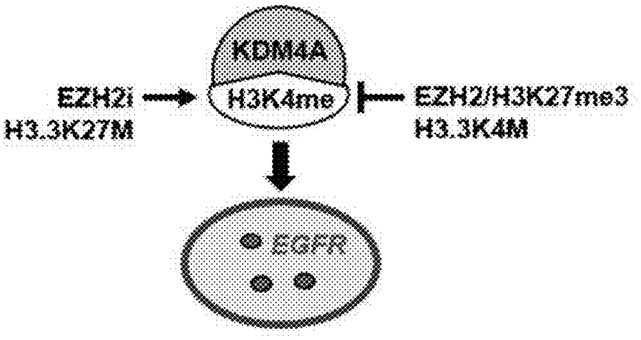
FIG. 9E) A model depicting the impact EZH2, H3K4M and H3K27M have on EGFR copy gains through KDM4A and H3K4 methylation based on the genetic experiments in FIG. 9A-9D.
Figure 10C:
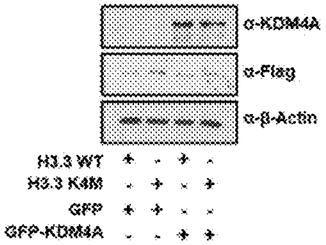
FIG. 10C) Immunoblot analysis of whole cell extracts from RPE cells validating expression of flag-tagged histone H3.3 wild type or K4M constructs and GFP-tagged KDM4A. β-Actin was used as a loading control.
Figure 10D:
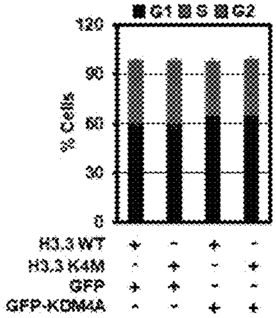
FIG. 10D) Cell cycle analysis of RPE cells in FIG. 10C.
Figure 10E:
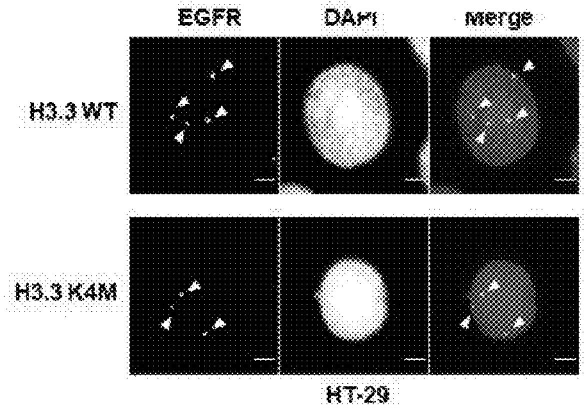
FIG. 10E) Representative DNA FISH images of HT-29 nuclei from cells transduced with H3.3 WT or H3.3 K4M. EGFR (red) and DAPI (blue) are shown in the merge. HT-29 K4M image.
Figure 10F:
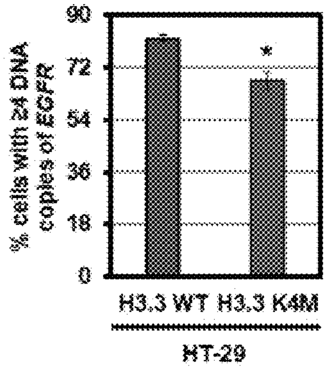
FIG. 10F) H3.3 K4M transduction significantly reduced the EGFR DNA copy number in HT-29 when compared to H3.3 WT transduced HT-29 cells.

Since H3K4 methylation is key to KDM4A binding and copy gain generation at other specific sites in the genome (10,18), we also tested whether H3K4M would block KDM4A promoted EGFR copy gains. Indeed, H3K4M blocked KDM4A driven EGFR amplification (FIG. 9B and FIG. 10C, 10D). Consistent with these observations, HCC827 cells containing the EGFR amplification clouds that were reduced in size upon KDM4A depletion and inhibition (FIG. 5) also had a significant reduction EGFR cloud size with H3K4M transduction (FIG. 9C, 9D). A similar reduction was also observed with H3K4M transduction in the HT-29 cells that contain EGFR copy gains (FIG. 10E, 10F). Furthermore, the Tudor domains that recognize H3K4 methylation within KDM4A (39) were required to generate EGFR copy gains (FIG. 4B). Taken together, these data collectively emphasize the importance of H3K4 methylation for generating the EGFR amplifications and highlight the need to balance K4/27 methylation states in order to modulate EGFR copy gains through KDM4A (FIG. 9E).

Figure 9F:
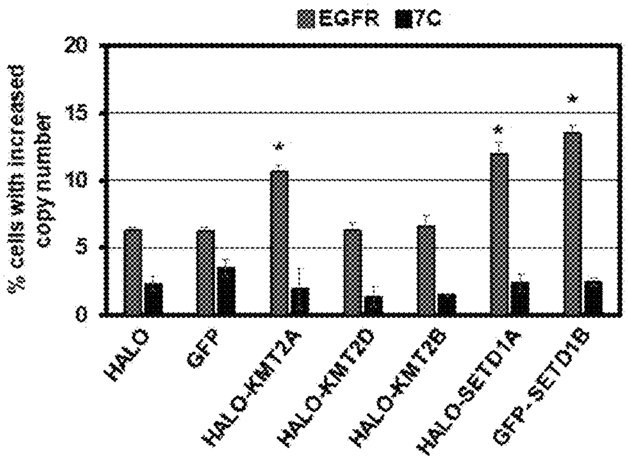
FIG. 9F) Transient overexpression of HALO-tagged KMT2A and SETD1A as well as GFP-tagged SETD1B promote EGFR DNA copy gains in RPE cells.
Figure 9G:
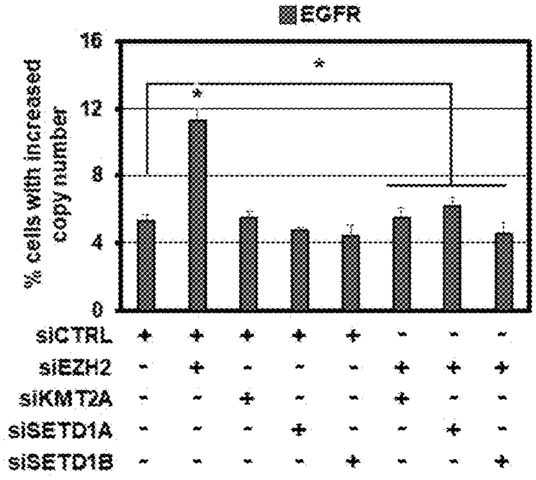
FIG. 9G) siRNA-mediated co-depletion of KMT2A, SETD1A or SETD1B with EZH2 completely blocks EZH2-depletion mediated EGFR copy gains in RPE cells.
Figure 9H:
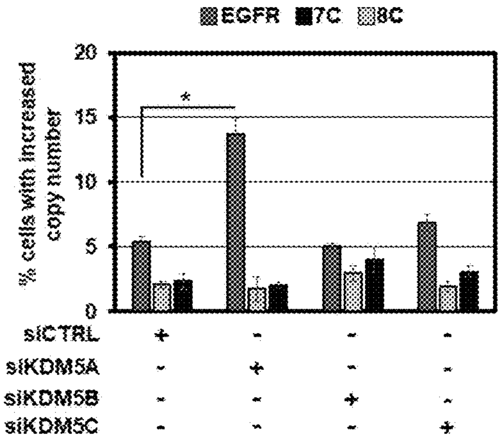
FIG. 9H) siRNA-mediated depletion of the H3K4 tri-demethylase KDM5A promoted EGFR copy number gains.
Figure 10G:
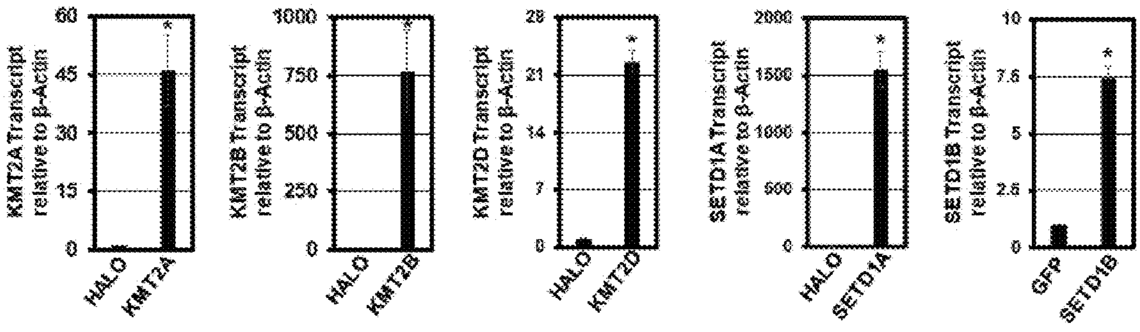
FIG. 10G) qRT-PCR analysis of H3K4 methyltransferase family transcripts in RPE cells transiently transfected with HALO-tagged KMT2A, KMT2B, KMT2D, SETD1A or GFP-tagged SETD1B. Cells were harvested 24 hours post DNA transfection.
Figure 10H:
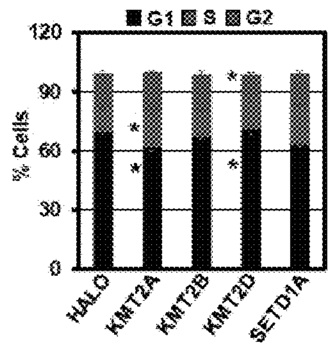
FIG. 10H-10I) Cell cycle analysis of RPE cells in FIG. 10G.
Figure 10I:
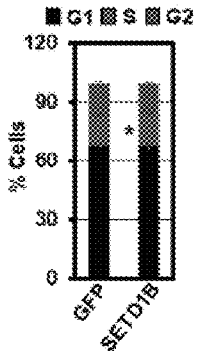
Figure 10J:
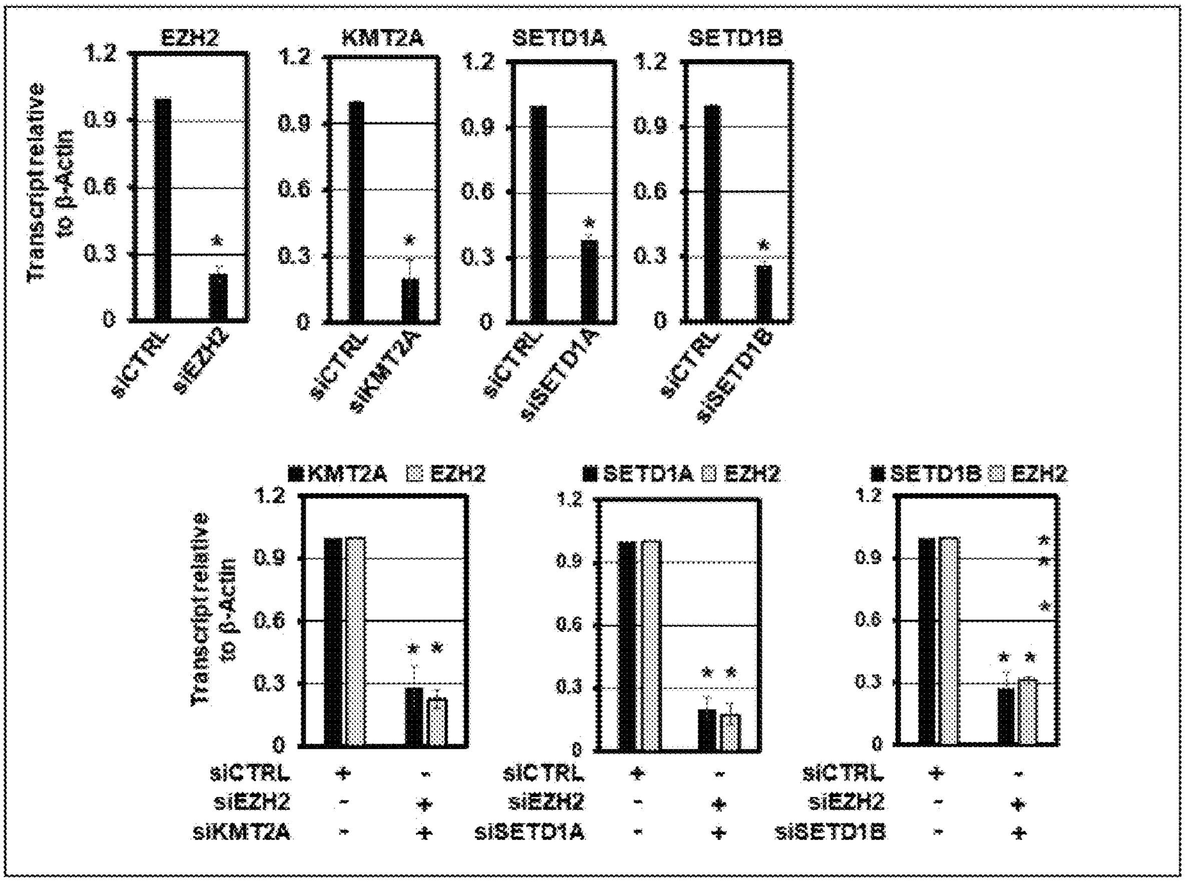
FIG. 10J) qRT-PCR analysis of RPE cells treated with siRNAs to EZH2, KMT2A, SETD1A and SETD1B, alone or in combination. Cells were harvested 72 hours post siRNA transfection.
Figure 10K:
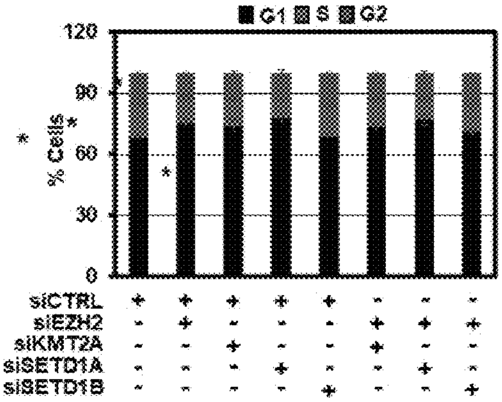
FIG. 10K) Cell cycle analysis of RPE cells in FIG. 10J.

H3K4 KMTs were recently shown to be important in controlling the predilection of regions to amplify downstream of KDM4 members. For example, overexpression of each KMT2 family member promoted copy gains of specific chromosome 1 TSSG loci (10). Therefore, we overexpressed each H3K4 KMT (MLL1/KMT2A, MLL2/KMT2B, MLL4/KMT2D, SETD1A and SETD1B; (47)) to determine whether all or select KMTs promote EGFR amplification (FIG. 10G-10I). Only KMT2A, SETD1A and SETD1B were able to significantly promote EGFR copy gains (FIG. 9F). To date, the EGFR loci was the only target identified for SETD1A. Since EZH2 and the MLL family of KMTs oppose one another and their associated methylation states (48), we tested whether EGFR amplifications that occur downstream of EZH2 depletion are dependent on these H3K4 KMTs. When EZH2 and each KMT2 member (KMT2A, SETD1A, SETD1B) were co-depleted, the EGFR copy gains were blocked, which highlights the importance of H3K4 methylation upon EZH2 depletion (FIG. 9G and FIG. 10J, 10K).

Figure 9I:
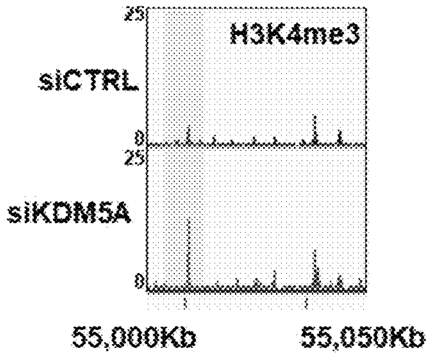
FIGS. 9I-9M) Candidate control intergenic locus in the vicinity of the EGFR region. Input-normalized ChIP-seq tracks of H3K4me3 density near the locus (chr7:55Mbp, highlighted) in cells with siKDM5A, shMLL (49), shEZH2 (50), and KDM4A overexpression, and H3K9me3 density upon KDM4A overexpression (bottom tracks) compared to control (top tracks).
Figure 9J:
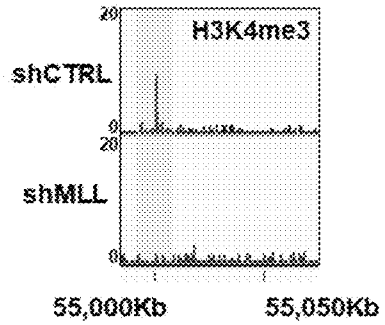
Figure 9K:
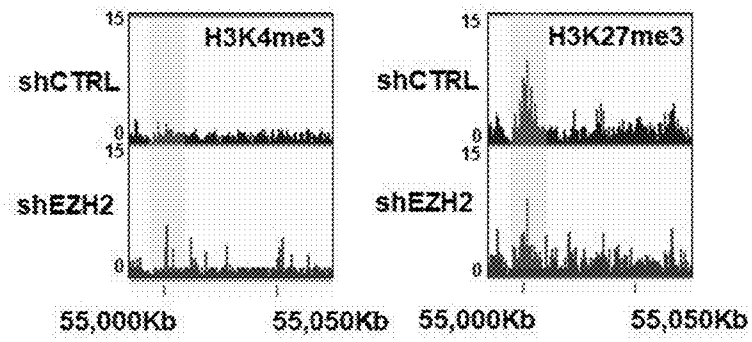
Figure 9L:
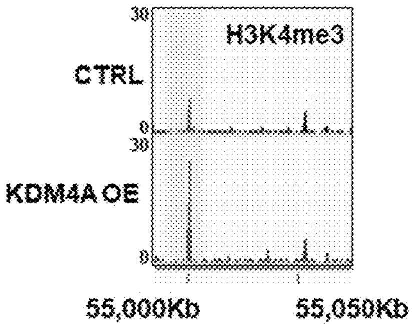
Figure 9M:
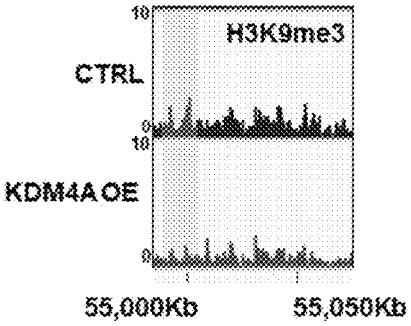
Figure 9N:
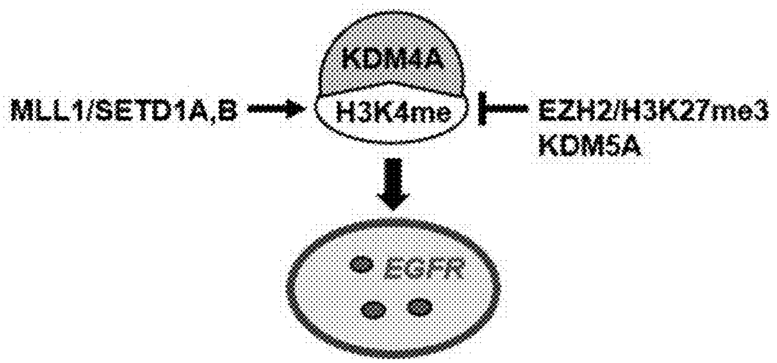
FIG. 9N) A model depicting the interplay between KMT2 enzymes (MLL1/SETD1A, B), KDM5A and EZH2 in regulating EGFR copy gains through KDM4A and H3K4 methylation based on the genetic and epigenomic experiments in FIG. 9F-9M.
Figure 9O:
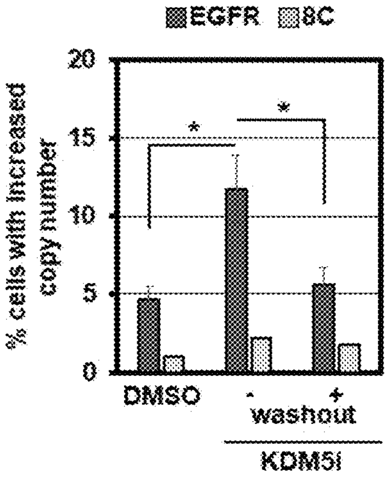
FIG. 9O) EGFR copy number gains returned to baseline 24 hrs after KDM5i (1 μM) removal (+ washout).
Figure 9P:
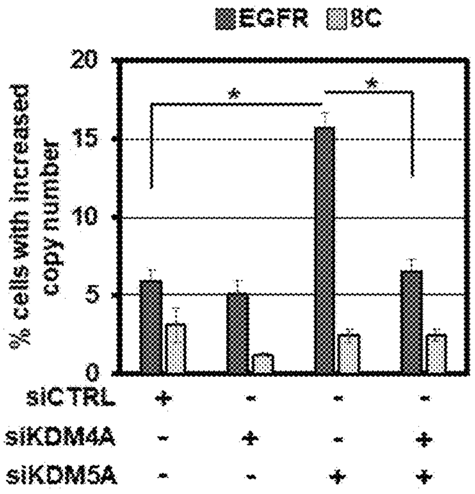
FIG. 9P) siRNA-mediated co-depletion of KDM4A with KDM5A, blocks KDM5A-depletion mediated EGFR copy gains.
Figure 9Q:
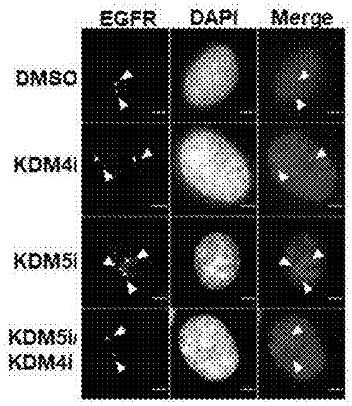
FIG. 9Q) Representative DNA FISH images of RPE nuclei from cells treated with KDM4i (MM), KDM5i (1 μM) or pre-treated with KDM4i (1 nM) followed by KDM5i (1 μM) treatment. EGFR (red), DAPI (blue) and merge are shown.
Figure 9R:
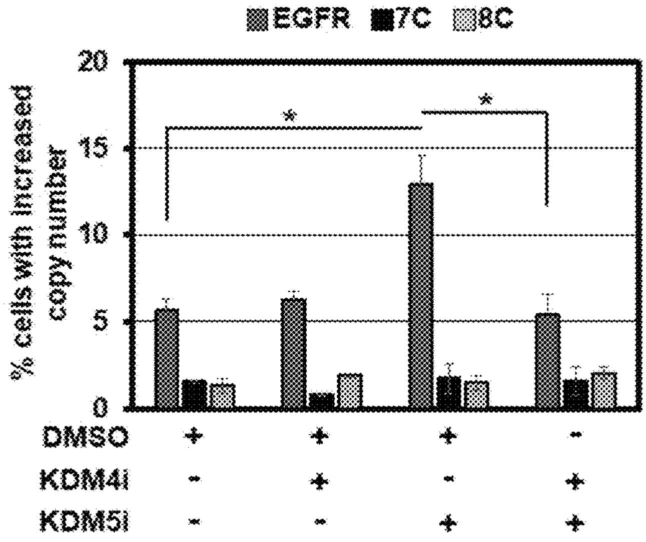
FIG. 9R) A 24 hour pre-treatment of RPE cells with KDM4i (1 nM) completely blocked KDM5i-mediated DNA copy gains of EGFR.
Figure 9S:
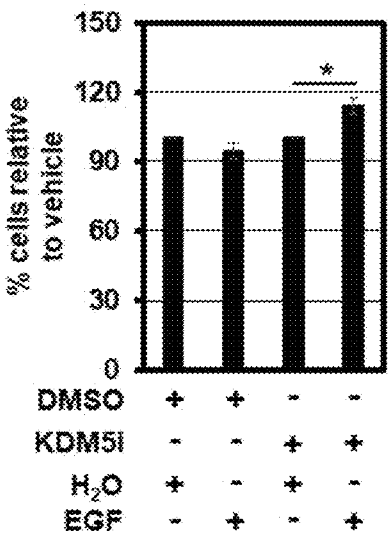
FIG. 9S) RPE cells pre-treated with KDM5i (1 μM) for 24 hours proliferate faster in response to a 24 hour stimulation with 50 ng/ml EGF (compared to the respective vehicle control).
Figure 10L:
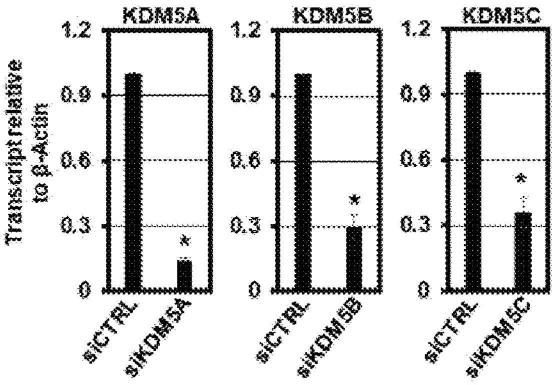
FIG. 10L) qRT-PCR analysis of RPE cells treated with siRNAs targeting the KDM5 family. Cells were harvested 72 hours post siRNA transfection.
Figure 10M:
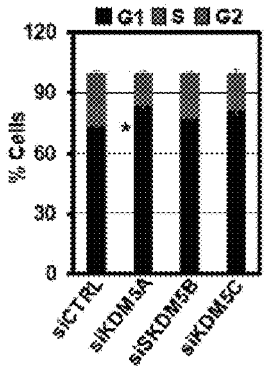
FIG. 10M) Cell cycle analysis of RPE cells in FIG. 10L.
Figure 10N:
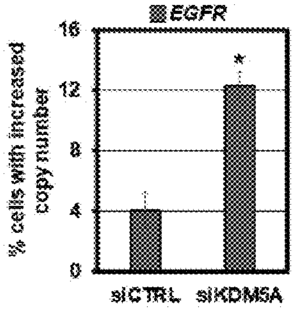
FIG. 10N) siKDM5A treated RPE cells had a significant increase in EGFR copy number.
Figure 10O:
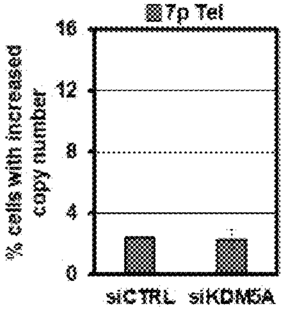
FIG. 10O) siKDM5A treated RPE cells did not have a significant change in 7p tel copy number.
Figure 10P:
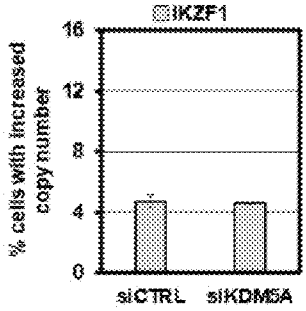
FIG. 10P) siKDM5A treated RPE cells did not have a significant change in IKZF1 copy number.

Since specific H3K4 KMTs controlled EGFR amplification, we tested whether the same was true for the H3K4 KDMs. The KDM5 enzymes are H3K4 tri-demethylases and have been shown to impact other TSSG sites (10). Depletion of the H3K4 tri-demethylases will increase H3K4 methylation, thereby promoting copy gains of EGFR if copy gains of this locus are indeed dependent on H3K4 methylation. Therefore, we depleted each KDM5 member with at least two independent siRNAs before conducting cell cycle profiles and EGFR FISH (FIG. 10L, 10M). Only KDM5A depletion generated EGFR copy gains, while other genomic loci were unaffected (FIG. 9H and FIG. 10N-10P; (10)). Consistent with these genetic experiments, we observed enrichment for H3K4me3 upon ChIP-seq at an intergenic region within the EGFR structural domain that is 87 Kb upstream of the EGFR transcription start site (TSS) (FIG. 9I, blue shaded region). Furthermore, we observed a loss of this H3K4me3 peak upon shMLL1 treatment in a published dataset (FIG. 9J; (49)) and enrichment upon shEZH2 treatment in a public dataset that was accompanied with reduced H3K27me3 (FIG. 9K; (50)). Moreover, RPE cells that overexpress KDM4A exhibited increases in H3K4me3 as well as a reduction in H3K9me3 at this same region (FIG. 9L, 9M, respectively). Taken together, these data suggest that KMT2 enzymes, KDM5A and EZH2 modulate the balance of H3K4/27 methylation at the EGFR locus, and in turn, EGFR copy gains (FIG. 9N).

Our studies suggest that promoting H3K4 methylation through KDM5A depletion or inhibition would promote EGFR amplification through KDM4A. First, we evaluated the impact of KDM5 inhibitor (KDM5i) treatment on EGFR amplification (KDM5i-C70; (51,52)). KDM5i treatment promoted EGFR copy gains, however, they returned to baseline upon KDM5i washout (FIG. 9O and FIG. 10Q), which emphasizes the reversibility of the amplifications as observed with EZH2i washout. We then used both genetic and chemical inhibition of KDM4 enzymes (KDM4i; (43)) to determine whether this would block EGFR amplifications generated upon either KDM5A siRNA depletion or KDM5i treatment (FIG. 9β-9R and FIG. 10R-10U). In fact, the use of KDM5 and KDM4 inhibitors can be used to generate and prevent EGFR copy gains (FIG. 9Q, 9R), which highlights plasticity of the copy gains and the ability to therapeutically control DNA amplification with drugs targeting epigenetic factors.

Figure 9T:
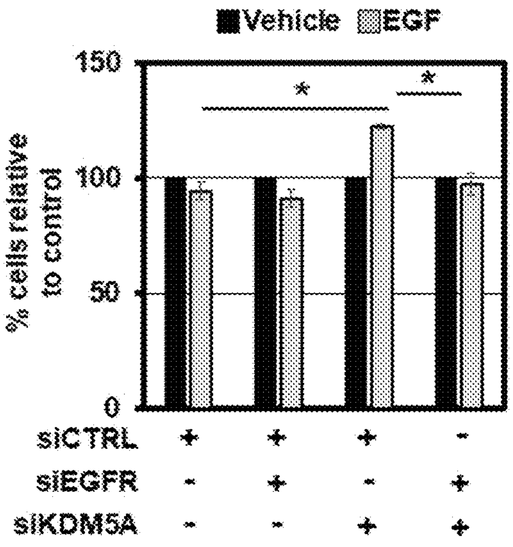
FIG. 9T) KDM5A depleted RPE cells proliferate faster in response to a 24 hour stimulation with 50 ng/ml EGF (compared to KDM5A-depleted cells treated with vehicle), which was rescued by co-depletion of EGFR.
Figure 9U:
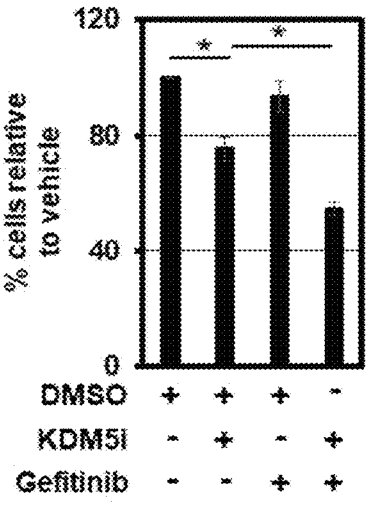
Figure 10Q:
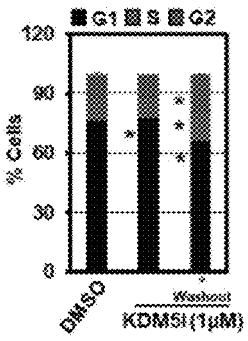
FIG. 10Q) Cell cycle analysis of RPE cells treated with KDM5i (1 μM) and following drug removal and replenishment with complete DMEM.
Figure 10R:
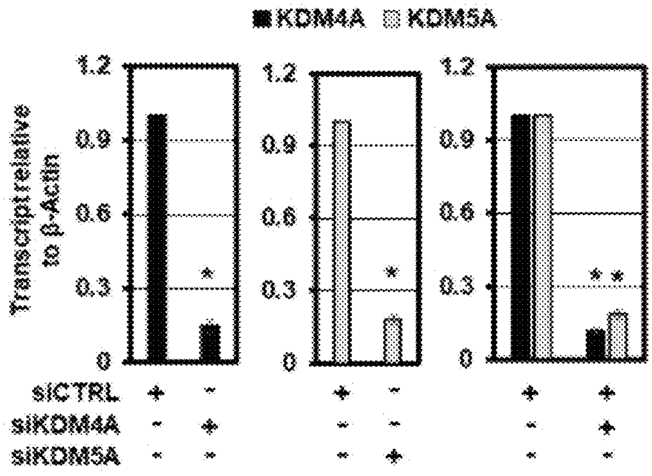
FIG. 10R) qRT-PCR analysis of RPE cells treated with siRNAs targeted to KDM4A or KDM5A, alone or in combination. Cells were harvested 72 hours post siRNA transfection.
Figure 10S:
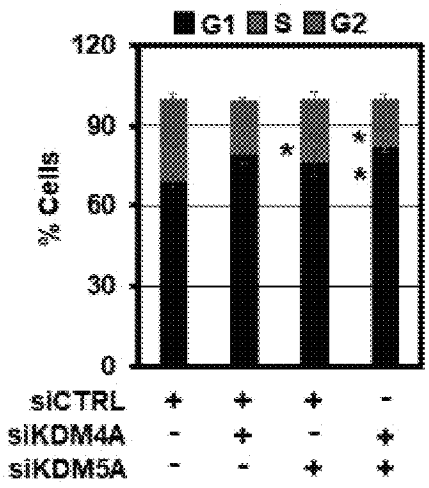
FIG. 10S) Cell cycle analysis of RPE cells in FIG. 10R.
Figure 10T:
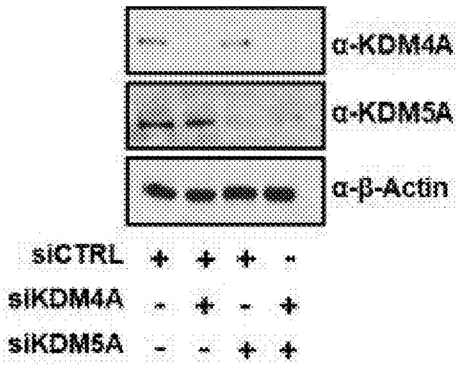
FIG. 10T) α-KDM4A and α-KDM5A immunoblot analysis of siRNA treated RPE cells from FIG. 12O. (β-Actin was used as a loading control.
Figure 10U:
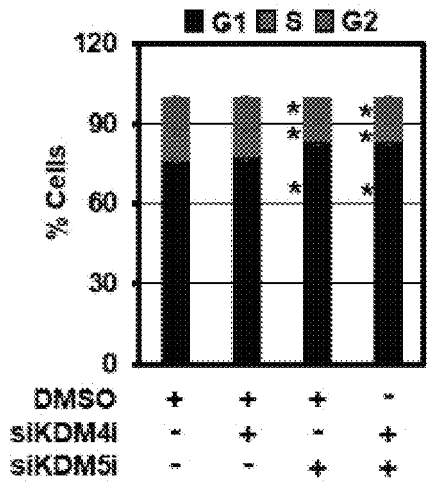
FIG. 10U) Cell cycle analysis of RPE cells treated with KDM4i (1 nM) and KDM5i (1 μM) alone or in combination. Cells were pre-treated with KDM4i for 24 hours followed by a second treatment in combination with KDM5i (24 hours later). Cells were harvested 48 hours after combination treatment.
Figure 10V:
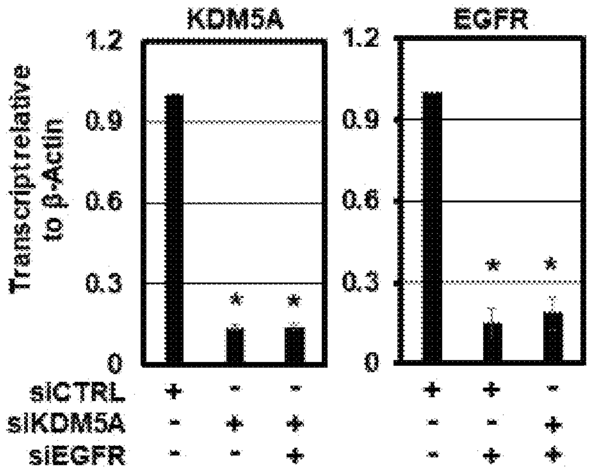

Having therapeutic control of key growth factor receptors could have a profound impact on the ability to control cell proliferation and drug response when delivering inhibitors. Therefore, we tested whether KDM5i would alter cell proliferation when treated with supplemental EGF. Consistent with the previous experiments demonstrating that factors promoting EGFR copy gains increased EGF associated proliferation, KDM5i increased cell proliferation with supplemented EGF when compared to KDM5i alone (FIG. 9S), which was also observed with KDM5A siRNA depletion, and in turn, was blocked with EGFR siRNA depletion (FIG. 9T and FIG. 10V). Lastly, we were also able to demonstrate that KDM5i increased the sensitivity to Gefitinib when compared to KDM5i alone (FIG. 9U), which was consistent with a previous report (53). Taken together, these data highlight the ability to modulate H3K4 methylation in order to harness control of EGFR DNA copy levels, and in turn, growth factor and drug response.

Hypoxia and Epidermal Growth Factor Induce EGFR Amplification

Figure 11A:
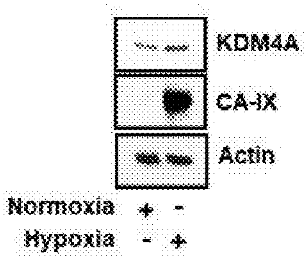
FIG. 11A-11M: Hypoxia and EGF induce EGFR amplification.
Figure 11B:
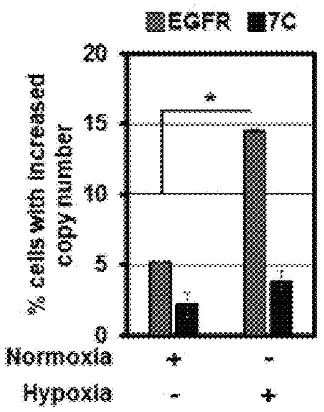
Figure 11C:
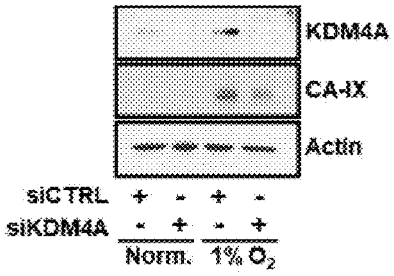
Figure 11D:
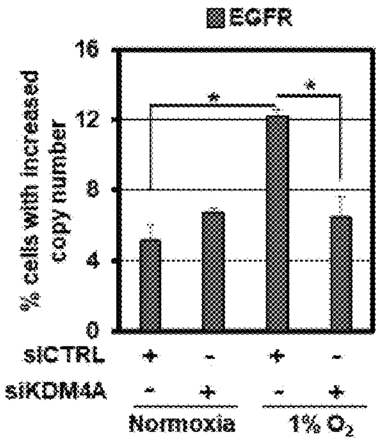
Figure 11E:
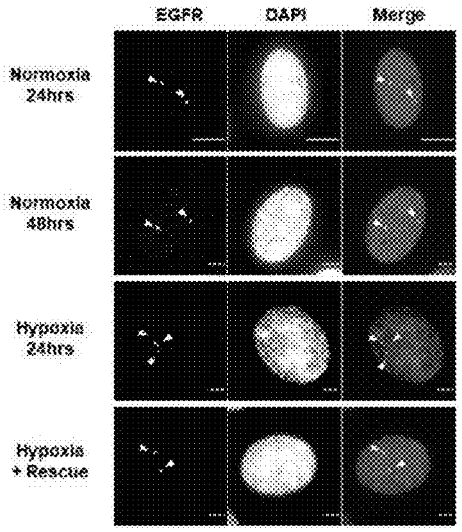
Figure 11F:
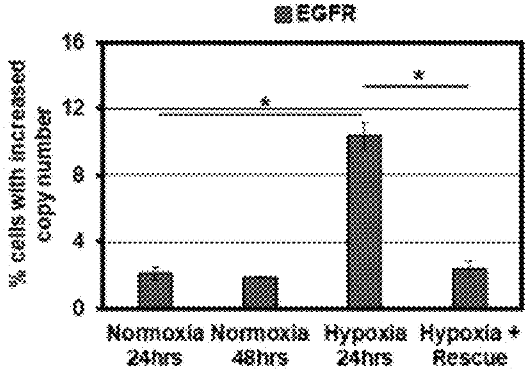
Figure 11G:
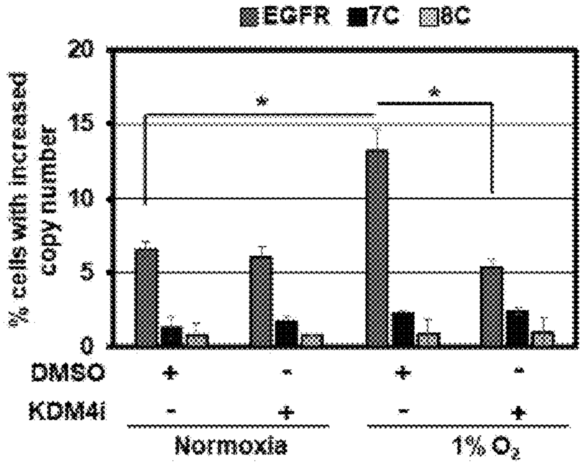
Figure 11H:
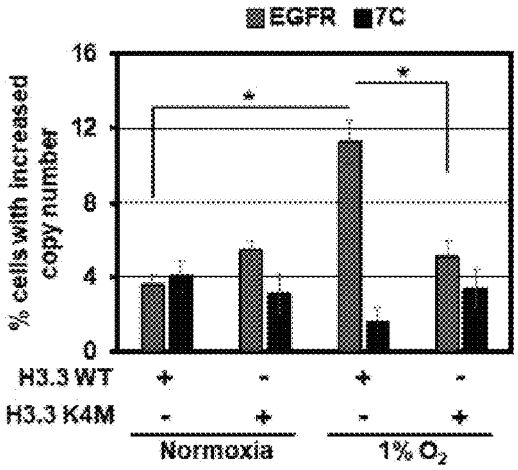
Figure 12A:
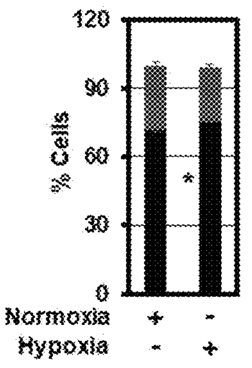
FIG. 12A-12O: Hypoxia and EGF induce EGFR amplification.
Figure 12B:
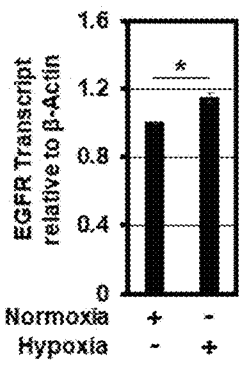
FIG. 12B) qRT-PCR analysis for EGFR transcript levels in RPE cells cultured in normoxia or hypoxia (1% O2) for 24 hours.
Figure 12C:
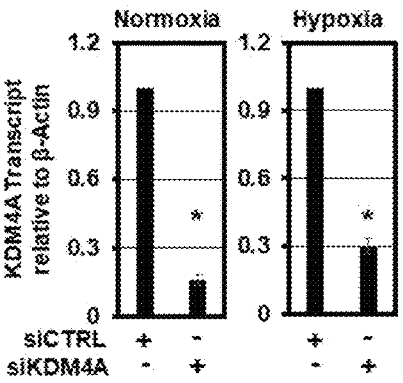
FIG. 12C) qRT-PCR analysis of RPE cells treated with siRNA targeted to KDM4A. 48 hours post siRNA transfection, cells were transferred to hypoxic culture conditions (1% O2) for 24 hours.
Figure 12D:
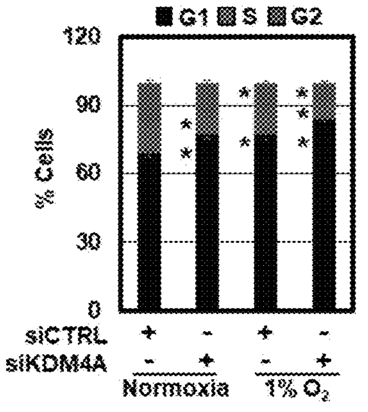
FIG. 12D) Cell cycle analysis of RPE cells in FIG. 12C.
Figure 12E:
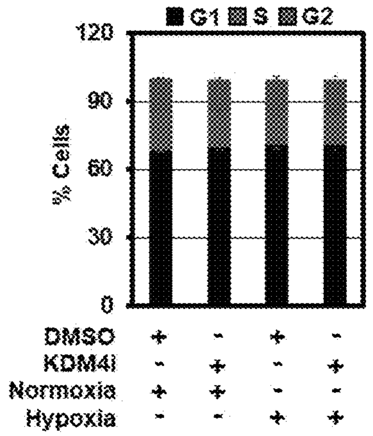
FIG. 12E) Cell cycle analysis of RPE cells-pre-treated with KDM4i (1 nM) for 24 hours, before a second treatment (1 nM) followed by immediate transfer to hypoxic culture conditions (1% O2) for 24 hours.
Figure 12F:
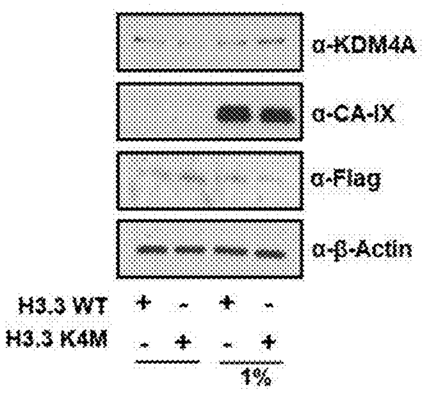
FIG. 12F) Immunoblot analysis of α-KDM4A, α-Flag, α-CA-IX and α-β-Actin, validating expression of histone H3.3 wild type or K4M constructs from whole cell extract in RPE cells. KDM4A and CA-IX immunoblot analysis is used to validate hypoxic culture conditions and j-Actin is used as a loading control.
Figure 12G:
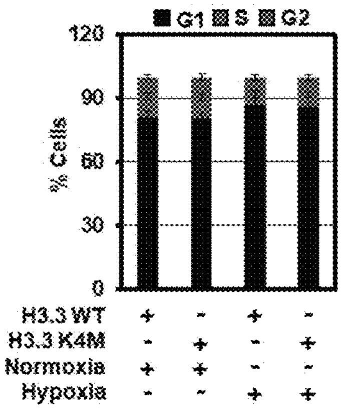
FIG. 12G) Cell cycle analysis of RPE cells in FIG. 12F. FIG.
Figure 12H:
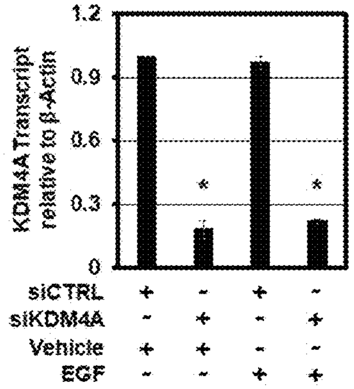
FIG. 12I) Cell cycle analysis of RPE cells in FIG. 12H.
FIG. 12J) Cell cycle analysis of RPE cells pre-treated with KDM4i (1 nM) for 24 hours, followed by a second 1 nM treatment and EGF treatment (50 ng/ml) for 24 hours.
FIG. 12K) Immunoblot analysis verifying expression of histone H3.3 wild type and K4M constructs from whole cell extracts of RPE cells. 24 hours after viral transduction, cells were treated with 50 ng/ml EGF. β-Actin is used as a loading control.
FIG. 12L) Cell cycle analysis of RPE cells in FIG. 12K.
FIG. 12M) qRT-PCR analysis of RPE cells treated with siRNAs targeted to KMT2A, SETD1A or SETD1B. 48 hours post siRNA transfection cells were treated with 50 ng/ml EGF or DMSO as a vehicle control, for 24 hours.
FIG. 12N) Cell cycle analysis of RPE cells in FIG. 12M.
Figure 12I:
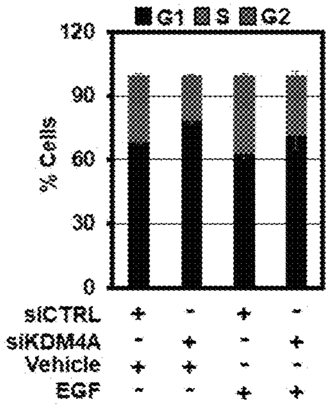
Figure 12J:
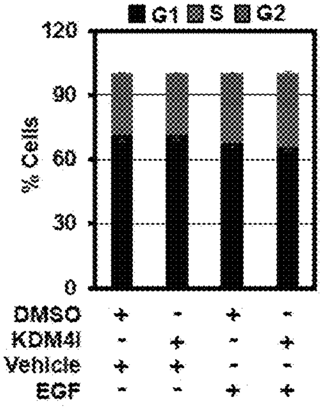

Previous work from our laboratory demonstrated that hypoxia directly promoted TSSG formation of chromosome 1 associated loci (e.g., 1q12h) via stabilization of the KDM4A protein, through reduced association with the SKP1-Cull-F-box (SCF) ubiquitin ligase complex (17). Consistent with this previous observation, 24 hours of exposure to hypoxia was able to stabilize KDM4A in RPE cells (FIGS. 11A, 11C) and promote EGFR copy gains that required KDM4A (FIGS. 11B-11D and FIGS. 12A-12D). The hypoxia-induced copy gains of EGFR were transient in nature, in a similar manner to those observed with KDM5i and EZH2i. Indeed, moving cells back to normoxia following 24 hours of hypoxia exposure completely restored EGFR copy number to baseline levels (FIGS. 11E, 11F). In agreement with the observation that KDM4A is required for hypoxia-induced EGFR DNA copy gains, pre-treatment of cells with KDM4 family inhibitor prior to hypoxic exposure also blocks hypoxia-induced EGFR copy gains (FIG. 11G and FIG. 12E). Furthermore, H3.3 K4M mutant expressing cells did not generate the hypoxia-induced EGFR amplifications (FIG. 11H and FIGS. 12F, 12G). Taken together, these data demonstrate that hypoxia promotes EGFR copy gains in a similar fashion to KDM4A overexpression in that the amplifications require increased KDM4A levels and proper targeting via H3K4 methylation (see FIG. 12O).

Figure 11I:
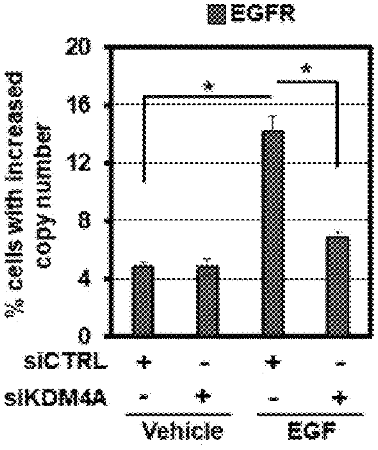
Figure 11J:
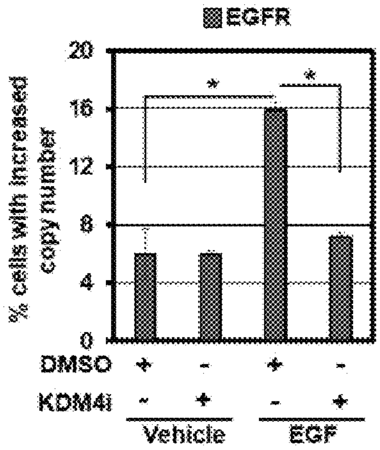
Figure 11K:
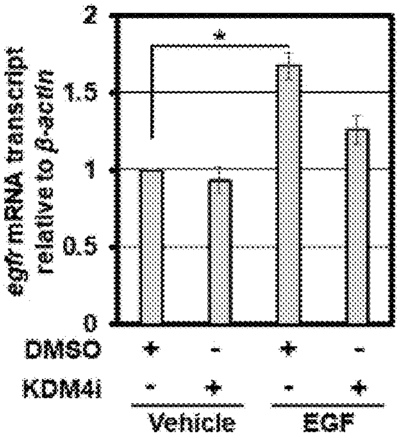

While investigating hypoxia modulation of EGFR amplification, we also tested whether EGF supplementation would impact EGFR copy gains. A recent report demonstrated that cancer cells with EGFR amplification required EGF supplementation in the media to propagate the copy gains, which raised the possibility that EGF could directly promote EGFR copy gains (54). Consistent with this possibility, we demonstrated that treating cells for 24 hours with 50 ng/ml EGF, the preferred ligand of EGFR, results in significant copy number gains of the EGFR locus (FIG. 11I, 11J). Furthermore, these gains were entirely dependent on KDM4A as both siRNA-mediated depletion and pharmacological inhibition of the KDM4 family was able to completely suppress these gains (FIG. 11I, 11J and FIG. 12H-12J). We also observed increased EGFR transcripts that were reduced upon KDM4 inhibition (FIG. 11K). Even though KDM4A was required for both the copy gains and increased expression, we did not observe increased KDM4A protein levels (see FIG. 14C), which suggest another pathway could be promoting KDM4A-dependent copy gains.

Figure 11L:
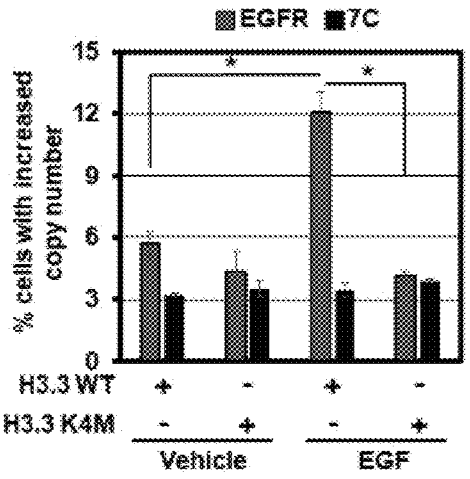
Figure 11M:
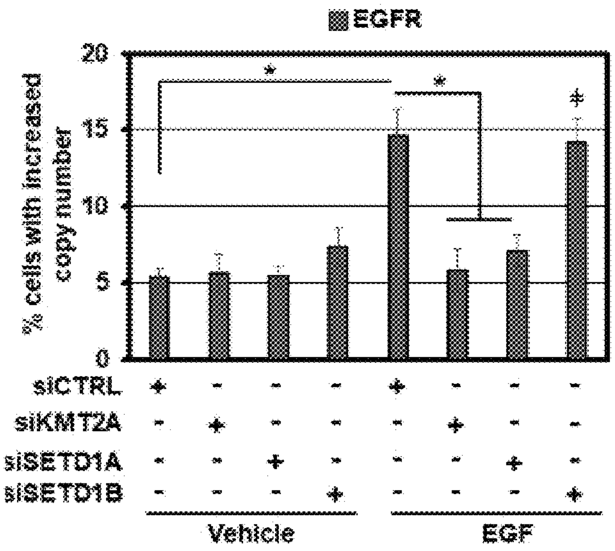
Figure 12K:
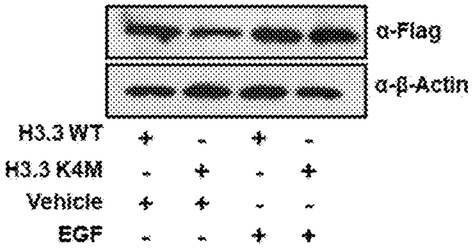
Figure 12L:
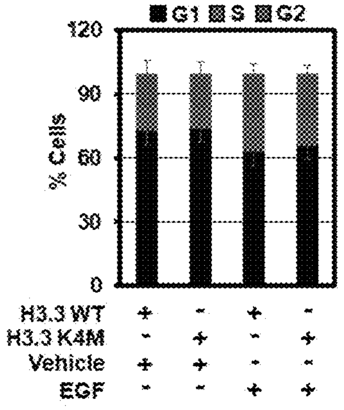
Figure 12M:
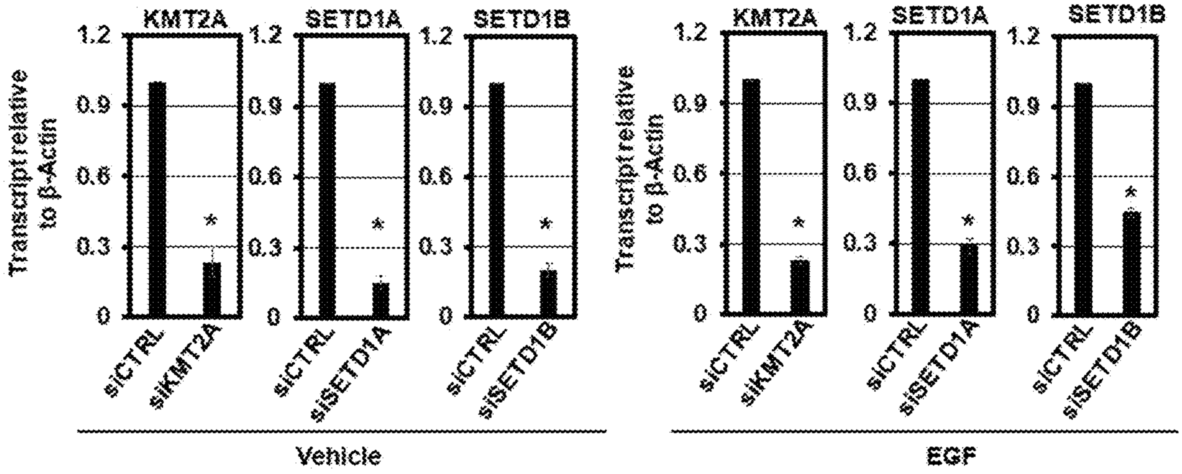
Figure 12N:
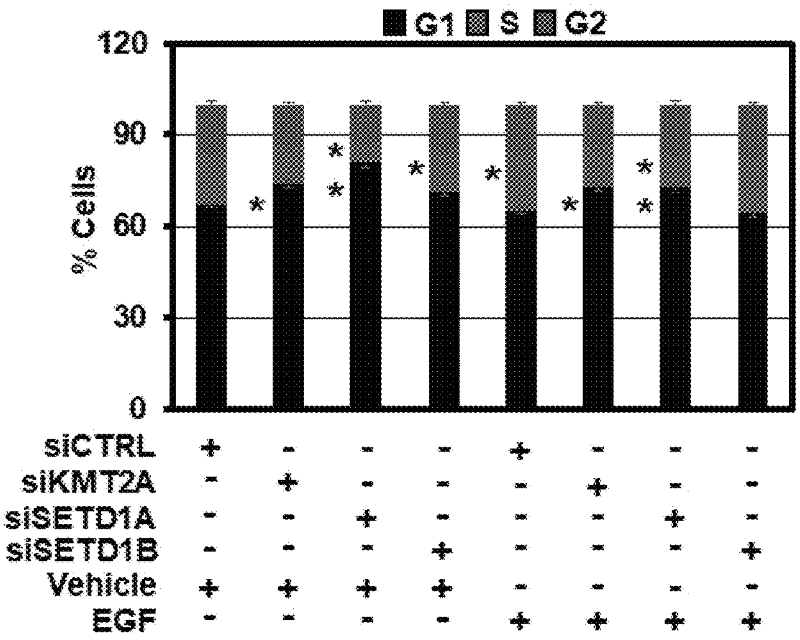
Figure 12O:
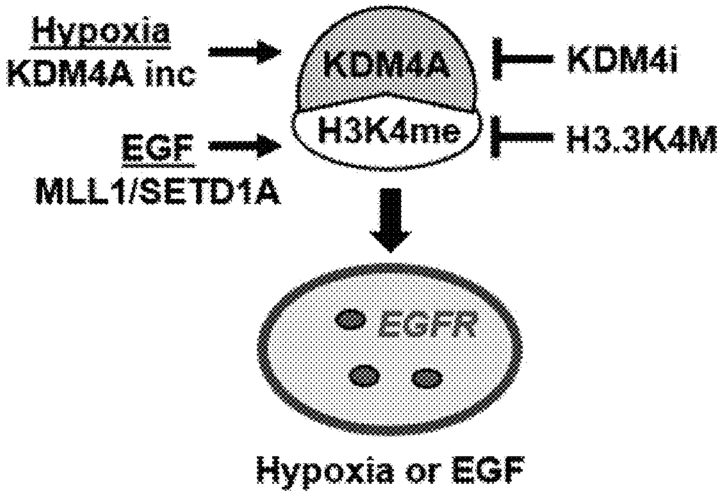

Given the importance of H3K4 methylation in targeting KDM4A so that TSSGs occur, we hypothesized that EGF was promoting the TSSGs via the H3K4 KMTs, and in turn, H3K4 methylation. Therefore, we first tested whether H3K4M would block EGF-induced EGFR copy gains. We observed that expression of the methyl-deficient H3K4M mutant was sufficient to block these growth factor-induced copy gains (FIG. 11L and FIG. 12K, 12L). Therefore, we then depleted with two independent siRNAs each of the H3K4 methyltransferases that generated amplification of the EGFR locus (KMT2A, SETD1A, SETD1B; FIG. 9F and FIG. 12M, 12N). Following depletion, cells were treated with EGF (50 ng/ml) for 24 hours and their EGFR copy number was assessed by DNA FISH. Depletion of KMT2A (MLL1) and SETD1A were able to completely inhibit EGF-induced copy gains of EGFR, whereas depletion of SETD1B had no impact on the amplifications (FIG. 11M). Thus, EGF treatment appears to promote EGFR copy gains through KMT2A, SETD1A and H3K4 methylation, which illustrates how extrinsic cues can promote selective copy gains via specific methyltransferases. Taken together, these data suggest that two different extrinsic cues (hypoxia and EGF) are promoting EGFR copy gains through similar but distinct epigenetic mechanisms (FIG. 12O).

Figure 13A:
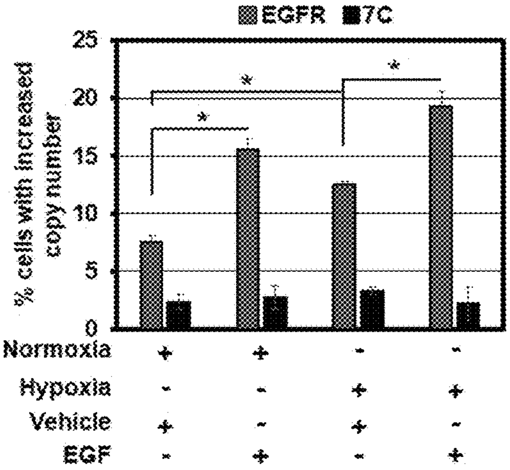
FIG. 13A-13F: Combination of epigenetic dysregulation, hypoxia and EGF induce higher EGFR amplification.
Figure 13B:
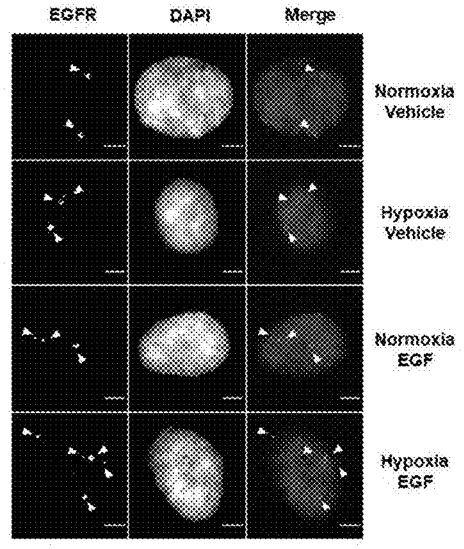
Figure 13C:
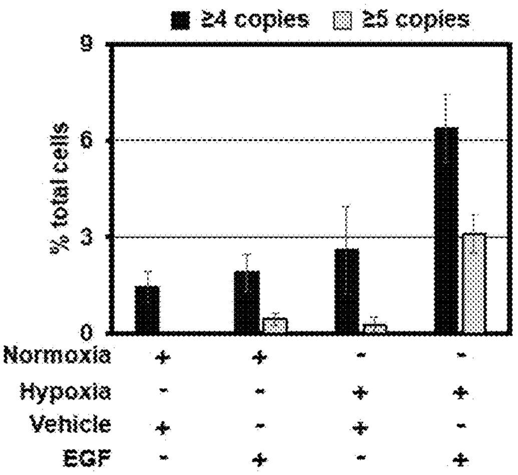
Figure 13D:
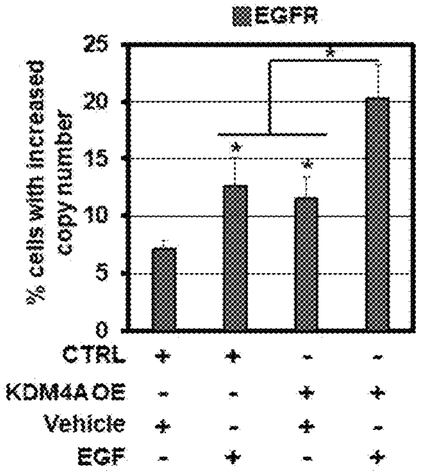
Figure 13E:
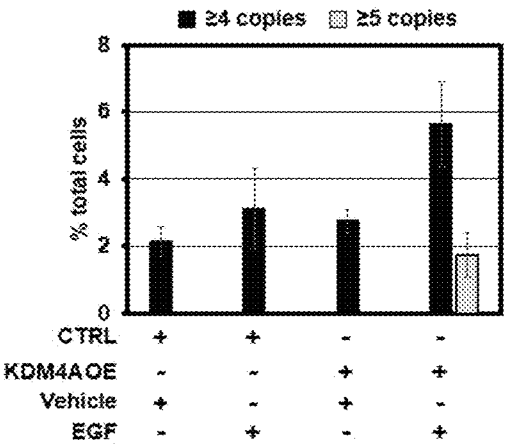
Figure 13F:
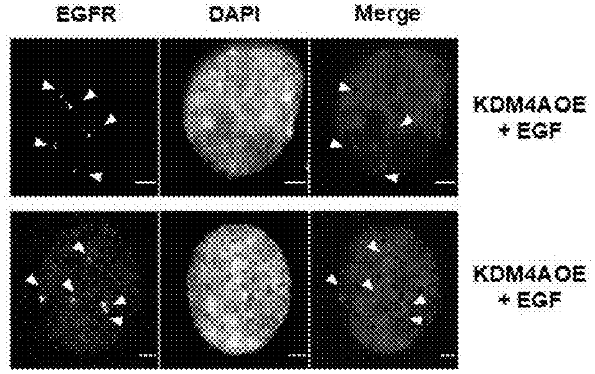
Figure 14A:
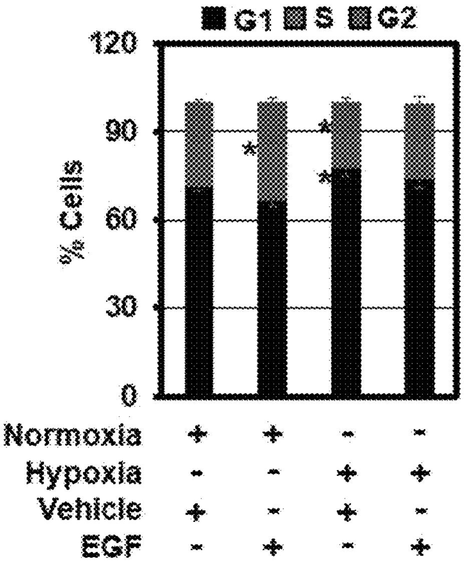
FIG. 14A-14I: Combining epigenetic dysregulation, hypoxia and EGF increased EGFR amplification.
Figure 14B:
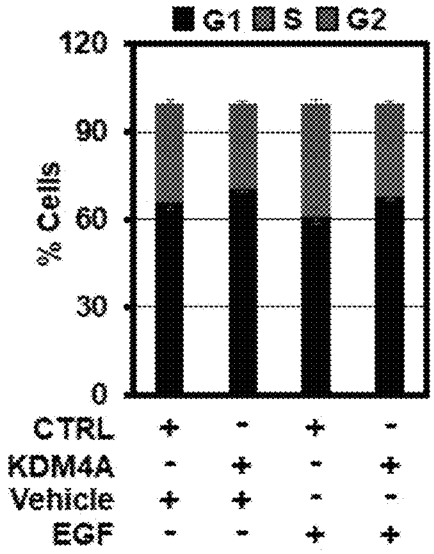
Figure 14C:
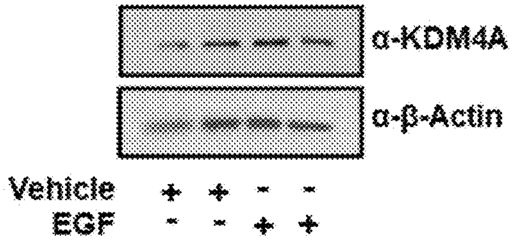
Figure 14D:
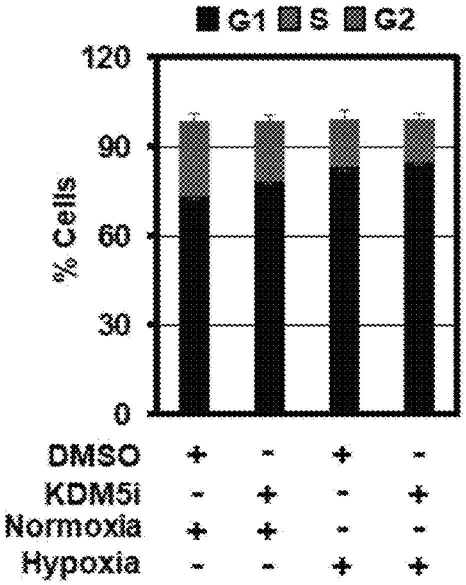
Figure 14E:
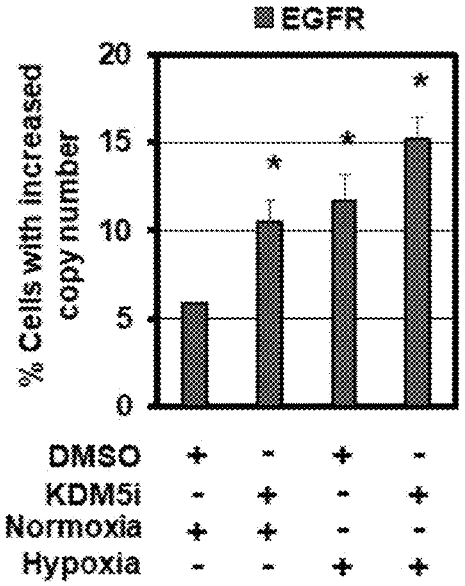
Figure 14F:
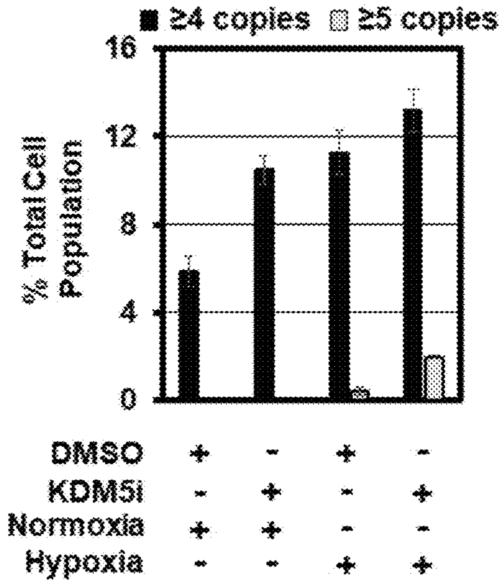
Figure 14G:
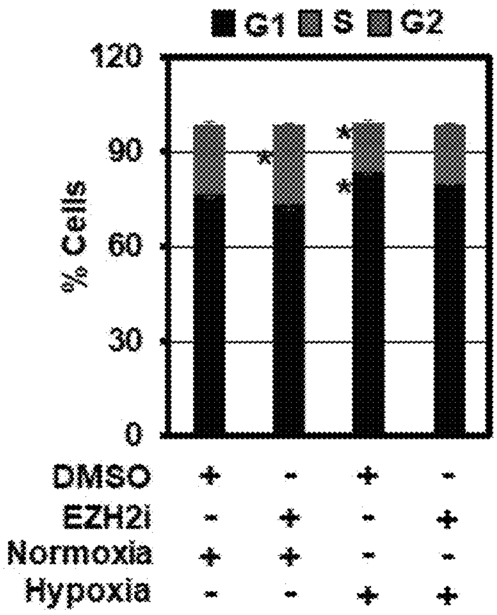
Figure 14H:
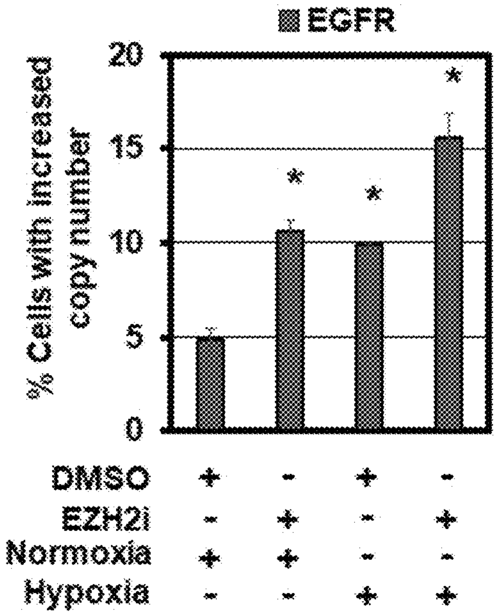
Figure 14I:
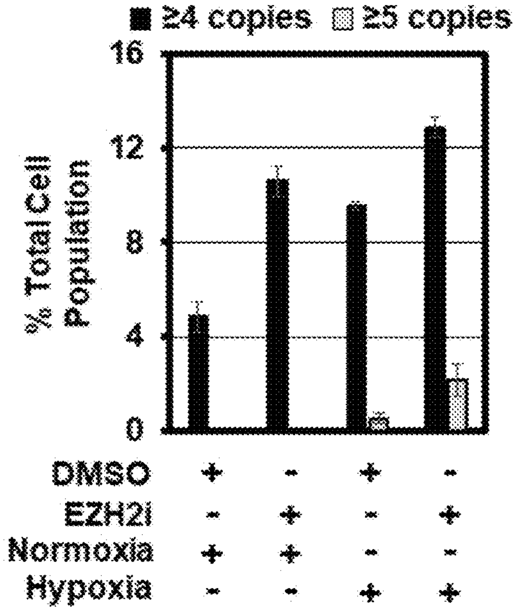

Epigenetic Dysregulation Combined with Hypoxia or Increased EGF Induce Higher EGFR Copy Number We have identified a network of chromatin regulators and physiological signals that influence EGFR copy gains. In the case of hypoxia, KDM4A stabilization mirrors overexpression and promotes EGFR amplification, while EGF appears to promote EGFR amplification through KMT2A/SETD1A and targeting KDM4A (FIG. 12O). Therefore, multiple extracellular cues could promote parallel triggers for the amplifications, which raises the question as to whether the combined signals elicit stronger amplification events. In order to test this possibility, cells were exposed to hypoxia for an initial 24 hours, followed by supplementation with EGF (50 ng/ml) under hypoxia conditions for an additional 24 hours. At this point, cells were harvested and their EGFR copy number assessed by DNA FISH. Hypoxia, in combination with EGF, resulted in a modest but additive increase in EGFR DNA copy number (FIG. 13A and FIG. 14A). Moreover, an increased percentage of these cells demonstrated higher EGFR DNA copies per nucleus (>5 copies;

FIG. 13B, 13C). This observation suggests that hypoxia-induced KDM4A stabilization in concert with EGF-stimulated increases in H3K4 methylation promote EGFR locus plasticity so higher DNA copy numbers are achieved. To strengthen this model, RPE cells that stably overexpress KDM4A, thus mimicking the phenotype observed upon hypoxic exposure, were also treated with EGF (FIG. 14B). EGF treatment of KDM4A overexpressing cells phenocopied the increase in EGFR amplification levels and increased DNA copies per nucleus that were observed in cells treated with hypoxia and EGF (FIG. 13A, 13D-13F). Moreover, in further support of this model, inhibition of KDM5 or EZH2, both of which increase H3K4me3 at the EGFR locus (FIG. 9I, 9K), enhance EGFR amplification when combined with hypoxic exposure (FIG. 14D-14I).

Taken together, our data supports a model by which physiological triggers such as increased EGF concentration and/or hypoxia function in combination with epigenetic perturbation to directly modulate chromatin states and determine whether site-specific low or high copy DNA amplifications occur.

Discussion

To date, little knowledge exists about the molecular mechanisms that promote specific oncogene amplifications. We have uncovered epigenetic regulators and physiologic cues that facilitate amplification of the oncogene EGFR. Moreover, we provide show the ability to rheostat an oncogenic amplification through therapeutic intervention. These data illustrate a molecular basis for EGFR amplification and establish that the extra cellular microenvironment can directly contribute to DNA amplification heterogeneity in both normal and tumor cells. Furthermore, we demonstrate that these copy gains are transient and that combined cues and/or epigenetic factor manipulation are sufficient to promote higher copy number amplifications. Overall, we describe a series of key observations that demonstrate oncogenic amplification is hardwired into cells, providing a definable basis for cellular plasticity for EGFR copy number in both normal and cancer cells, which has significant clinical implications.

Specificity, Crosstalk and Methylation States

Prior studies have illustrated that both somatic and tumor cells have extrachromosomal DNA (ecDNA; (11,55)) with key oncogenes such as MYC and EGFR occurring as ecDNA in as many as 50% of tumors (11). Early studies on extrachromosomal MYC demonstrated that the ecDNA harbored epigenetic states associated with active gene expression (56). Consistent with these observations, a recent study in somatic cells illustrated that ecDNAs were observed in gene-rich chromosomal regions (55), which suggested a relationship between their generation and actively marked loci. Our s evidence shows that by being able to directly promote or block such modifications through manipulation of histones, histone modifying enzymes and their upstream regulators such as hypoxia. The data presented within this manuscript illustrates a critical role for KMT-KDMs in balancing the methylation states controlling the repressive state (H3K9/27 methylation) and more accessible, active states (H3K4 methylation) so that EGFR amplification is either blocked or promoted.

Methylation states appear to control the predilection of a region to amplify, however, not all enzymes controlling those states are responsible for generating the EGFR amplifications. For example, KDM4A and KDM5A were the only members within their lysine demethylase enzyme families to promote EGFR. However, the KDM6 family members, KDM6A and KDM6B, were both sufficient to generate EGFR amplification upon overexpression, which suggest that these enzymes could have functional redundancy at this locus in controlling H3K27me3 balance. These data highlight that enzyme families could have unique targets, and in certain cases, overlapping specificity.

Similar observations were also true for KMTs targeting H3K4/9 methylation. For example, KMT2A/MLL1, SETD1A and SETD1B promoted EGFR amplification (FIG. 9). SETD1A was not responsible for previously identified TSSGs (10), highlighting the specificity for KMT2 family members in controlling genomic regions undergoing TSSG. Similarly, all H3K9 KMTs except KMT1C/G9a/EHMT2 promoted EGFR copy gains when depleted from cells. The EGFR locus has a clear pattern for the H3K9mel/2/3 distribution across the locus, which suggest an important arrangement for these methylation states and their associated KMTs. In fact, H3K9M introduction promoted EGFR low and higher level copy gains (FIG. 1). Therefore, future studies need to interrogate the dependencies of regions on the various members and establish regions that have unique targets or overlapping control.

Data presented here implies that KDM4A utilizes the same mechanism to generate EGFR amplification as other previously mapped regions undergoing copy gains (e.g., 1921.3-CKS1B; (10,17,18)). KDM4A and KDM4B were shown to recruit the replication machinery and facilitate rereplication (10,18). Our previous studies also demonstrated that H3K4 methylation was key to the recruitment of KDM4 family members and the modulation of chromosome 1 targets, which was driven by select H3K4 KMTs (10). These previous studies did not observe a role for H3K27 methylation in controlling the TSSG formation (10,18). However, H3K27me3 was a key modulator of EGFR amplification. Indeed, EZH2 depletion and chemical inhibition promoted EGFR copy gains. EZH2 occupies the blocks of H3K27me3 that flank H3K4 methylation within the EGFR locus. Furthermore, H3K4 methylation interference or depletion of the KMT2 enzymes that control EGFR amplification completely blocked the EGFR copy gains generated by EZH2 suppression or inhibition. These data are consistent with the collection of studies illustrating an antagonistic relationship between these methylation states and the associated enzymes promoting H3K4/27 methylation balance (48). Our data is also consistent with a recent report demonstrating cross-talk between EZH2 and KMT2A disrupts H3K27 methylation balance, resulting in resistance to EZH2i monotherapy (57). Therefore, common principles assigned to gene regulation appear be true for TSSG regulation, which has direct clinical implications.

Cues, Epigenetics and Targeting Heterogeneity

Previous studies have illustrated EGFR amplification plasticity (12). EGFR copy gains can range from few in number to large clouds in the nuclei of cancer cells (see FIG. 5; (42)). Glioblastoma patients that received EGFRi have been shown to develop resistance because ecDNA copies of EGFR disappear. However, upon drug removal EGFR ecDNA recurs, reestablishing sensitivity to targeted therapy (12). This plasticity has also been illustrated in cell culture as EGFR copy gains disappear in some cell lines (e.g., GBM cells). A recent study demonstrated however, that supplementing EGF enables propagation of the EGFR amplifications (54). Therefore, there is a critical need to understand the mechanisms that promote or suppress this amplification event.

Consistent with the prior body of work suggesting certain extracellular cues (hypoxia and EGF) associate with tumor cells harboring EGFR amplification, we have now demonstrated that these stimuli directly control EGFR DNA copy number (FIGS. 1I, 13). We observe that hypoxia-induced stabilization (17) and the catalytic activity of KDM4A is a central component in generating EGFR amplification. In fact, KDM4 chemical inhibition was sufficient to reduce this oncogenic amplification in hypoxia-stimulated cells as well as lung cancer cells harboring EGFR ecDNA. This observation is critical because it suggests that targeting KDM4A with small molecules could serve as a novel approach to control EGFR amplification and heterogeneity observed in hypoxic tumors. In addition, amplification of wild type EGFR has been shown to drive acquired resistance to mutation-selective EGFR tyrosine kinase inhibitors, identifying an additional therapeutic arena for potentially deploying KDM4i therapy (58).

EGF treatment does not impact KDM4A levels but rather triggers EGFR amplification through two specific H3K4 KMTs-KMT2A/MLL1 and SETD1A. While both KMT2A and SETD1A controlled EGF-induced copy gains, SETD1B was dispensable, which highlights that enzymes can be selectively required under certain physiological conditions to generate DNA copy gains. Future studies should address whether other cellular signals or stresses could serve as important triggers to selectively activate or repress the enzymes required to generate amplification at EGFR and other TSSG sites. Understanding the triggers for amplifications will provide insights into tumor heterogeneity and uncover novel biomarkers and drug targets in controlling amplification.

Consistent with these two pathways (hypoxia and EGF) working in parallel, when hypoxia is combined with KDM4A, there is little change in the low copy number (data not shown); however, when combined with increased H3K4 methylation there are higher copy number gains of EGFR per nucleus. The same is true when EGF is combined with KDM4A overexpression. These data illustrate that combining extracellular cues and epigenetic factor alterations promotes EGFR copy number generation and the degree of amplification. Given the range of EGFR amplification across tumors (FIG. 1A), these observations could be important when considering variables impacting DNA copy number plasticity in tumors and when considering ways to therapeutically intervene.

Data presented within this manuscript is suggestive of two populations of EGFR DNA amplifications. For example, in cancer cell lines which exhibit significant DNA amplification of EGFR (e.g. HCC827 or HT-29 cells), these amplifications are reduced by modulation of K4 methylation via the introduction of a H3.3 K4M methyl-deficient mutant, or inhibition/depletion of KDM4A. However, despite a reduction in EGFR DNA amplification under these conditions, significant levels of EGFR amplification remain. Future studies will need to investigate this in more detail, but these results could indicate a balance between integrated DNA copy number amplification and transient extrachromosomal amplifications of EGFR, the latter of which appears targetable with compounds directed towards epigenetic modifiers.

In closing, we have uncovered both chromatin modifiers and extracellular signals that control EGFR amplification and demonstrate that epigenetic therapies could hold a key to modulating EGFR copy number heterogeneity in cancer and associated diseases, which could have significant clinical implications in the future.

Example II

Clinical Application of Methods for Modulating EGFR Expression Levels for Sensitizing Cancer Cells to EGFR Directed Therapies The results described in Example I elucidating the role methylation plays in EGFR DNA amplification have facilitated the design of strategies for treating the individuals based on the level of EGFR amplification in their particular cancer, and their response to EGFR inhibitors (EGFRi), receptor tyrosine kinase (RTK) therapies and related therapies.

Figure 15:
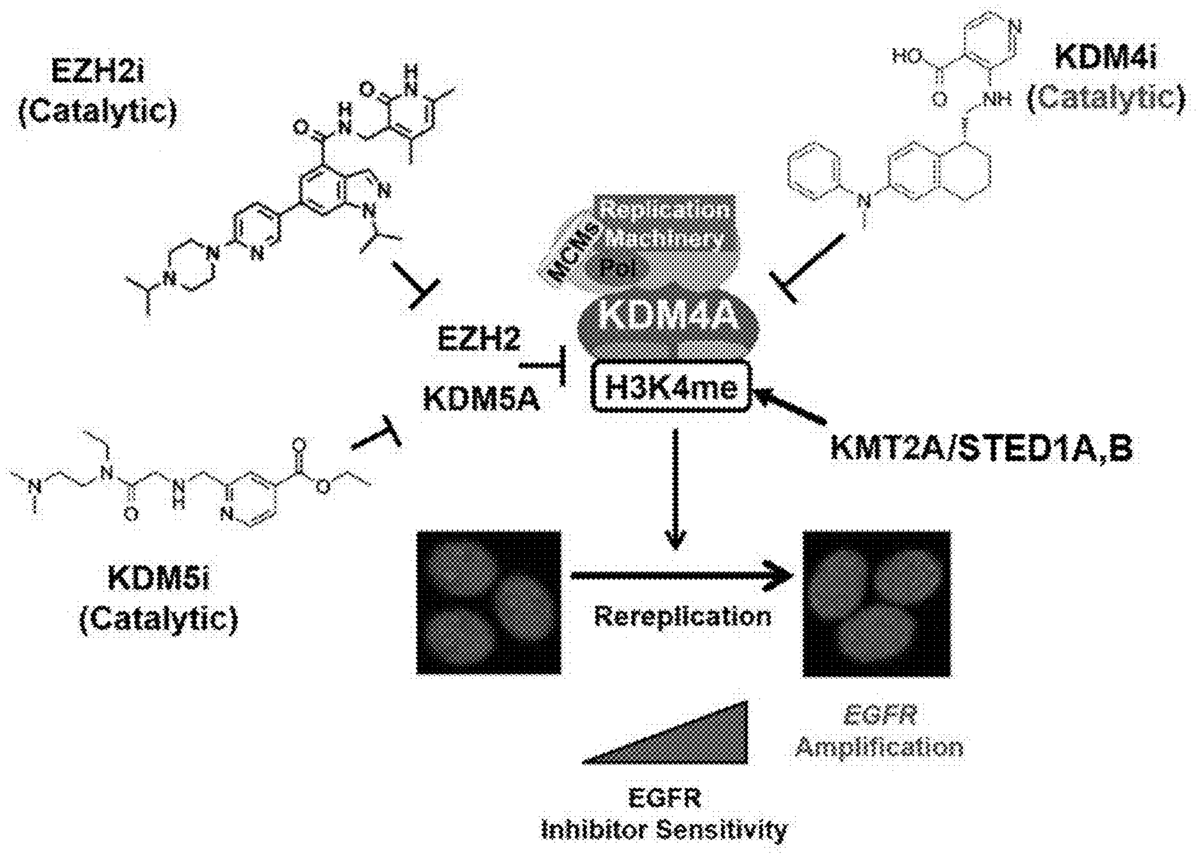
FIG. 15: Druggable Epigenetic Mechanisms Control ecDNA Amplification & Therapeutic Response. A schematic diagram depicting the interplay between the various molecules and pathways disclosed herein.
Figure 16A:
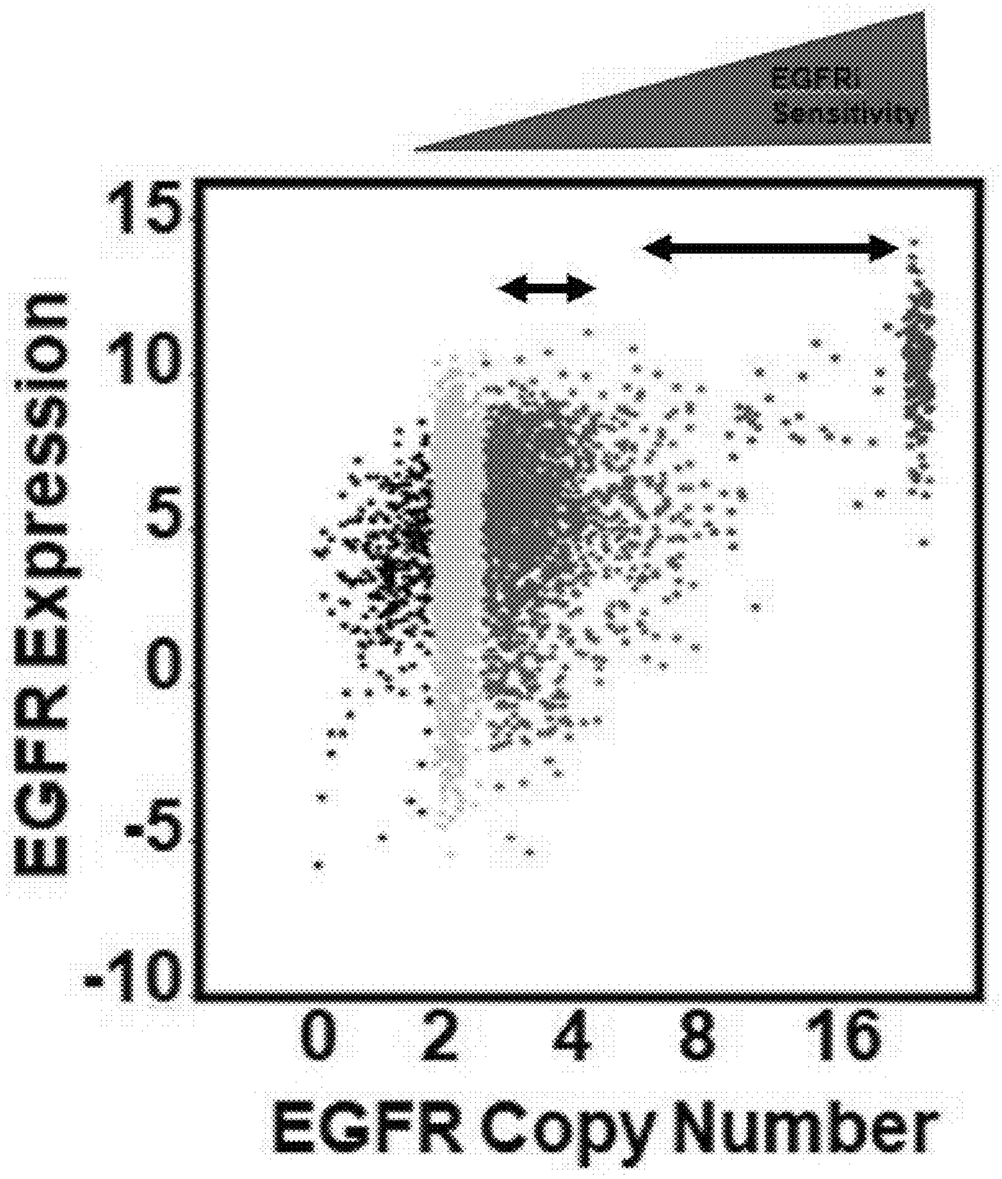
FIG. 16A-B: Modulation of EGFR amplification to increase chemosensitivity to anti-cancer agents. Tumors with uniform EGFR levels or with higher uniform levels (as indicated by arrows) are sensitized to EGFR inhibitors.

The effects of different compounds and their effects to modulate EGFRi therapies are summarized in FIG. 15. This figure, and the data provided herein, show for the first time that EGFR gene DNA copy levels modulate response to epidural growth factor or to EGFR inhibitors and thus modulation of EGFR copy number can be used to advantage to sensitize tumor cells to anti-cancer therapies. and KDM4A and the associated complex promoting replication cause the increase in EGFR copy gains when overexpressed or amplified in tumors. For example, HCC827 NSCLC cells have amplified KDM4A at the DNA level (FIG. 16A) and when inhibited, exhibit reduced levels of amplification and reduced growth attributable to the reduced amount of EGFR (FIG. 5A-5D). KDM4A is targeted through the H3K4 methylation controlled by KMT2A, SETD1A and SETD1B. When this methylation is blocked, there is a reduction in EGFR gains. Compositions and methods described herein deplete or chemically suppress KDM4A and thereby prevent the KMT2 enzyme family promoted amplifications. Furthermore, we describe enhancement of methylation and KDM4A-driven EGFR amplification, by suppressing EZH2 and KDM5A. Both enzymes rheostat methylation levels promoting KDM4A to drive amplification of EGFR copy numbers. Therefore, we can increase the copies to enhance a response to either growth factor or EGFR inhibitors by inhibiting these enzymes. This approach increases chemosensitivity and streamlines treatment regimens for the patient. Furthermore, KDM4A suppression would then prevent their ability to cause the EGFR DNA copy gains. These data support the various modulatory approaches for controlling EGFR amplification levels for therapeutic benefit.

One approach for sensitizing tumors to EGFRi or other related RTK therapies includes without limitation, determining the EGFR copy number by DNA FISH or other suitable method and assessing whether increased expression/amplification is present and modulation of copy numbers is in order. Enhancer of zeste homolog 2 (EZH2) is the enzymatic catalytic subunit of polycomb repressive complex 2 (PRC2) that can alter downstream target genes expression by trimethylation of Lys-27 in histone 3 (H3K27me3). We have found that suppression of EZH2 is effective to increase EGFR amplification. EZH2 inhibitors are available, including the EZH1/2 dual inhibitors or inhibitors that disrupt EZH2 function such as EED inhibitors. An exemplary molecule includes tazemetostat by Epizyme. Tumors can be treated with EZH2 inhibitor for a suitable time to amplify the EGFR copy number above base line, followed by treatment EGFRi or related therapies. This strategy is consistent with the amplification levels we observed and the sensitivities previously shown in the colorectal cancer cell lines in Example I. In a similar fashion, KDM5 family or KDM5A specific inhibitors, which are also available, can be used to increase the gain levels and in turn enhance the therapeutic response to EGFRi. In a similar fashion, tumors with diploid copies should be pretreated and then treated with the EGFRi or related therapies.

Figure 16B:
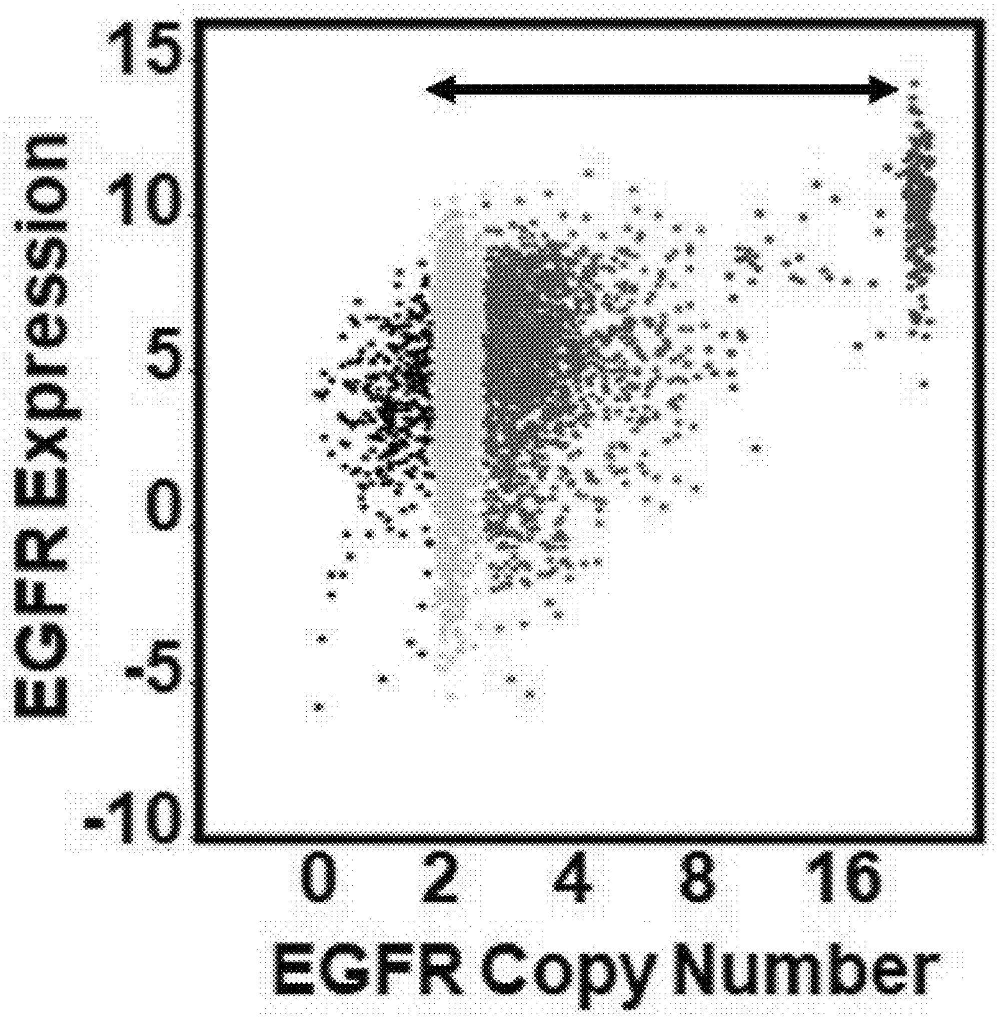

In certain cases, loss of EGFR DNA copies have been observed in certain tumors (FIG. 1A, 16A, 16B), these tumors can also be targeted with agent to increase EGFR levels/copies, thereby sensitizing the cells to follow on treatment with EGFRi or related therapies.

In other aspects of the methods, the levels of the enzymes that promote the amplifications and prevent the amplifications are assessed at the protein, RNA and cellular localization level as this can guide stratification of treatment. Mutational status can optionally be determined as well. For example, if KDM4A expression is observed to be high, this fining correlates with EGFR amplification, and thus the ability to sensitize the tumor cells to EGFRi. In cases where low EZH2 levels are present, or mis-localization or mutations associated with function (direct or indirect of complex members, facilitating activity) are indicative of the suitability of EGFRi or related therapies. Notably, high EZH2 or KDM5A levels are likely to suppress EGFR copy gains and in turn prevent the response in conditions such as hypoxia. Accordingly, targeting these molecules should also promote amplification and sensitization to EGFRi. KMT2A, SETD1A or SETD1B overexpression also promotes EGFR amplification, rendering cells more sensitive to EGFRi. In cases where H3K9 KMT expression levels are reduced, we expect increased EGFR copies and in turn sensitivity of these tumor types to EGFRi or related therapies. Therefore, targeting these H3K9 KMTs (e.g., EHMT1) can be used to amplify EGFR and sensitize tumors. (80)

Figure 17:
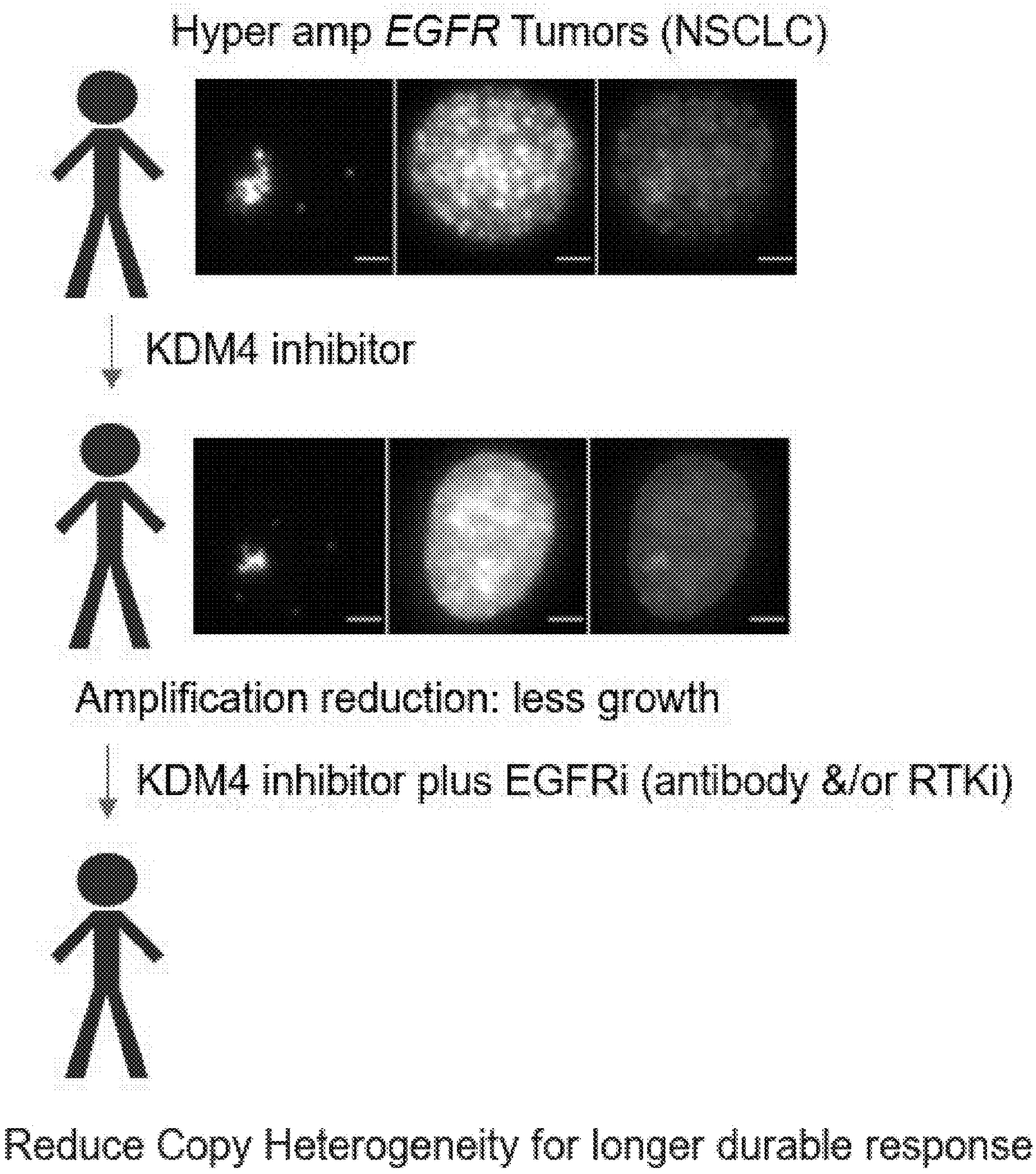
FIG. 17: Treatment strategy for tumors having increased EGFR amplification (e.g., NSCLC or GBM). Treatment with KDM4i reduces the growth and resets EGFR copy number and heterogeneity. This treatment is then followed up with EGFRi therapy with KDM4i. Keeping KDM4 inhibited by continued dosing is essential.
Figure 18:
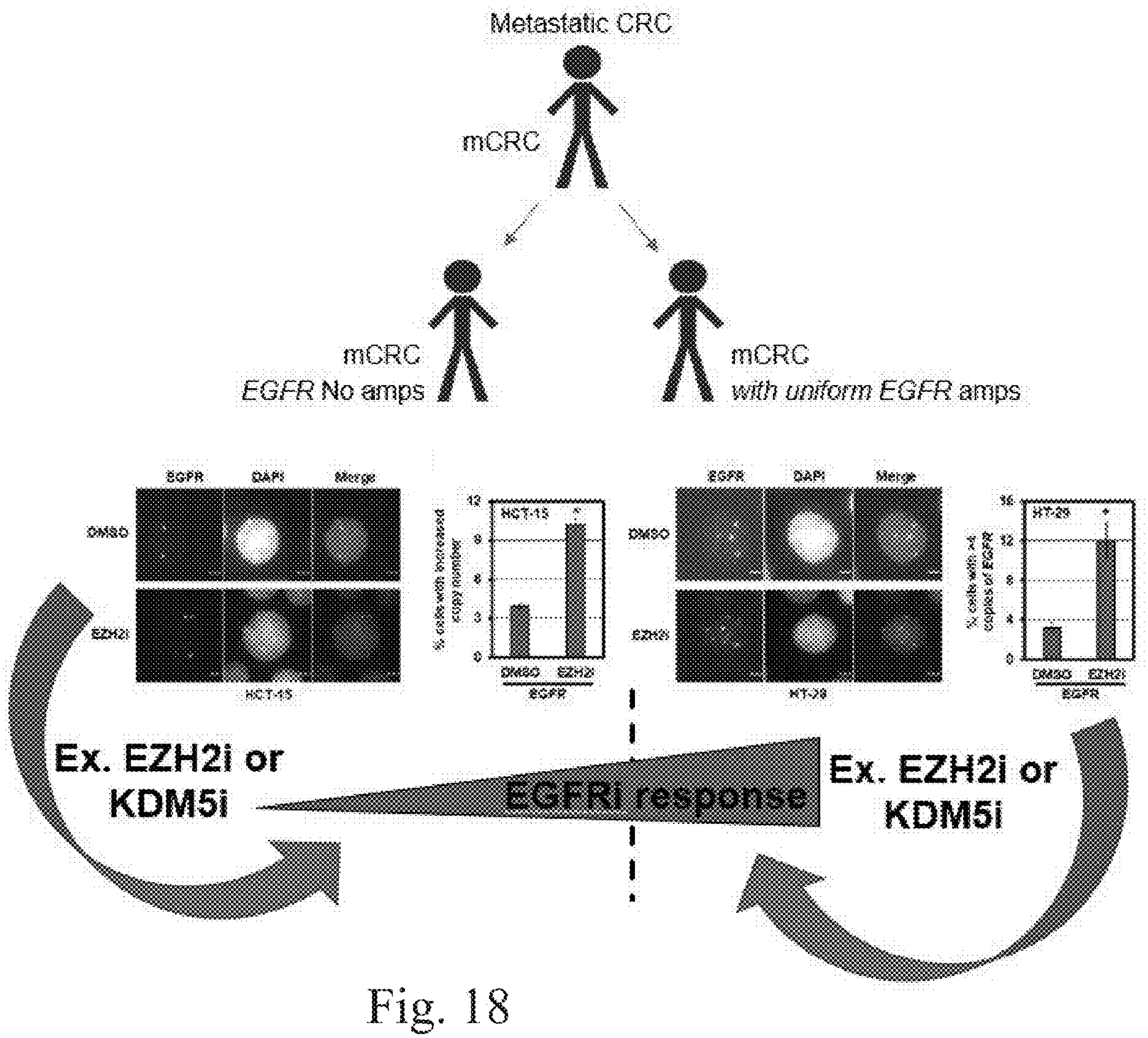
FIG. 18: Test and treat protocol for assessing EGFR amplification levels and tailoring treatment regimen of tumors accordingly. For example, when no EGFR amplifications, or low amplifications are present, treatment with EZH2i or KDM5i increases the response to EGFRi. When EGFR amplifications are uniform, treatment increases the copies and response so the amplifications are higher than 4 copy numbers. If EGFR amplifications are sufficiently heterogenous, KDM4i treatment would be applied before the EZH2i/KDM5i and EGFRi combination treatment.

Tumors with very high amplification (e.g., those with >8 copies or clouds measured as described in FIGS. 1A, 5, and 16A-16B), reducing the extrachromosomal DNA or DNA copies will reduce the amount of response. In such cases, it is desirable to increase the homogeneity of EGFR expression levels throughout the tumor. Intratumor heterogeneity for EGFR DNA copy gains is then reduced so that a more uniform response to the EGFRi can be achieved. In such cases, treatment with KDM4 family or KDM4A-selective inhibition would promote reduced heterogeneity and more consistent response to the therapies over time. Inhibition of these molecules can be achieved at the nucleic acid or protein levels. See FIG. 17.

In a similar fashion, our data documents the plasticity of EGFR based on hypoxia and/or EGF, therefore, KDM4 family or KDM4A selective inhibitors can be used to reduce the EGFR heterogeneity within a tumor in order to achieve a more consistent response. Thus, in these types of tumors, one can also drive gains even higher through EZH2i or KDM5i in order to sensitize the tumor to drug.

REFERENCES

1. Hanahan D, Weinberg R A. Hallmarks of cancer: the next generation. Cell 2011; 144(5):646-74 doi 10.1016/j.cell.2011.02.013.
2. Mishra S, Whetstine J R. Different Facets of Copy Number Changes: Permanent, Transient, and Adaptive. Mol Cell Biol 2016 doi 10.1128/MCB.00652-15.
3. Diskin S J, Hou C, Glessner J T, Attiyeh E F, Laudenslager M, Bosse K, et al. Copy number variation at 1921.1 associated with neuroblastoma. Nature 2009; 459(7249): 987-91 doi 10.1038/nature08035.
4. Fonseca R, Van Wier S A, Chng W J, Ketterling R, Lacy M Q, Dispenzieri A, et al. Prognostic value of chromosome 1q21 gain by fluorescent in situ hybridization and increase CKS1B expression in myeloma. Leukemia 2006; 20(11):2034-40 doi 10.1038/sj.leu.2404403.
5. Goeze A, Schluns K, Wolf G, Thasler Z, Petersen S, Petersen I. Chromosomal imbalances of primary and metastatic lung adenocarcinomas. J Pathol 2002; 196(1): 8-16 doi 10.1002/path.1009.
6. Inoue J, Otsuki T, Hirasawa A, Imoto I, Matsuo Y, Shimizu S, et al. Overexpression of PDZK1 within the 112-q22 amplicon is likely to be associated with drug-resistance phenotype in multiple myeloma. The American journal of pathology 2004; 165(1):71-81 doi 10.1016/S0002-9440(10)63276-2.
7. Kudoh K, Takano M, Koshikawa T, Hirai M, Yoshida S, Mano Y, et al. Gains of 1q21-q22 and 13q12-q14 are potential indicators for resistance to cisplatin-based chemotherapy in ovarian cancer patients. Clinical cancer research: an official journal of the American Association for Cancer Research 1999; 5(9):2526-31.
8. Petersen S, Aninat-Meyer M, Schluns K, Gellert K, Dietel M, Petersen I. Chromosomal alterations in the clonal evolution to the metastatic stage of squamous cell carcinomas of the lung. Br J Cancer 2000; 82(1):65-73 doi 10.1054/bjoc.1999.0878.
9. Beroukhim R, Mermel C H, Porter D, Wei G, Raychaudhuri S, Donovan J, et al. The landscape of somatic copy-number alteration across human cancers. Nature 2010; 463(7283):899-905 doi 10.1038/nature08822.
10. Mishra S, Van Rechem C, Pal S, Clarke T L, Chakraborty D, Mahan S D, et al. Cross-talk between Lysine-Modifying Enzymes Controls Site-Specific DNA Amplifications. Cell 2018; 174(4):803-17 e16 doi 100.1016/j.cell.2018.06.018.
11. Turner K M, Deshpande V, Beyter D, Koga T, Rusert J, Lee C, et al. Extrachromosomal oncogene amplification drives tumour evolution and genetic heterogeneity. Nature 2017; 543(7643):122-5 doi 10.1038/nature21356.
12. Nathanson D A, Gini B, Mottahedeh J, Visnyei K, Koga T, Gomez G, et al. Targeted therapy resistance mediated by dynamic regulation of extrachromosomal mutant EGFR DNA. Science 2014; 343(6166):72-6 doi 10.1126/science.1241328.
13. Biedler J L, Spengler B A. A novel chromosome abnormality in human neuroblastoma and antifolate-resistant Chinese hamster cell lives in culture. Journal of the National Cancer Institute 1976; 57(3):683-95.
14. Biedler J L, Spengler B A. Metaphase chromosome anomaly: association with drug resistance and cell-specific products. Science 1976; 191(4223):185-7.
15. Alt F W, Kellems R E, Bertino J R, Schimke R T. Selective multiplication of dihydrofolate reductase genes in methotrexate-resistant variants of cultured murine cells. The Journal of biological chemistry 1978; 253(5): 1357-70.
16. Haber D A, Schimke R T. Unstable amplification of an altered dihydrofolate reductase gene associated with double-minute chromosomes. Cell 1981; 26(3 Pt 1):355-62.
17. Black J C, Atabakhsh E, Kim J, Biette K M, Van Rechem C, Ladd B, et al. Hypoxia drives transient site-specific copy gain and drug-resistant gene expression. Genes & development 2015; 29(10):1018-31 doi 10.1101/gad.259796.115.
18. Black J C, Manning A L, Van Rechem C, Kim J, Ladd B, Cho J, et al. KDM4A lysine demethylase induces site-specific copy gain and rereplication of regions amplified in tumors. Cell 2013; 154(3):541-55 doi 10.1016/j.cell.2013.06.051.
19. Black J C, Zhang H, Kim J, Getz G, Whetstine J R. Regulation of Transient Site-specific Copy Gain by microRNA. The Journal of biological chemistry 2016 doi 10.1074/jbc.M115.711648.
20. Black J C, Whetstine J R. Too little O2 Too much gain. Cell cycle 2015; 14(18):2869-70 doi 10.1080/15384101.2015.1076659.
21. Junttila M R, de Sauvage F J. Influence of tumour micro-environment heterogeneity on therapeutic response. Nature 2013; 501(7467):346-54 doi 10.1038/nature12626.
22. Hirsch F R, Varella-Garcia M, Bunn P A, Jr., Di Maria M V, Veve R, Bremmes R M, et al. Epidermal growth factor receptor in non-small-cell lung carcinomas: correlation between gene copy number and protein expression and impact on prognosis. J Clin Oncol 2003; 21(20):3798-807 doi 10.1200/JCO.2003.11.069.
23. Sullivan I, Planchard D. Next-Generation EGFR Tyrosine Kinase Inhibitors for Treating EGFR-Mutant Lung Cancer beyond First Line. Front Med (Lausanne) 2016; 3:76 doi 10.3389/fmed.2016.00076.
24. Hirsch F R, Varella-Garcia M, McCoy J, West H, Xavier A C, Gumerlock P, et al. Increased epidermal growth factor receptor gene copy number detected by fluorescence in situ hybridization associates with increased sensitivity to gefitinib in patients with bronchioloalveolar carcinoma subtypes: a Southwest Oncology Group Study. J Clin Oncol 2005; 23(28):6838-45 doi 10.1200/JCO.2005.01.2823.
25. Maron S B, Alpert L, Kwak H A, Lomnicki S, Chase L, Xu D, et al. Targeted Therapies for Targeted Populations: Anti-EGFR Treatment for EGFR-Amplified Gastroesophageal Adenocarcinoma. Cancer Discov 2018; 8(6):696-713 doi 10.1158/2159-8290.CD-17-1260.
26. Huang J, Fan Q, Lu P, Ying J, Ma C, Liu W, et al. Icotinib in Patients with Pretreated Advanced Esophageal Squamous Cell Carcinoma with EGFR Overexpression or EGFR Gene Amplification: A Single-Arm, Multicenter Phase 2 Study. J Thorac Oncol 2016; 11(6):910-7 doi 10.1016/j.jtho.2016.02.020.
27. Luber B, Deplazes J, Keller G, Walch A, Rauser S, Eichmann M, et al. Biomarker analysis of cetuximab plus oxaliplatin/leucovorin/5-fluorouracil in first-line metastatic gastric and oesophago-gastric junction cancer: results from a phase II trial of the Arbeitsgemeinschaft Internistische Onkologie (AIO). BMC Cancer 2011; 11:509 doi 10.1186/1471-2407-11-509.
28. Petty R D, Dahle-Smith A, Stevenson D A J, Osborne A, Massie D, Clark C, et al. Gefitinib and EGFR Gene Copy Number Aberrations in Esophageal Cancer. J Clin Oncol 2017; 35(20):2279-87 doi 10.1200/JCO.2016.70.3934.
29. Herbst R S, Redman M W, Kim E S, Semrad T J, Bazhenova L, Masters G, et al. Cetuximab plus carboplatin and paclitaxel with or without bevacizumab versus carboplatin and paclitaxel with or without bevacizumab in advanced NSCLC (SWOG S0819): a randomised, phase 3 study. Lancet Oncol 2018; 19(1):101-14 doi 10.1016/51470-2045(17)30694-0.
30. Lewis P W, Muller M M, Koletsky M S, Cordero F, Lin S, Banaszynski L A, et al. Inhibition of PRC2 activity by a gain-of-function H3 mutation found in pediatric glioblastoma. Science 2013; 340(6134):857-61 doi 10.1126/science.1232245.
31. Jiang X R, Jimenez G, Chang E, Frolkis M, Kusler B, Sage M, et al. Telomerase expression in human somatic cells does not induce changes associated with a transformed phenotype. Nat Genet 1999; 21(1):111-4 doi 10.1038/5056.
32. Darrow E M, Huntley M H, Dudchenko O, Stamenova E K, Durand N C, Sun Z, et al. Deletion of DXZ4 on the human inactive X chromosome alters higher-order genome architecture. Proc Natl Acad Sci USA 2016; 113(31):E4504-12 doi 10.1073/pnas.1609643113.
33. Kundu S, Ji F, Sunwoo H, Jain G, Lee J T, Sadreyev R I, et al. Polycomb Repressive Complex 1 Generates Discrete Compacted Domains that Change during Differentiation. Mol Cell 2017; 65(3):432-46 e5 doi 10.1016/j.molcel.2017.01.009.
34. Consortium E P. An integrated encyclopedia of DNA elements in the human genome. Nature 2012; 489(7414):57-74 doi 10.1038/nature11247.
35. Rao S S, Huntley M H, Durand N C, Stamenova E K, Bochkov I D, Robinson J T, et al. A 3D map of the human genome at kilobase resolution reveals principles of chromatin looping. Cell 2014; 159(7):1665-80 doi 10.1016/j.cell.2014.11.021.
36. Stafford J M, Lee C H, Voigt P, Descostes N, Saldana-Meyer R, Yu J R, et al. Multiple modes of PRC2 inhibition elicit global chromatin alterations in H3K27M pediatric glioma. Sci Adv 2018; 4(10):eaau5935 doi 10.1126/sciadv.aau5935.
37. Black J C, Van Rechem C, Whetstine J R. Histone lysine methylation dynamics: establishment, regulation, and biological impact. Mol Cell 2012; 48(4):491-507 doi 10.1016/j.molcel.2012.11.006.
38. Whetstine J R, Nottke A, Lan F, Huarte M, Smolikov S, Chen Z, et al. Reversal of histone lysine trimethylation by the JMJD2 family of histone demethylases. Cell 2006; 125(3):467-81 doi 10.1016/j.cell.2006.03.028.
39. Huang Y, Fang J, Bedford M T, Zhang Y, Xu R M. Recognition of histone H3 lysine-4 methylation by the double tudor domain of JMJD2A. Science 2006; 312 (5774):748-51 doi 10.1126/science.1125162.
40. Metzger E, Stepputtis S S, Strietz J, Preca B T, Urban S, Willmann D, et al. KDM4 Inhibition Targets Breast Cancer Stem-like Cells. Cancer Res 2017; 77(21):5900-12 doi 10.1158/0008-5472.CAN-17-1754.
41. Amann J, Kalyankrishna S, Massion P P, Ohm J E, Girard L, Shigematsu H, et al. Aberrant epidermal growth factor receptor signaling and enhanced sensitivity to EGFR inhibitors in lung cancer. Cancer Res 2005; 65(1):226-35.
42. Varella-Garcia M. Stratification of non-small cell lung cancer patients for therapy with epidermal growth factor receptor inhibitors: the EGFR fluorescence in situ hybridization assay. Diagn Pathol 2006; 1:19 doi 10.1186/1746-1596-1-19.
43. Chen Y K, Bonaldi T, Cuomo A, Del Rosario J R, Hosfield D J, Kanouni T, et al. Design of KDM4 Inhibitors with Antiproliferative Effects in Cancer Models. ACS Med Chem Lett 2017; 8(8):869-74 doi 10.1021/acsmedchemlett.7b00220.
44. Egan B, Yuan C C, Craske M L, Labhart P, Guler G D, Arnott D, et al. An Alternative Approach to ChIP-Seq Normalization Enables Detection of Genome-Wide Changes in Histone H3 Lysine 27 Trimethylation upon EZH2 Inhibition. PLoS One 2016; 11(11):e0166438 doi 10.1371/journal.pone.0166438.
45. Yang X, Li F, Konze K D, Meslamani J, Ma A, Brown P J, et al. Structure-Activity Relationship Studies for Enhancer of Zeste Homologue 2 (EZH2) and Enhancer of Zeste Homologue 1 (EZH1) Inhibitors. J Med Chem 2016; 59(16):7617-33 doi 10.1021/acs.jmedchem.6b00855.
46. Katona B W, Liu Y, Ma A, Jin J, Hua X. EZH2 inhibition enhances the efficacy of an EGFR inhibitor in suppressing colon cancer cells. Cancer Biol Ther 2014; 15(12):1677-87 doi 10.4161/15384047.2014.972776.
47. Shilatifard A. The COMPASS family of histone H3K4 methylases: mechanisms of regulation in development and disease pathogenesis. Annu Rev Biochem 2012; 81:65-95 doi 10.1146/annurev-biochem-051710-134100.
48. Schuettengruber B, Bourbon H M, Di Croce L, Cavalli G. Genome Regulation by Polycomb and Trithorax: 70 Years and Counting. Cell 2017; 171(1):34-57 doi 10.1016/j.cell.2017.08.002.
49. Rickels R, Hu D, Collings C K, Woodfin A R, Piunti A, Mohan M, et al. An Evolutionary Conserved Epigenetic Mark of Polycomb Response Elements Implemented by Trx/MLL/COMPASS. Mol Cell 2016; 63(2):318-28 doi 10.1016/j.molcel.2016.06.018.
50. Koubi M, Poplineau M, Vernerey J, N'Guyen L, Tiberi G, Garciaz S, et al. Regulation of the positive transcriptional effect of PLZF through a non-canonical EZH2 activity. Nucleic Acids Res 2018; 46(7):3339-50 doi 10.1093/nar/gky080.
51. Johansson C, Velupillai S, Tumber A, Szykowska A, Hookway E S, Nowak R P, et al. Structural analysis of human KDM5B guides histone demethylase inhibitor development. Nat Chem Biol 2016; 12(7):539-45 doi 10.1038/nchembio.2087.
52. Horton J R, Liu X, Gale M, Wu L, Shanks J R, Zhang X, et al. Structural Basis for KDM5A Histone Lysine Demethylase Inhibition by Diverse Compounds. Cell Chem Biol 2016; 23(7):769-81 doi 10.1016/j.chembiol.2016.06.006.
53. Sharma S V, Lee D Y, Li B, Quinlan M P, Takahashi F, Maheswaran S, et al. A chromatin-mediated reversible drug-tolerant state in cancer cell subpopulations. Cell 2010; 141(1):69-80 doi 10.1016/j.cell.2010.02.027.
54. William D, Mokri P, Lamp N, Linnebacher M, Classen C F, Erbersdobler A, et al. Amplification of the EGFR gene can be maintained and modulated by variation of EGF concentrations in in vitro models of glioblastoma multiforme. PLoS One 2017; 12(9):e0185208 doi 10.1371/journal.pone.0185208.
55. Moller H D, Mohiyuddin M, Prada-Luengo I, Sailani M R, Halling J F, Plomgaard P, et al. Circular DNA elements of chromosomal origin are common in healthy human somatic tissue. Nat Commun 2018; 9(1):1069 doi 10.1038/s41467-018-03369-8.
56. Smith G, Taylor-Kashton C, Dushnicky L, Symons S, Wright J, Mai S. c-Myc-induced extrachromosomal elements carry active chromatin. Neoplasia 2003; 5(2):110-20.
57. Huang X, Yan J, Zhang M, Wang Y, Chen Y, Fu X, et al. Targeting Epigenetic Crosstalk as a Therapeutic Strategy for EZH2-Aberrant Solid Tumors. Cell 2018; 175(1):186-99 e19 doi 10.1016/j.cell.2018.08.058.
58. Nukaga S, Yasuda H, Tsuchihara K, Hamamoto J, Masuzawa K, Kawada I, et al. Amplification of EGFR Wild-Type Alleles in Non-Small Cell Lung Cancer Cells Confers Acquired Resistance to Mutation-Selective EGFR Tyrosine Kinase Inhibitors. Cancer Res 2017; 77(8):2078-89 doi 10.1158/0008-5472.CAN-16-2359.
59. Dobin A, Davis C A, Schlesinger F, Drenkow J, Zaleski C, Jha S, et al. STAR: ultrafast universal RNA-seq aligner. Bioinformatics 2013; 29(1):15-21 doi 10.1093/bioinformatics/bts635.
60. Anders S, Pyl P T, Huber W. HTSeq—a Python framework to work with high-throughput sequencing data. Bioinformatics 2015; 31(2):166-9 doi 10.1093/bioinformatics/btu638.
61. Robinson M D, McCarthy D J, Smyth G K. edgeR: a Bioconductor package for differential expression analysis of digital gene expression data. Bioinformatics 2010; 26(1):139-40 doi 10.1093/bioinformatics/btp616.
62. Li H, Durbin R. Fast and accurate long-read alignment with Burrows-Wheeler transform. Bioinformatics 2010; 26(5):589-95 doi 10.1093/bioinformatics/btp698.
63. Ramirez F, Ryan D P, Gruning B, Bhardwaj V, Kilpert F, Richter A S, et al. deepTools2: a next generation web server for deep-sequencing data analysis. Nucleic Acids Res 2016; 44(W1):W160-5 doi 10.1093/nar/gkw257.
64. Consortium E P. The ENCODE (ENCyclopedia Of DNA Elements) Project. Science 2004; 306(5696):636-40 doi 10.1126/science.1105136.
65. Edgar R, Domrachev M, Lash A E. Gene Expression Omnibus: NCBI gene expression and hybridization array data repository. Nucleic Acids Res 2002; 30(1):207-10 doi 10.1093/nar/30.1.207.
66. Li H, Durbin R. Fast and accurate short read alignment with Burrows-Wheeler transform. Bioinformatics 2009; 25(14):1754-60 doi 10.1093/bioinformatics/btp324.
67. Young K. Chen et al. *ACS Medicinal Chemistry Letters* 2017 8 (8), 869-874 DOI: 10.1021/acsmedchemlett.7b00220
68. Lin H, et al. Small molecule KDM4s inhibitors as anti-cancer agents. J Enzyme Inhib Med Chem. 2018; 33(1):777-793. doi:10.1080/14756366.2018.1455676
69. International Patent Application No. PCT/US2018/024624.
70. Eric Metzger et al. KDM4 Inhibition Targets Breast Cancer Stem-like Cells. Cancer Res; 77(21) Nov. 1, 2017. doi: 10.1158/0008-5472.CAN-17-1754
71. Chen Y K, Bonaldi T, Cuomo A, et al. Design of KDM4 Inhibitors with Antiproliferative Effects in Cancer Models. ACS Med Chem Lett. 2017; 8(8):869-874. Published 2017 Jul. 27. doi:10.1021/acsmedchemlett.7b00220
72. International Patent Application No. PCT/US2014/029432.
73. Vinogradova, M., Gehling, V., Gustafson, A. et al. An inhibitor of KDM5 demethylases reduces survival of drug-tolerant cancer cells. Nat Chem Biol 12, 531-538 (2016). https://doi.org/10.1038/nchembio.2085.
74. Leadem B R, Kagiampakis I, Wilson C, et al. A KDM5 Inhibitor Increases Global H3K4 Trimethylation Occupancy and Enhances the Biological Efficacy of 5-Aza-2'-Deoxycytidine. Cancer Res. 2018; 78(5):1127-1139. doi: 10.1158/0008-5472.CAN-17-1453.
75. Yang G J, Ko C N, Zhong H J, Leung C H, Ma D L. Structure-Based Discovery of a Selective KDM5A Inhibitor that Exhibits Anti-Cancer Activity via Inducing Cell Cycle Arrest and Senescence in Breast Cancer Cell Lines. Cancers (Basel). 2019; 11(1):92. Published 2019 Jan. 15. doi:10.3390/cancers11010092
76. Honma D, Kanno O, Watanabe J, et al. Novel orally bioavailable EZH1/2 dual inhibitors with greater antitumor efficacy than an EZH2 selective inhibitor. Cancer Sci. 2017; 108(10):2069-2078. doi:10.1111/cas.13326

77. Duan, R., Du, W. & Guo, W. EZH2: a novel target for cancer treatment. J Hematol Oncol 13, 104 (2020). https://doi.org/10.1186/s13045-020-00937-8

78. Yap T A, Winter J N, Giulino-Roth L, et al. Phase I Study of the Novel Enhancer of Zeste Homolog 2 (EZH2) Inhibitor GSK2816126 in Patients with Advanced Hematologic and Solid Tumors. Clin Cancer Res. 2019; 25(24): 7331-7339. doi:10.1158/1078-0432.CCR-18-4121

79. Yap T A, et al. A Phase I Study of GSK2816126, an Enhancer of Zeste Homolog 2(EZH2) Inhibitor, in Patients (pts) with Relapsed/Refractory Diffuse Large B-Cell Lymphoma (DLBCL), Other Non-Hodgkin Lymphomas (NHL), Transformed Follicular Lymphoma (tFL), Solid Tumors and Multiple Myeloma (MM). Blood 2016; 128 (22): 4203. doi: https://doi.org/10.1182/blood.V128.22.4203.4203

80. Currently being assessed. Clinical trial available on the world wide web at clinicaltrials.gov/ct2/show/NCT04067336

While certain features of the invention have been described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for treating a subject having EGFR inhibitor (EGFRi) resistant tumors, comprising;

a) contacting a tumor comprising altered EGFR copy numbers with an agent that modulates amplification of EGFR to a level which sensitizes cells in said tumor to EGFR inhibitors; and b) administering to said subject an EGFRi, thereby reducing tumor cell proliferation or inducing tumor cell killing which exceeds that observed in tumor cells not treated with the agent of step a)

wherein the modulation of EGFR reduces EGFR copy number heterogeneity.

2. The method of claim 1, wherein copy number is determined using DNA FISH.

3. The method of claim 1, wherein said EGFR copy number is high and said agent is selected from EZH2 inhibitor, KDM5 inhibitor and KDM5A inhibitor.

4. The method of claim 3, wherein said EZH2 inhibitor is tazemetostat.

5. The method of claim 4, wherein said tumor cells comprise diploid EGFR copies.

6. The method of claim 1, wherein said tumor cells have a copy number of EGFR between 3-7.

7. The method of claim 1, wherein said tumor cells have a copy number of EGFR of 8 or higher.

8. The method of claim 1, wherein there is a loss of heterozygosity in the EGFR region and the agent is an EZH2 inhibitor.

9. The method of claim 1, wherein copy number is low and step a) comprises contacting the cells with at least one histone lysine methyltransferase (KMT), thereby increasing EGFR copy number.

10. The method of claim 9, wherein the at least one KMT is selected from KMT2A, SETD1A and SETD1B.

11. The method according to claim 1, comprising administration of at least one EGFR inhibitor selected from gefitinib, erlotinib, lapatinib, cetuximab, Osimertinib, panitumumab, neratinib, vandetanib, necitumumab, and dacomitinib.

12. The method of claim 11 wherein the at least one EGFR inhibitor is selected from gefinitnib or lapatnib.

13. The method according to claim 12, wherein the modulation of EGFR reduces tumor heterogeneity.

* * * * *